US011155627B2

(12) United States Patent
Kim et al.

(10) Patent No.: US 11,155,627 B2
(45) **Date of Patent: *Oct. 26, 2021**

(54) ANTI-C-MET/ANTI-ANG2 BISPECIFIC ANTIBODY

(71) Applicant: Samsung Electronics Co., Ltd., Suwon-si (KR)

(72) Inventors: Hyung-Chan Kim, Yongin-si (KR); Kyung Eun Kim, Yongin-si (KR); Yoon Sook Lee, Gyeonggi-do (KR); Mi Young Cho, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 246 days.

This patent is subject to a terminal disclaimer.

(21) Appl. No.: 15/494,875

(22) Filed: Apr. 24, 2017

(65) Prior Publication Data

US 2017/0260273 A1 Sep. 14, 2017

Related U.S. Application Data

(62) Division of application No. 14/556,911, filed on Dec. 1, 2014, now Pat. No. 9,637,541.

(30) Foreign Application Priority Data

Nov. 29, 2013 (KR) ........................ 10-2013-0147624

(51) Int. Cl.

| | |
|---|---|
| ***C07K 16/28*** | (2006.01) |
| ***C07K 16/22*** | (2006.01) |
| *A61K 39/00* | (2006.01) |

(52) U.S. Cl.

CPC .......... *C07K 16/2863* (2013.01); *C07K 16/22* (2013.01); *A61K 2039/505* (2013.01); *C07K 2317/21* (2013.01); *C07K 2317/24* (2013.01); *C07K 2317/31* (2013.01); *C07K 2317/33* (2013.01); *C07K 2317/34* (2013.01); *C07K 2317/51* (2013.01); *C07K 2317/565* (2013.01); *C07K 2317/622* (2013.01); *C07K 2317/73* (2013.01); *C07K 2317/76* (2013.01); *C07K 2317/92* (2013.01); *C07K 2319/00* (2013.01)

(58) Field of Classification Search

None

See application file for complete search history.

(56) References Cited

U.S. PATENT DOCUMENTS

| | | | | |
|---|---|---|---|---|
| 8,268,314 | B2 * | 9/2012 | Baehner | A61P 19/02 424/136.1 |
| 8,703,130 | B2 | 4/2014 | Baehner et al. | |
| 9,394,367 | B2 | 7/2016 | Cheong et al. | |
| 9,556,275 | B2 * | 1/2017 | Jeong | A61P 3/00 |
| 10,047,154 | B2 * | 8/2018 | Kim | A61P 35/00 |
| 2009/0304694 | A1 | 12/2009 | Oliner et al. | |
| 2010/0256339 | A1 | 10/2010 | Bossenmaier et al. | |
| 2013/0089557 | A1 | 4/2013 | Cheong et al. | |
| 2013/0129722 | A1 | 5/2013 | Lowy et al. | |
| 2013/0156772 | A1 | 6/2013 | Bossenmaier et al. | |
| 2013/0273054 | A1 | 10/2013 | Bossenmaier et al. | |

FOREIGN PATENT DOCUMENTS

| | | | |
|---|---|---|---|
| EP | 2344537 | B1 | 7/2011 |
| KR | 2008-0100810 | A | 11/2008 |
| KR | 2011-0055726 | A | 5/2011 |
| KR | 2011-0126748 | A | 11/2011 |
| KR | 2012-0130658 | A | 12/2012 |
| KR | 10-2013-0036993 | A | 3/2013 |
| KR | 2015-0001110 | A | 1/2015 |
| WO | WO 2004/003019 | A2 | 1/2004 |

OTHER PUBLICATIONS

Mariuzza (Annu. Rev. Biophys. Biophys. Chem., 16: 139-159, 1987).*

McCarthy et al. (J. Immunol. Methods, 251(1-2): 137-149, 2001).*

Lin et al. (African Journal of Biotechnology, 10(79):18294-18302, 2011).*

Augustin et al.,"Control of vascular morphogenesis and homeostatsis through the angiopoietin-Tie system", *Nature Reviews Molecular Cell Biology,* 10:165-77 (2009).

Casset et al., "A peptide mimetic of an anti-CD4 monoclonal antibody by rational design", *Biochemical Biophysical Research Communications,* 307: 198-205 (2003).

Chen et al., "Selection and Analysis of an Optimized Anti-VEGF Antibody: Crystal Structure of an Affinity-matured Fab in Complex with Antigen", *J. Mol. Biol.,* 293:865-881 (1999).

De Pascalis et al., "Grafting of 'Abbreviated' Complimentary-Determining Regions Containing Specificity-Dtermining Residues Essential for Ligand Contact to Engineer a Less Immunogenic Humanized Monoclonal Antibody", *The Journal of Immunology,* 169:3076-3084 (2002).

Gherardi et al., "Targeting MET in cancer: rationale and progress", *Nature Reviews Cancer,* 12: 89-103 (2012).

Hanahan, "Signaling Vascular Morphogenesis and Maintenance", *Science,* 277: 48-50 (1997).

Hara et al. "Hypoxia enhances c-Met/HGF receptor expression and signaling by activating HIF-1α in human salivary gland cancer cells", *Oral Oncology,* 42: 593-598 (2006).

Holm et al., "Functional mapping and single chain construction of the anti-cytokeratin 8 monoclonal antibody TS1", *Molecular Immunology,* 44: 1075:1084 (2007).

(Continued)

*Primary Examiner* — Nelson B Moseley, II

(74) *Attorney, Agent, or Firm* — Cantor Colburn LLP

(57) ABSTRACT

An anti-c-Met/anti-Ang2 bispecific antibody, a composition including the anti-c-Met/anti-Ang2 bispecific antibody, and a method of preventing and/or treating a cancer in a subject including administering the anti-c-Met/anti-Ang2 bispecific antibody to the subject.

5 Claims, 5 Drawing Sheets

Specification includes a Sequence Listing.

(56) References Cited

OTHER PUBLICATIONS

Hwang-Bo et al. "Recombinant canstatin inhibits angiopoietin-1-induced angiogenesis and lymphangiogenesis," *International Journal of Cancer,* 131, 298-309 (2012).
Kumar et al., Molecular Cloning and Expression of the Fabs of Human Autoantibodies in *Escherichia coli, Journal Biological Chemistry,* 275: 35129-35136 (2000).
MacCallum et al., "Antibody-antigen Interactions: Contact Analysis and Binding Site Topography", *J. Mol. Biol.;* 262: 732-745 (1996).
Maisonpierre et al., "Angiopoietin-2, a Natural Antagonist for Tie2 That Disrupts in vivo Angiogenesis", *Science,* 277: 55-60 (1997).
Rudikoff et al., "Single amino acid substitution altering antigen-binding specificity", *Proc. Nat'l Sci USA,* 79:1979-1983 (1982).
Smith-Gill et al., "Contributions of Immunoglobin Heavy and Light Chains to Antibody Specificity for Lysozyme and Two Haptens", *The Journal of Immunology,* 139(12): 4135-4144 (1987).
Song et al., "Light Chain of Natural Antibody Plays a Dominant Role in Protein Anitgen Binding", *Biochemical Biophysical Research Communications,* 268: 390-394 (2000).
Timens et al. "Pathology of the Lung", *European Respiratory Society Monograph,* vol. 12: 62-64 (2007).
Vajdos et al., "Comprehensive Functional Maps of the Antigen-binding Site of an Anti-ErbB2 Antibody Obtained with Shotgun Scanning Mutagenesis", *J. Mol. Biol.,* 320: 415-428 (2002).
Wang et al. "Vascular endothelial cells facilitated HCC invasion and metastasis through the Akt and NF-kB pathways induced by paracrine cytokines," *Journal of Experimental & Clinical Cancer Research,* 32:51 (2013).
Ward et al., "Binding activities of a repertoire of single immunoglobin variable domains secreted from *Escherichia coli", Nature,* 341: 544-546 (1989).
Wu et al., "Humanization of a Murine Monoclonal Antibody by Simulataneous Optimization of Framework and CDR Residues", *J. Mol. Biol.,* 294: 151-162 (1999).
R&D Systems Product Data Sheet for (recombinant c-Met ectodomain_IgG_Fc fusion); pp. 1-2; Oct. 12, 2015.
Notice of Allowance in Korean Patent Application No. 10-2013-017624 dated Aug. 26, 2020.
U.S. Appl. No. 14/556,911, filed Dec. 1, 2014.

* cited by examiner

ANTI-C-MET/ANTI-ANG2 BISPECIFIC ANTIBODY

CROSS-REFERENCE TO RELATED APPLICATIONS

This application is a divisional of U.S. patent application Ser. No. 14/556,911 filed on Dec. 1, 2014, which claims the benefit of Korean Patent Application No. 10-2013-0147624, filed on Nov. 29, 2013, the entire disclosure of which is hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: One 195,840 byte ASCII (Text) file named "728343 ST25.TXT_revised" created Apr. 25, 2017.

BACKGROUND OF THE INVENTION

1. Field

Provided is an anti-c-Met/anti-Ang2 bispecific antibody, a composition including the anti-c-Met/anti-Ang2 bispecific antibody, and a method of preventing and/or treating a cancer in a subject including administering the anti-c-Met/anti-Ang2 bispecific antibody to the subject.

2. Description of the Related Art

Angiopoietin2 (Ang2) is an antagonistic ligand of receptor Tie2 present in vascular endothelial cell (Nat Rev Mol Cell Biol. 2009 March; 10(3):165-77), and competes with Angiopoietin1 (Ang1) which is an agonist of Tie2 for binding to Tie2, thereby inhibiting the signal transduction by Tie2 (Science. 1997 Jul. 4; 277(5322):55-60). Therefore, Ang2 inhibits Ang1-Tie2 signal transduction for maintaining stability of vascular endothelial cells, leading to stimulation of angiogenesis by dynamic rearrangement of blood vessels (Science. 1997 Jul. 4; 277(5322):48-50). It is known from many preclinical studies that since the angiogenesis process is essential to cancer growth, the inhibition of the Tie2-dependent Ang2 functions can lead to the inhibition of angiogenesis, thereby preventing additional growth of cancer (J Natl. Cancer Inst. 2012 Mar. 21; 104(6):461-75). There have been many attempts to prevent cancer using an Ang2 specific antibody by many global pharmaceutical companies, such as Regeneron, Astrazeneca, Amgen, and the like. However, the recent studies have suggested that when a cancer cell is treated with an angiogenesis inhibitor, a mechanism for avoiding the sudden oxygen deficiency condition is activated in the cancer cell, which can stimulate cancer metastasis (Nat. Rev. Clin. Oncol. 2011 Mar. 1; 8(4):210-21) even in the absence of angiogenesis. Therefore, to avoid such serious side effects of angiogenesis inhibitors, it is necessary to inhibit functions of cancer metastasis-related proteins as well.

c-Met is a representative receptor tyrosine kinase (RTK) present on certain cell surfaces. c-Met binds to its ligand, Hepatocyte Growth Factor/Scattering Factor (HGF/SF), to promote intracellular signal transduction, thereby stimulating cell growth, and it is overexpressed in many cancer cells, thereby widely relating to cancer occurrence, cancer metastasis, cancer cell migration, cancer cell invasion, and angiogenesis. In addition, c-Met is a representative early protein of cancer metastasis, because c-Met signaling through HGF/SF weakens cell-cell contact in almost all types of epithelial tumors, leading to scattering. (Nat Rev Cancer. 2012 Jan. 24; 12(2):89-103). In particular, hypoxia-response elements are present at the upstream of c-Met gene, and the expression of the gene is increased under oxygen deficient conditions (Oral Oncol. 2006 July; 42(6):593-8).

Therefore, simultaneous inhibition of Ang2 and c-Met may lead to more effective inhibition of cancer cell growth and metastasis, and thus, it is needed to develop a drug that simultaneously targets both Ang2 and c-Met.

BRIEF SUMMARY OF THE INVENTION

One embodiment provides an anti-c-Met/anti-Ang2 bispecific antibody including (a) an anti-c-Met antibody or an antigen-binding fragment thereof and (b) an anti-Ang2 antibody or an antigen-binding fragment thereof.

The anti-c-Met antibody or an antigen-binding fragment thereof may be an antibody or an antigen-binding fragment thereof which specifically binds to an epitope including or consisting essentially of 5 or more consecutive amino acids in SEMA domain of c-Met protein; and the anti-Ang2 antibody or an antigen-binding fragment thereof may be an antibody or an antigen-binding fragment thereof which specifically binds to (1) at least one amino acid residue selected from the group consisting of amino acid residues exposed to the outside of loop 1, loop 2, and loop 3 of human Ang2 on its tertiary structure or (2) an amino acid sequence region including about 2 to about 20 consecutive amino acids on the tertiary structure of human Ang2 including the at the least one amino acid residue.

Another embodiment provides a pharmaceutical composition including the anti-c-Met/anti-Ang2 bispecific antibody.

Another embodiment provides a method of preventing and/or treating a cancer in a subject including administering the anti-c-Met/anti-Ang2 bispecific antibody to the subject.

DETAILED DESCRIPTION OF THE INVENTION

Figure 1:
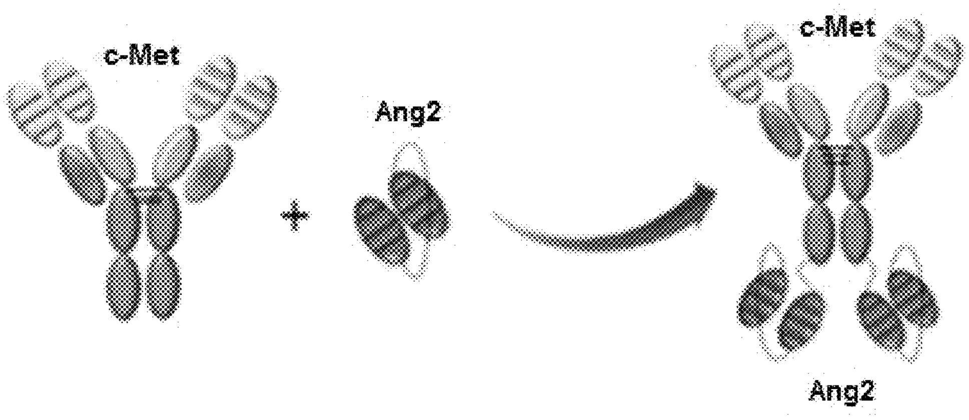
FIG. 1 illustrates is a schematic showing a structure of an anti-c-Met/anti-Ang2 bispecific antibody according to an embodiment.

The pre-existing targeting drugs recognizing only Ang2 in cancer cells often induces over-expression and mutation of c-Met in a cancer cell thereby making the cancer cell to acquire a resistance thereto, leading to decreasing the therapeutic effect thereof. A bispecific antibody simultaneously recognizing c-Met and Ang2 can block a signal transduction by c-Met in a cancer cell, thereby preventing the generation of a drug resistance in a subject, and thus, it can exhibit an excellent cancer cell inhibitory effect even in a cancer cell having a drug resistance.

An embodiment provides an anti-c-Met/anti-Ang2 bispecific antibody including (a) an anti-c-Met antibody or an antigen-binding fragment thereof and (b) an anti-Ang2 antibody or an antigen-binding fragment thereof. The bispecific antibody can simultaneously recognize and bind to c-Met and Ang2, and inhibit the functions thereof, thereby exhibiting synergistic anticancer effects.

As used herein, the term "antibody" refers to all substance generated by an antigen stimulation in immune system, and has no specific limitation in its type. The antibody may include animal antibodies, chimeric antibodies, humanized antibodies, or human antibodies. In addition, the antibody may cover any antigen-binding fragment possessing antigen binding capacity. The term "complementarity-determining regions (CDR)" may refer to a part of a variable region of an antibody, which allows a binding specificity to a specific antigen. The term "antigen-binding fragment" may refer to any antibody fragment including at least one the complementarity-determining region, and for example, it may be selected from the group consisting of scFv, $(scFv)_2$, scFv-Fc, Fab, Fab', and $F(ab')_2$.

In the following description for the anti-c-Met antibody or an antigen-binding fragment thereof and the anti-Ang2 antibody or an antigen-binding fragment thereof, the regions except for heavy chain CDRs and light chain CDRs, or a heavy chain variable region and a light chain variable region may be originated (obtained) from any subtype of immunoglobulin (e.g., IgA, IgD, IgE, IgG (IgG1, IgG2, IgG3, IgG4), IgM, etc.), and for example, may be originated (obtained) from a light chain constant region and/or a heavy chain constant region of any subtype of immunoglobulin.

"c-Met" or "c-Met protein", a target of a bispecific antibody to be provided in one embodiment, refers to a receptor tyrosine kinase (RTK) which binds hepatocyte growth factor (HGF). c-Met may be derived (obtained) from any species, particularly a mammal, for instance, primates such as human c-Met (e.g., NP_000236), monkey c-Met (e.g., *Macaca mulatta*, NP_001162100), or rodents such as mouse c-Met (e.g., NP_032617.2), rat c-Met (e.g., NP_113705.1), or the like. The c-Met protein may include a polypeptide encoded by the nucleotide sequence identified as GenBank Accession Number NM_000245, a polypeptide having the amino acid sequence identified as GenBank Accession Number NP_000236 or extracellular domains thereof. The receptor tyrosine kinase c-Met participates in various biological processes, such as cancer incidence, metastasis, migration of cancer cell, invasion of cancer cell, angiogenesis, and the like.

Ang2, another target of a bispecific antibody to be provided in one embodiment, is closely related to angiogenesis. It is a soluble ligand present in blood, and it is widely involved in angiogenesis, metastasis, and cancer cell invasion. The Ang2 may be derived (obtained) from mammals including primates such as humans and monkeys and rodents such as rats and mice and for example, it may be selected from the group consisting of a human Ang2 (e.g., NCBI Accession #O15123), a monkey Ang2 (e.g., NCBI Accession No. Q8MIK6 etc.), a mouse Ang2 (NCBI Accession #NP_031452, Accession #O35608, etc.), a rat Ang2 (e.g., NCBI Accession No. O35462, etc.), and any combination thereof.

The anti-c-Met/anti-Ang2 bispecific antibody can inhibit the binding between Ang2 and Tie-2 receptor by competing with Tie2 in binding to Ang2, and for example, it may inhibit binding between Ang2 and Tie2 receptor by recognizing and/or binding to a binding site of Ang2 for binding to Tie2 receptor. The anti-Ang2 antibody or an antigen-binding fragment thereof may recognize human Ang2 which widely relates to angiogenesis, cancer metastasis, and cancer cell invasion, and inhibits binding of Ang2 to its receptor, Tie-2 receptor, thereby inhibiting angiogenesis, cancer generation and cancer metastasis, and exhibiting treating and/or preventing effects on a disease associated with over-activation and/or over-expression of Ang2.

Furthermore, the anti-Ang2 antibody or an antigen-binding fragment thereof may further inhibit binding between Ang2 and integrin. Integrin is a typical protein which mediates cell adhesion and has a heterodimer structure including an alpha ($\alpha$) subunit and a beta ($\beta$) subunit. In mammals, 18 types of alpha subunits and 8 types of beta subunits have been identified. The integrin may be derived from mammals including primates such as humans and monkeys and rodents such as mice and rats and for example, it may be a human integrin, a monkey integrin, a mouse integrin and a rat integrin, but is not limited thereto. In each and every species, 24 types of integrins are known and amino acid sequences thereof have been well identified such that they are clearly known those who have ordinary knowledge in the art For example, the integrin may be a human integrin and typical human integrin types may include, but not limited to, alpha5beta1 ($\alpha5\beta1$) ($\alpha5$: NCBI Accession No. P08648, ($\beta1$: NCBI Accession No. P05556), alphaVbeta1 ($\alpha V\beta1$) ($\alpha V$: NCBI Accession No. P06756, $\beta1$: NCBI Accession No. P05556), and alphaVbeta3 ($\alpha V\beta3$) ($\alpha V$: NCBI Accession No. P06756, $\beta3$: NCBI Accession No. P05106).

As described above, in addition to the inhibitory effect on the binding of Ang2 and Tie2 receptor, the anti-Ang2 antibody or an antigen-binding fragment thereof further inhibits the binding between Ang2 and integrin that is another protein involved in cancer cell growth and/or metastasis, thereby having more increased inhibition effects on the cancer cell growth and/or metastasis, and being capable of exhibiting such inhibition effects even in a cell where Tie2 is nor expressed.

The anti-Ang2 antibody or an antigen-binding fragment thereof used in an embodiment may be described as follows.

The anti-Ang2 antibody or an antigen-binding fragment thereof may recognize all or part (for example, at least one amino acid selected from the group consisting of the amino acid residue regions exposed to the outside of each loop) of the regions consisting of loop 1 (a region covering from $417^{th}$ to $434^{th}$ amino acids of SEQ ID NO: 172), loop 2 (a region covering from $447^{th}$ to $454^{th}$ amino acids of SEQ ID NO: 172), and loop 3 (a region covering from $460^{th}$ to $468^{th}$ amino acids of SEQ ID NO: 172) of human Ang2 (hAng2; SEQ ID NO: 172; Accession #O15123), or an amino acid sequence region including about 2 to about 20, about 2 to about 15, about 2 to about 10, or about 2 to about 5 consecutive amino acids within SEQ ID NO: 172 including at least one exposed amino acid residue of loop 1, loop 2, or loop 3 of SEQ ID NO: 172, as an epitope, or specifically bind thereto. An "exposed" amino acid is an amino acid that is exposed to solution and available for binding when a protein (e.g., Ang2) is in its native conformation in a biological medium or other solution under physiological conditions (e.g., physiological pH, isotonicity, temperature, etc.)

For example, the anti-Ang2 antibody or an antigen-binding fragment thereof may recognize at least one amino acid residue selected from the group consisting of I434 positioned at loop 1, A449 and P452 positioned at loop 2, N467 positioned at loop 3 of human Ang2, and any combination thereof, or an amino acid sequence region including about 2 to about 20, about 2 to about 15, about 2 to about 10, or about 2 to about 5 consecutive amino acids including at least one of the above-described amino acid residues from loop 1, 2, or 3 as an epitope and/or specifically bind thereto. In one embodiment, the anti-Ang2 antibody or an antigen-binding fragment thereof may recognize an epitope comprising at least one amino acid residue selected from the group consisting of I434 positioned at loop 1, A449 and P452 positioned at loop 2, and N467 positioned at loop 3 of human Ang2, or specifically bind to this portion.

[Ang2 (SEQ ID NO: 172; loop 1, loop 2 and loop 3 are underlined respectively in order and each epitope is marked in bold and italic letters)]

MWQIVFFTLS CDLVLAAAYN NFRKSMDSIG KKQYQVQHGS

CSYTFLLPEM DNCRSSSSPY VSNAVQRDAP LEYDDSVQRL

QVLENIMENN TQWLMKLENY IQDNMKKEMV EIQQNAVQNQ

TAVMIEIGTN LLNQTAEQTR KLTDVEAQVL NQTTRLELQL

LEHSLSTNKL EKQILDQTSE INKLQDKNSF LEKKVLAMED

KHIIQLQSIK EEKDQLQVLV SKQNSIIEEL EKKIVTATVN

NSVLQKQQHD LMETVNNLLT MMSTSNSAKD PTVAKEEQIS

FRDCAEVFKS GHTTNGIYTL TFPNSTEEIK AYCDMEAGGG

GWTIIQRRED GSVDFQRTWK EYKVGFGNPS GEYWLGNEFV

SQLTNQQRYV LKIHLKDWEG NEAYSLYEHF YLSSEELNYR

IHLKGLTGTA GKISSISQPG NDFSTKDGDN DKC*I*CKCSQM

LTGGWWFD*A*C G*P*SNLNGMYY PQRQNT*N*KFN GIKWYYWKGS

GYSLKATTMM IRPADF

The above epitope sites are exposed amino acid residues positioned at loop 1, loop 2, or loop 3 of the three dimensional structure of Ang2, and they directly participate in binding with a Tie2 receptor or they are positioned by being included in the binding site with the Tie2 receptor or neighboring thereupon (see FIG. 1). Accordingly, the anti-Ang2 antibody or an antigen-binding fragment thereof recognizing and binding to the above at least one epitope competes with the Tie2 receptor in binding to Ang2 and thus, inhibits binding between Ang2 and the Tie2 receptor.

The term "consecutive amino acid" may include amino acids which are adjacent to one another on the secondary or tertiary structure of a protein as well as amino acids which are continuous on their primary amino acid sequences. Accordingly, the "consecutive amino acid residues" as used herein may refer to contiguous amino acid residues on the primary, secondary, or tertiary structure of a protein.

Embodiments of the invention also include an antibody or an antigen-binding fragment thereof that competes with the anti-Ang2 antibody for binding to Ang2, or that competes with the Tie2 receptor in binding to Ang2, and can inhibit binding between Ang2 and the Tie2 receptor. This competitive-binding antibody may be an antibody recognizing a site adjacent to the aforementioned epitopes on its three dimensional structure of Ang2 as an epitope. The competitive-binding antibody may have a binding affinity (Kd) of about 0.001 to about 10 nM, about 0.01 to about 1 nM, or about 0.1 to about 0.8 nM.

Therefore, the anti-Ang2 antibody or an antigen-binding fragment thereof may be at least one selected from the group consisting of an antibody or an antigen-binding fragment thereof recognizing and/or specifically binding to the aforementioned epitope, and an antibody competing therewith for binding to Ang2 or an antigen-binding fragment thereof.

In a particular embodiment, the anti-Ang2 antibody or an antigen-binding fragment thereof may include or consist essentially of, as a heavy chain complementarity determining region (CDR), at least one selected from the group consisting of a polypeptide (CDR-H1) including the amino acid sequence of SEQ ID NO: 151, a polypeptide (CDR-H2) including the amino acid sequence of SEQ ID NO: 152 and a polypeptide (CDR-H3) including an amino acid sequence selected from the group consisting of SEQ ID NOs: 122 to 129, for example, an amino acid sequence selected from the group consisting of SEQ ID NOs: 122 to 127:

(SEQ ID NO: 151)

$X_1$-Y-$X_2$-M-S wherein, $X_1$ is aspartic acid (D), serine (S), or asparagine (N), for example, aspartic acid (D) or asparagine (N), and $X_2$ is alanine (A), aspartic acid (D), or tyrosine (Y); and (SEQ ID NO: 152)

$X_3$-I-$X_4$-$X_5$-$X_6$-$X_7$-$X_8$-$X_9$-$X_{10}$-Y-Y-A-D-S-V-K-G wherein, $X_3$ is alanine (A), glycine (G), leucine (L), or serine (S), for example, alanine (A), glycine (G), or serine (S), $X_4$ is tyrosine (Y) or serine (S), $X_5$ is proline (P), histidine (H), or serine (S), $X_6$ is aspartic acid (D), glycine (G), or serine (S), $X_7$ is serine (S), glycine (G), or aspartic acid (D), $X_8$ is glycine (G) or serine (S), $X_9$ is asparagine (N) or serine (S), and $X_{10}$ is lysine (K), isoleucine (I), or threonine (T).

The anti-Ang2 antibody or an antigen-binding fragment thereof may include or consist essentially of, as a light chain complementarity determining region (CDR), at least one selected from the group consisting of a polypeptide (CDR-L1) including the amino acid sequence of SEQ ID NO: 153, a polypeptide (CDR-L2) including the amino acid sequence of SEQ ID NO: 154, and a polypeptide (CDR-L3) including the amino acid sequence of SEQ ID NO: 155:

(SEQ ID NO: 153)
$X_{11}$-G-S-S-S-N-I-G-$X_{12}$-N-$X_{13}$-V-$X_{14}$ wherein,
$X_{11}$ is serine (S) or threonine (T),
$X_{12}$ is asparagine (N) or serine (S),
$X_{13}$ is alanine (A), tyrosine (Y), or aspartic acid (D), and
$X_{14}$ is asparagine (N), serine (S), threonine (T), or tyrosine (Y);

(SEQ ID NO: 154)
$X_{15}$-$X_{16}$-$X_{17}$-$X_{18}$-R-P-S wherein,
$X_{15}$ is alanine (A) or serine (S),
$X_{16}$ is aspartic acid (D) or asparagine (N),
$X_{17}$ is serine (S) or asparagine (N), for example serine (S), and
$X_{18}$ is asparagine (N), Lysine (K), histidine (H), or glutamine (Q); and (SEQ ID NO: 155)
$X_{19}$-$X_{20}$-W-D-$X_{21}$-S-L-$X_{22}$-$X_{23}$ wherein,
$X_{19}$ is glycine (G) or alanine (A),
$X_{20}$ is serine (S), alanine (A), or threonine (T), for example serine (S) or threonine (T),
$X_{21}$ is tyrosine (Y) or aspartic acid (D), for example, tyrosine (Y),
$X_{22}$ is serine (S) or asparagine (N), for example, serine (S), and
$X_{23}$ is glycine (G) or alanine (A).

In an embodiment, the anti-Ang2 antibody or an antigen-binding fragment thereof may include or consist essentially of the above heavy chain complementarity determining regions, light chain complementarity determining regions, or any combination thereof.

More particularly, the anti-Ang2 antibody or an antigen-binding fragment thereof may include or consist essentially of:

at least one heavy chain complementarity determining region selected from the group consisting of a polypeptide (CDR-H1) including the amino acid sequence of SEQ ID NO: 151, a polypeptide (CDR-H2) including the amino acid sequence of SEQ ID NO: 152, and a polypeptide (CDR-H3) including an amino acid sequence selected from the group consisting of SEQ ID NOs: 122 to 129, for example, an amino acid sequence selected from the group consisting of SEQ ID NOs: 122 to 127, or a heavy chain variable region including the at least one heavy chain complementarity determining region;

at least one light chain complementarity determining region selected from the group consisting of a polypeptide (CDR-L1) including the amino acid sequence of SEQ ID NO: 153, a polypeptide (CDR-L2) including the amino acid sequence of SEQ ID NO: 154, and a polypeptide (CDR-L3) including the amino acid sequence of SEQ ID NO: 155, or a light chain variable region including the at least one light chain complementarity determining region;

a combination of the at least one heavy chain complementarity determining region and the at least one light chain complementarity determining region; or a combination of the heavy chain variable region and the light chain variable region.

For example, the heavy chain CDR of the anti-Ang2 antibody may include or consist essentially of the amino acid sequence as set forth in following Table 1.

TABLE 1

| Amino acid sequence of heavy chain CDR | | |
|---|---|---|
| CDRH1-KABAT | CDRH2-KABAT | CDRH3-KABAT |
| DYAMS (SEQ ID NO: 109) | AIYPDSGNKYYADSVKG (SEQ ID NO: 115) | ARHSSDPKVKSGYYDDGMDV (SEQ ID NO: 122) |
| DYYMS (SEQ ID NO: 110) | GIYPSGGSTYYADSVKG (SEQ ID NO: 116) | ARDPSTLTYAGFDY (SEQ ID NO: 123) |
| NYAMS (SEQ ID NO: 111) | AISSGGGNIYYADSVKG (SEQ ID NO: 117) | AKSGIQPSPPSMSSAYAMDV (SEQ ID NO: 124) |
| DYAMS (SEQ ID NO: 109) | SIYPDDGNTYYADSVKG (SEQ ID NO: 118) | ARHTSHHTSIDGYYYYGMDG (SEQ ID NO: 125) |
| DYDMS (SEQ ID NO: 112) | SISHGDSNKYYADSVKG (SEQ ID NO: 119) | AKSSGIQESPPTYYYYGMDV (SEQ ID NO: 126) |
| DYAMS (SEQ ID NO: 109) | SIYPDDGNTYYADSVKG (SEQ ID NO: 118) | AKHPVRLNLHPMYYYYGMDV (SEQ ID NO: 127) |
| SYDMS (SEQ ID NO: 113) | LISPDSSSIYYADSVKG (SEQ ID NO: 120) | AKDLISFWRGGFDY (SEQ ID NO: 128) |
| DYDMS (SEQ ID NO: 114) | GISSDDGNTYYADSVKG (SEQ ID NO: 121) | ARPTIDKYTLRGYYSYGMDV (SEQ ID NO: 129) |

In addition, the light chain CDR of the anti-Ang2 antibody may include or consist essentially of the amino acid sequence as set forth in following Table 2.

TABLE 2

| Amino acid sequence of light chain CDR | | |
|---|---|---|
| CDRL1-KABAT | CDRL2-KABAT | CDRL3-KABAT |
| SGSSSNIGNNAVN (SEQ ID NO: 130) | ADSNRPS (SEQ ID NO: 138) | GSWDYSLSG (SEQ ID NO: 145) |
| SGSSSNIGNNYVT (SEQ ID NO: 131) | ADSHRPS (SEQ ID NO: 139) | ATWDYSLSG (SEQ ID NO: 146) |
| SGSSSNIGNNDVY (SEQ ID NO: 132) | ANSHRPS (SEQ ID NO: 140) | GTWDYSLSG (SEQ ID NO: 147) |
| TGSSSNIGNNDVS (SEQ ID NO: 133) | SDSKRPS (SEQ ID NO: 141) | GSWDYSLSG (SEQ ID NO: 145) |
| SGSSSNIGSNAVN (SEQ ID NO: 134) | ADSNRPS (SEQ ID NO: 138) | GSWDYSLSG (SEQ ID NO: 145) |

TABLE 2-continued

| Amino acid sequence of light chain CDR | | |
|---|---|---|
| CDRL1-KABAT | CDRL2-KABAT | CDRL3-KABAT |
| TGSSSNIGNNAVS (SEQ ID NO: 135) | SDSQRPS (SEQ ID NO: 142) | ATWDYSLSA (SEQ ID NO: 148) |
| SGSSSNIGSNYVN (SEQ ID NO: 136) | SDSHRPS (SEQ ID NO: 143) | GAWDDSLSG (SEQ ID NO: 149) |
| TGSSSNIGSNYVS (SEQ ID NO: 137) | SDNKRPS (SEQ ID NO: 144) | GTWDDSLNG (SEQ ID NO: 150) |

In particular, the anti-Ang2 antibody or an antigen-binding fragment thereof may include or consist essentially of:

at least one heavy chain complementarity determining region selected from the group consisting of a polypeptide (CDR-H1) including an amino acid sequence selected from SEQ ID NOs: 109 to 114, for example, an amino acid sequence selected from SEQ ID NOs: 109 to 112, a polypeptide (CDR-H2) including an amino acid sequence selected from SEQ ID NOs: 115 to 121, for example, an amino acid sequence selected from SEQ ID NOs: 115 to 119, and a polypeptide (CDR-H3) including an amino acid sequence selected from the group consisting of SEQ ID NOs: 122 to 129, for example, an amino acid sequence selected from SEQ ID NOs: 122 to 127, or a heavy chain variable region including the at least one heavy chain complementarity determining region;

at least one light chain complementarity determining region selected from the group consisting of a polypeptide (CDR-L1) including an amino acid sequence selected from SEQ ID NOs: 130 to 137, for example, an amino acid sequence selected from SEQ ID NOs: 130 to 135, a polypeptide (CDR-L2) including an amino acid sequence selected from SEQ ID NOs: 138 to 144, for example, an amino acid sequence selected from SEQ ID NOs: 138 to 142, and a polypeptide (CDR-L3) including an amino acid sequence selected from SEQ ID NOs: 145 to 150, for example, an amino acid sequence selected from SEQ ID NOs: 145 to 148, or a light chain variable region including the at least one light chain complementarity determining region;

a combination of the at least one heavy chain complementarity determining region and the at least one light chain complementarity determining region; or a combination of the heavy chain variable region and the light chain variable region.

In the anti-Ang2 antibody or an antigen-binding fragment thereof, the heavy chain variable region may include or consist essentially of an amino acid sequence selected from the group consisting of SEQ ID NOs: 156 to 163, for example an amino acid sequence selected from the group consisting of SEQ ID NOs: 156 to 161, and the light chain variable region may include or consist essentially of an amino acid sequence selected from the group consisting of SEQ ID NOs: 164 to 171, for example an amino acid sequence selected from the group consisting of SEQ ID NOs: 164 to 169.

Accordingly, the anti-Ang2 antibody or an antigen-binding fragment thereof may include or consist essentially of a heavy chain variable region including an amino acid sequence selected from the group consisting of SEQ ID NOs: 156 to 163, for example an amino acid sequence selected from the group consisting of SEQ ID NOs: 156 to 161; a light chain variable region including an amino acid sequence selected from the group consisting of SEQ ID NO: 164 or 171, for example an amino acid sequence selected from the group consisting of SEQ ID NOs: 164 to 169; or a combination of the heavy chain variable region and the light chain variable region.

The amino acid sequences of the heavy chain variable region and the light chain variable region of the anti-Ang2 antibody according to an embodiment are summarized in Table 3:

TABLE 3

| Amino acid sequence of heavy chain variable region | Amino acid sequence of light chain variable region |
|---|---|
| EVQLLESGGGLVQTGGSLRLSCAASGFTFS**DYA**MSWVRQAPGKGLEWVS**AIYPDSGNKYYADSVKG**RFTISRDNSKNTLYLQMNSLRAEDTAVYYC**ARHSSDPKVKSGYYDDGMDV**WGQGTLVAVSS (SEQ ID NO: 156) | QSVLTQPPSASGTPGQRVTISC**SGSSSNIGNNAVN**WYQQLPGTAPKLLIY**ADSNRPSGVPDRFSGSK**SGTSASLAISGLRSEDEADYYC**GSWDYSLSG**YVFGGGTKLTVLG (SEQ ID NO: 164) |
| EVQLLESGGGLVQPGGSLRLSCAASGFTFS**DYYMS**WVRQAPGKGLEWVS**GIYPSGGSTYYADSVKG**RFTISRDNSKNTLYLQMNSLRAEDTAVYYC**ARDPSTLTYAGFDY**WGQGTLVTVSS (SEQ ID NO: 157) | QSVLTQPPSASGTPGQRVTISC**SGSSSNIGNNYVT**WYQQLPGTAPKLLIY**ADSHRPS**GVPDRFSGSKSGTSASLAISGLRSEDEADYYC**ATWDYSLSG**YVFGGGTKLTVLG (SEQ ID NO: 165) |
| EVQLLESGGGLVQPGGSLRLSCAASGFTFS**NYAMS**WVRQAPGKGLEWVS**AISSGGGNIYYADSVKG**RFTISRDNSKNTLYLQMNSLRAEDTAVYYC**AKSGIQPSPPSMSSAYAMDV**WGQGTLVTVSS (SEQ ID NO: 158) | QSVLTQPPSASGTPGQRVTISC**SGSSSNIGNNDVY**WYQQLPGTAPKLLIY**ANSHRPS**GVPDRFSGSKSGTSASLAISGLRSEDEADYYC**GTWDYSLSG**YVFGGGTKLTVLG (SEQ ID NO: 166) |
| EVQLLESGGGLVQPGGSLRLSCAASGFTFS**DYAMS**WVRQAPGKGLEWVS**SIYPDDGNTYYADSVKG**RFTISRDNSKNTLYLQMNSLRAEDTAVYYC**ARHTSHHTSIDGYYYYGMDG**WGQGTLVTVSS (SEQ ID NO: 159) | QSVLTQPPSASGTPGQRVTISC**TGSSSNIGNNDV**SWYQQLPGTAPKLLIY**SDSKRPS**GVPDRFSGSKSGTSASLAISGLRSEDEADYYC**GSWDYSLSG**YVFGGGTKLTVLG (SEQ ID NO: 167) |
| EVQLLESGGGLVQPGGSLRLSCAASGFTFS**DYDMS**WVRQAPGKGLEWVS**SISHGDSNKYYADSV** | QSVLTQPPSASGTPGQRVTISC**SGSSSNIGSNAVN**WYQQLPGTAPKLLIY**ADSNRPS**GVPDRFSGSK |

TABLE 3-continued

| Amino acid sequence of heavy chain variable region | Amino acid sequence of light chain variable region |
|---|---|
| **KG**RFTISRDNSKNTLYLQMNSLRAEDTAVYYC **AKSSGIQESPPTYYYYGMDV**WGQGTLVTVSS (SEQ ID NO: 160) | SGTSASLAISGLRSEDEADYYC**GSWDYSLSG**YV FGGGTKLTVLG (SEQ ID NO: 168) |
| EVQLLESGGGLVQTGGSLRLSCAASGFTFS**DYA MS**WVRQAPGKGLEWVS**SIYPDDGNTYYADSV KG**RFTISRDNSKNTLYLQMNSLRAEDTAVYYC **AKHPVRLNLHPMYYYYGMDV**WGQGTLVTVS S (SEQ ID NO: 161) | QSVLTQPPSASGTPGQRVTISC**TGSSSNIGNNAV S**WYQQLPGTAPKLLIY**SDSQRPS**GVPDRFSGSK SGTSASLAISGLRSEDEADYYC**ATWDYSLSA**YV FGGGTKLTVLG (SEQ ID NO: 169) |
| EVQLLESGGGLVQPGGSLRLSCAASGFTFS**SYD MS**WVRQAPGKGLEWVS**LISPDSSSIYYADSVK G**RFTISRDNSKNTLYLQMNSLRAEDTAVYYC**A KDLISFWRGGFDY**WGQGTLVTVSS (SEQ ID NO: 162) | QSVLTQPPSASGTPGQRVTISC**SGSSSNIGSNYV N**WYQQLPGTAPKLLIY**ADSNRPS**GVPDRFSGSK SGTSASLAISGLRSEDEADYYC**GSWDYSLSG**YV FGGGTKLTVLG (SEQ ID NO: 170) |
| EVQLLESGGGLVQPGGSLRLSCAASGFTFS**DYD MS**WVRQAPGKGLEWVS**GISSDDGNTYYADSV KG**RFTISRDNSKNTLYLQMNSLRAEDTAVYYC **ARPTIDKYTLRGYYSYGMDV**WGQGTLVTVSS (SEQ ID NO: 163) | QSVLTQPPSASGTPGQRVTISC**TGSSSNIGSNYV S**WYQQLPGTAPKLLIY**SDNKRPS**GVPDRFSGSK SGTSASLAISGLRSEDEADYYC**GTWDDSLNGY** VFGGGTKLTVLG (SEQ ID NO: 171) |

In another embodiment, the anti-Ang2 antibody or an antigen-binding fragment thereof may include or consist essentially of:

at least one heavy chain complementarity determining region selected from the group consisting of a polypeptide (CDR-H1) including an amino acid sequence of SEQ ID NO: 113 or 114; a polypeptide (CDR-H2) including an amino acid sequence of SEQ ID NO: 120 or 121, and a polypeptide (CDR-H3) including an amino acid sequence of SEQ ID NO: 128 or 129, or a heavy chain variable region including the at least one heavy chain complementarity determining region;

at least one light chain complementarity determining region selected from the group consisting of a polypeptide (CDR-L1) including an amino acid sequence of SEQ ID NO: 136 or 137, a polypeptide (CDR-L2) including an amino acid sequence of SEQ ID NO: 143 or 144, and a polypeptide (CDR-L3) including an amino acid sequence of SEQ ID NO: 149 or to 150, or a light chain variable region including the at least one light chain complementarity determining region;

a combination of the at least one heavy chain complementarity determining region and the at least one light chain complementarity determining region; or a combination of the heavy chain variable region and the light chain variable region.

In the anti-Ang2 antibody or an antigen-binding fragment thereof, the heavy chain variable region may include an amino acid sequence of SEQ ID NO: 162 or 163, and the light chain variable region may include an amino acid sequence of SEQ ID NO: 170 or 171. Accordingly, the anti-Ang2 antibody or an antigen-binding fragment thereof may include a heavy chain variable region including an amino acid sequence of SEQ ID NO: 162 or 163; a light chain variable region including an amino acid sequence of SEQ ID NO: 170 or 171; or a combination of the heavy chain variable region and the light chain variable region.

The anti-c-Met antibody may recognize a specific region of c-Met, e.g., a specific region in the SEMA domain, as an epitope. It may be any antibody or antigen-binding fragment that acts on c-Met to induce c-Met intracellular internalization and degradation.

c-Met, a receptor for hepatocyte growth factor (HGF), may be divided into three portions: extracellular, transmembrane, and intracellular. The extracellular portion is composed of an α-subunit and a β-subunit which are linked to each other through a disulfide bond, and includes a SEMA domain responsible for binding HGF, a plexin-semaphorins-integrin identity/homology domain (PSI domain) and an immunoglobulin-like fold shared by plexins and transcriptional factors domain (IPT domain). The SEMA domain of c-Met protein may have the amino acid sequence of SEQ ID NO: 79, and is an extracellular domain that functions to bind HGF. A specific region of the SEMA domain, that is, a region having the amino acid sequence of SEQ ID NO: 71, which corresponds to a range from amino acid residues 106 to 124 of the amino acid sequence of the SEMA domain (SEQ ID NO: 79), is a loop region between the second and the third beta propellers within the epitopes of the SEMA domain. This region acts as an epitope for the anti-c-Met antibody provided in the present invention.

The term "epitope," as used herein, refers to an antigenic determinant, a part of an antigen recognized by an antibody. In one embodiment, the epitope may be a region including 5 or more contiguous (consecutive on primary, secondary (two-dimensional), or tertiary (three-dimensional) structure) amino acid residues within the SEMA domain (SEQ ID NO: 79) of c-Met protein, for instance, 5 to 19 contiguous amino acid residues within the amino acid sequence of SEQ ID NO: 71. For example, the epitope may be a polypeptide having 5 to 19 contiguous amino acids selected from among partial combinations of the amino acid sequence of SEQ ID NO: 71, wherein the polypeptide includes the amino sequence of SEQ ID NO: 73 (EEPSQ) serving as an essential element for the epitope. For example, the epitope may be a polypeptide including, consisting essentially of, or consisting of the amino acid sequence of SEQ ID NO: 71, SEQ ID NO: 72, or SEQ ID NO: 73.

The epitope having the amino acid sequence of SEQ ID NO: 72 corresponds to the outermost part of the loop between the second and third beta propellers within the SEMA domain of a c-Met protein. The epitope having the amino acid sequence of SEQ ID NO: 73 is a site to which the antibody or antigen-binding fragment according to one embodiment most specifically binds.

Thus, the anti-c-Met antibody may specifically bind to an epitope which includes 5 to 19 contiguous amino acids selected from among partial combinations of the amino acid sequence of SEQ ID NO: 71, including SEQ ID NO: 73 as an essential element. For example, the anti-c-Met antibody may specifically bind to an epitope including the amino acid sequence of SEQ ID NO: 71, SEQ ID NO: 72, or SEQ ID NO: 73.

In one embodiment, the anti-c-Met antibody or an antigen-binding fragment thereof may include:

at least one heavy chain complementarity determining region (CDR) selected from the group consisting of (a) a CDR-H1 including the amino acid sequence of SEQ ID NO: 4; (b) a CDR-H2 including the amino acid sequence of SEQ ID NO: 5, SEQ ID NO: 2, or an amino acid sequence including 8-19 consecutive amino acids within SEQ ID NO: 2 including amino acid residues from the $3^{rd}$ to $10^{th}$ positions of SEQ ID NO: 2; and (c) a CDR-H3 including the amino acid sequence of SEQ ID NO: 6, SEQ ID NO: 85, or an amino acid sequence including 6-13 consecutive amino acids within SEQ ID NO: 85 including amino acid residues from the $1^{st}$ to $6^{th}$ positions of SEQ ID NO: 85, or a heavy chain variable region including the at least one heavy chain complementarity determining region;

at least one light chain complementarity determining region (CDR) selected from the group consisting of (a) a CDR-L1 including the amino acid sequence of SEQ ID NO: 7, (b) a CDR-L2 including the amino acid sequence of SEQ ID NO: 8, and (c) a CDR-L3 including the amino acid sequence of SEQ ID NO: 9, SEQ ID NO: 15, SEQ ID NO: 86, or an amino acid sequence including 9-17 consecutive amino acids within SEQ ID NO: 89 including amino acid residues from the $1^{st}$ to $9^{th}$ positions of SEQ ID NO: 89, or a light chain variable region including the at least one light chain complementarity determining region;

a combination of the at least one heavy chain complementarity determining region and at least one light chain complementarity determining region; or a combination of the heavy chain variable region and the light chain variable region.

Herein, the amino acid sequences of SEQ ID NOS: 4 to 9 are respectively represented by following Formulas I to VI, below:

Formula I (SEQ ID NO: 4)

$Xaa_1$-$Xaa_2$-Tyr-Tyr-Met-Ser, wherein $Xaa_1$ is absent or Pro or Ser, and $Xaa_2$ is Glu or Asp, Formula II (SEQ ID NO: 5)

Arg-Asn-$Xaa_3$-$Xaa_4$-Asn-Gly-$Xaa_5$-Thr, wherein $Xaa_3$ is Asn or Lys, $Xaa_4$ is Ala or Val, and $Xaa_5$ is Asn or Thr, Formula III (SEQ ID NO: 6)

Asp-Asn-Trp-Leu-$Xaa_6$-Tyr, wherein $Xaa_6$ is Ser or Thr,

Formula IV (SEQ ID NO: 7)

Lys-Ser-Ser-$Xaa_7$-Ser-Leu-Leu-Ala-$Xaa_8$-Gly-Asn-$Xaa_9$-$Xaa_{10}$-Asn-Tyr-Leu-Ala wherein $Xaa_7$ is His, Arg, Gln, or Lys, $Xaa_8$ is Ser or Trp, $Xaa_9$ is His or Gln, and $Xaa_{10}$ is Lys or Asn, Formula V (SEQ ID NO: 8)

Trp-$Xaa_{11}$-Ser-$Xaa_{12}$-Arg-Val-$Xaa_{13}$ wherein $Xaa_{11}$ is Ala or Gly, $Xaa_{12}$ is Thr or Lys, and $Xaa_{13}$ is Ser or Pro, and Formula VI (SEQ ID NO: 9)

$Xaa_{14}$-Gln-Ser-Tyr-Ser-$Xaa_{15}$-Pro-$Xaa_{16}$-Thr wherein $Xaa_{14}$ is Gly, Ala, or Gln, $Xaa_{15}$ is Arg, His, Ser, Ala, Gly, or Lys, and $Xaa_{16}$ is Leu, Tyr, Phe, or Met.

In one embodiment, the CDR-H1 may include an amino acid sequence selected from the group consisting of SEQ ID NO: 1, SEQ ID NO: 22, SEQ ID NO: 23, and SEQ ID NO: 24. The CDR-H2 may include an amino acid sequence selected from the group consisting of SEQ ID NO: 2, SEQ ID NO: 25, and SEQ ID NO: 26. The CDR-H3 may include an amino acid sequence selected from the group consisting of SEQ ID NO: 3, SEQ ID NO: 27, SEQ ID NO: 28, and SEQ ID NO: 85.

The CDR-L1 may include an amino acid sequence selected from the group consisting of SEQ ID NO: 10, SEQ ID NO: 29, SEQ ID NO: 30, SEQ ID NO: 31, SEQ ID NO: 32, SEQ ID NO: 33 and SEQ ID NO: 106. The CDR-L2 may include an amino acid sequence selected from the group consisting of SEQ ID NO: 11, SEQ ID NO: 34, SEQ ID NO: 35, and SEQ ID NO: 36. The CDR-L3 may include an amino acid sequence selected from the group consisting of SEQ ID NO: 12, SEQ ID NO: 13, SEQ ID NO: 14, SEQ ID NO: 15, SEQ ID NO: 16, SEQ ID NO: 37, SEQ ID NO: 86, and SEQ ID NO: 89.

In another embodiment, the antibody or antigen-binding fragment may include a heavy variable region including a polypeptide (CDR-H1) including an amino acid sequence selected from the group consisting of SEQ ID NO: 1, SEQ ID NO: 22, SEQ ID NO: 23, and SEQ ID NO: 24, a polypeptide (CDR-H2) including an amino acid sequence selected from the group consisting of SEQ ID NO: 2, SEQ ID NO: 25, and SEQ ID NO: 26, and a polypeptide (CDR-H3) including an amino acid sequence selected from the group consisting of SEQ ID NO: SEQ ID NO: 3, SEQ ID NO: 27, SEQ ID NO: 28, and SEQ ID NO: 85; and a light variable region including a polypeptide (CDR-L1) including an amino acid sequence selected from the group consisting of SEQ ID NO: 10, SEQ ID NO: 29, SEQ ID NO: 30, SEQ ID NO: 31, SEQ ID NO: 32, SEQ ID NO: 33, and SEQ ID NO: 106, a polypeptide (CDR-L2) including an amino acid sequence selected from the group consisting of SEQ ID NO: 11, SEQ ID NO: 34, SEQ ID NO: 35, and SEQ ID NO: 36, and a polypeptide (CDR-L3) including an amino acid sequence selected from the group consisting of SEQ ID NO: 12, SEQ ID NO: 13, SEQ ID NO: 14, SEQ ID NO: 15, SEQ ID NO: 16, SEQ ID NO: 37, SEQ ID NO: 86, and SEQ ID NO: 89.

In one embodiment, the anti-c-Met antibody or an antigen-binding fragment thereof may be modified by the deletion, insertion, addition, or substitution of at least one amino acid residue on the amino acid sequence of the hinge region so that it exhibit enhanced antigen-binding efficiency. For example, the antibody may include a hinge region having the amino acid sequence of SEQ ID NO: 100(U7-HC6), SEQ ID NO: 101(U6-HC7), SEQ ID NO: 102(U3-HC9), SEQ ID NO: 103(U6-HC8), or SEQ ID NO: 104(U8-HC5), or a hinge region having the amino acid sequence of SEQ ID NO: 105 (non-modified human hinge). In particular, the hinge region includes the amino acid sequence of SEQ ID NO: 100 or SEQ ID NO: 101.

In one embodiment, the anti-c-Met antibody or antigen-binding fragment may have a heavy chain variable region including the amino acid sequence of SEQ ID NO: 17, SEQ ID NO: 74, SEQ ID NO: 87, SEQ ID NO: 90, SEQ ID NO: 91, SEQ ID NO: 92, SEQ ID NO: 93, or SEQ ID NO: 94; a light chain variable region including the amino acid sequence of SEQ ID NO: 18, SEQ ID NO: 19, SEQ ID NO: 20, SEQ ID NO: 21, SEQ ID NO: 75, SEQ ID NO: 88, SEQ ID NO: 95, SEQ ID NO: 96, SEQ ID NO: 97, SEQ ID NO: 98, SEQ ID NO: 99, or SEQ ID NO: 107; or a combination of the heavy chain variable region and the light chain variable region.

In one embodiment, the anti-c-Met antibody may be a monoclonal antibody. The monoclonal antibody may be produced by the hybridoma cell line deposited with the Korean Cell Line Research Foundation, an international depository authority located at Yungun-Dong, Jongno-Gu, Seoul, Korea, on Oct. 6, 2009, under Accession No. KCLRF-BP-00220, which binds specifically to the extracellular region of c-Met protein (refer to Korean Patent Publication No. 2011-0047698, the disclosure of which is incorporated in its entirety herein by reference). The anti-c-Met antibody may include all the antibodies defined in Korean Patent Publication No. 2011-0047698.

In the anti-c-Met antibody or an antigen-binding fragment thereof and the anti-Ang2 antibody or an antigen-binding fragment thereof, the portion of the light chain and the heavy chain portion excluding the CDRs, the light chain variable region, and the heavy chain variable region as defined above, that is the light chain constant region and the heavy chain constant region, may be those from any subtype of immunoglobulin (e.g., IgA, IgD, IgE, IgG (IgG1, IgG2, IgG3, IgG4), IgM, etc.).

By way of further example, the anti-c-Met antibody or the antibody fragment may include:

a heavy chain including the amino acid sequence selected from the group consisting of the amino acid sequence of SEQ ID NO: 62 (wherein the amino acid sequence from amino acid residues from the $1^{st}$ to $17^{th}$ positions is a signal peptide), or the amino acid sequence from the $18^{th}$ to $462^{nd}$ positions of SEQ ID NO: 62, the amino acid sequence of SEQ ID NO: 64 (wherein the amino acid sequence from the $1^{st}$ to $17^{th}$ positions is a signal peptide), the amino acid sequence from the $18^{th}$ to $461^{st}$ positions of SEQ ID NO: 64, the amino acid sequence of SEQ ID NO: 66 (wherein the amino acid sequence from the $1^{st}$ to $17^{th}$ positions is a signal peptide), and the amino acid sequence from the $18^{th}$ to $460^{th}$ positions of SEQ ID NO: 66; and a light chain including the amino acid sequence selected from the group consisting of the amino acid sequence of SEQ ID NO: 68 (wherein the amino acid sequence from the $1^{st}$ to $20^{th}$ positions is a signal peptide), the amino acid sequence from the $21^{st}$ to $240^{th}$ positions of SEQ ID NO: 68, the amino acid sequence of SEQ ID NO: 70 (wherein the amino acid sequence from the $1^{st}$ to $20^{th}$ positions is a signal peptide), the amino acid sequence from the $21^{st}$ to $240^{th}$ positions of SEQ ID NO: 70, and the amino acid sequence of SEQ ID NO: 108.

For example, the anti-c-Met antibody may be selected from the group consisting of:

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 108;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 108; and an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 108.

The polypeptide of SEQ ID NO: 70 is a light chain including human kappa (κ) constant region, and the polypeptide with the amino acid sequence of SEQ ID NO: 68 is a polypeptide obtained by replacing histidine at position 62 (corresponding to position 36 of SEQ ID NO: 68 according to kabat numbering) of the polypeptide with the amino acid sequence of SEQ ID NO: 70 with tyrosine. The production yield of the antibodies may be increased by the replacement. The polypeptide with the amino acid sequence of SEQ ID NO: 108 is a polypeptide obtained by replacing serine at position 32 (position 27e according to kabat numbering in the amino acid sequence from amino acid residues 21 to 240 of SEQ ID NO: 68; positioned within CDR-L1) with tryptophan. By such replacement, antibodies and antibody fragments including such sequences exhibits increased activities, such as c-Met biding affinity, c-Met degradation activity, Akt phosphorylation inhibition, and the like.

In another embodiment, the anti-c-Met antibody may include a light chain complementarity determining region including the amino acid sequence of SEQ ID NO: 106, a light chain variable region including the amino acid sequence of SEQ ID NO: 107, or a light chain including the amino acid sequence of SEQ ID NO: 108.

In another embodiment, the anti-c-Met antibody may include a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 68 or the amino acid sequence from the $21^{st}$ to $240^{th}$ positions of SEQ ID NO: 68.

The following descriptions may be applied to both the anti-c-Met antibodies or fragments thereof and the anti-Ang2 antibodies or fragments thereof described herein.

Animal-derived antibodies produced by immunizing non-immune animals with a desired antigen generally invoke immunogenicity when injected to humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but animal-derived amino acids still have variable regions, so that chimeric antibodies have side effects with respect to a potential anti-idiotype response. Humanized antibodies have been developed to reduce such side effects. Humanized antibodies are produced by grafting complementarity determining regions (CDR) which serve an important role in antigen binding in variable regions of chimeric antibodies into a human antibody framework.

The most important thing in CDR grafting to produce humanized antibodies is choosing the optimized human antibodies for accepting CDRs of animal-derived antibodies. Antibody databases, analysis of a crystal structure, and technology for molecule modeling are used. However, even when the CDRs of animal-derived antibodies are grafted to the most optimized human antibody framework, amino acids positioned in a framework of the animal-derived CDRs affecting antigen binding are present. Therefore, in many cases, antigen binding affinity is not maintained, and thus application of additional antibody engineering technology for recovering the antigen binding affinity is necessary.

The antibodies, e.g., the anti c-Met antibodies, the anti-Ang2 antibodies, and the anti-c-Met/anti-Ang2 bispecific antibody may be animal antibodies (e.g., mouse-derived antibodies), chimeric antibodies (e.g., mouse-human chimeric antibodies), humanized antibodies, or human antibodies. The antibodies or antigen-binding fragments thereof may be isolated from a living body or non-naturally occurring. The antibodies or antigen-binding fragments thereof may be synthetic or recombinant. The antibodies or antigen-binding fragments thereof may be monoclonal.

An intact antibody includes two full-length light chains and two full-length heavy chains, in which each light chain is linked to a heavy chain by disulfide bonds. The antibody has a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2 (γ2), gamma 3 (γ3), gamma 4 (γ4), alpha 1 (α1), or alpha 2 (α2). The light chain constant region is of either a kappa (κ) or lambda (λ) type.

As used herein, the term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDR may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

The term "antigen-binding fragment" used herein refers to fragments of an intact immunoglobulin including portions of a polypeptide including antigen-binding regions having the ability to specifically bind to the antigen. In a particular embodiment, the antigen-binding fragment may be scFv, $(scFv)_2$, scFvFc, Fab, Fab', or $F(ab')_2$, but is not limited thereto.

Among the antigen-binding fragments, Fab that includes light chain and heavy chain variable regions, a light chain constant region, and a first heavy chain constant region $C_{H1}$, has one antigen-binding site.

The Fab' fragment is different from the Fab fragment, in that Fab' includes a hinge region with at least one cysteine residue at the C-terminal of $C_{H1}$.

The $F(ab')_2$ antibody is formed through disulfide bridging of the cysteine residues in the hinge region of the Fab' fragment.

Fv is the smallest antibody fragment with only a heavy chain variable region and a light chain variable region. Recombination techniques of generating the Fv fragment are widely known in the art.

Two-chain Fv includes a heavy chain variable region and a light chain region which are linked by a non-covalent bond. Single-chain Fv generally includes a heavy chain variable region and a light chain variable region which are linked by a covalent bond via a peptide linker or linked at the C-terminals to have a dimer structure like the two-chain Fv. The peptide linker may be the same as described in the above, for example, those including the amino acid length of about 1 to about 100, about 2 to about 50, particularly about 5 to about 25, and any kinds of amino acids may be included without any restrictions.

The antigen-binding fragments may be attainable using protease (for example, the Fab fragment may be obtained by restricted cleavage of a whole antibody with papain, and the $F(ab')_2$ fragment may be obtained by cleavage with pepsin), or may be prepared by using a genetic recombination technique.

The term "hinge region," as used herein, refers to a region between CH1 and CH2 domains within the heavy chain of an antibody which functions to provide flexibility for the antigen-binding site.

When an animal antibody undergoes a chimerization process, the IgG1 hinge of animal origin is replaced with a human IgG1 hinge or IgG2 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

The anti-Ang2 antibody may be a monoclonal antibody. The monoclonal antibody may be prepared by methods well known in the art. For example, it may be prepared using a phage display technique.

Meanwhile, individual monoclonal antibodies may be screened using a typical ELISA (Enzyme-Linked ImmunoSorbent Assay) format, based on the binding potential with Ang2 or c-Met. Inhibitory activities can be verified through functional analysis such as competitive ELISA for verifying the molecular interaction of binding assemblies or functional analysis such as a cell-based assay. Then, with regard to monoclonal antibody members selected on the basis of their strong inhibitory activities, their affinities (Kd values) to Ang2 or c-Met may be each verified.

In an embodiment, the anti-c-Met/anti-Ang2 bispecific antibody may include an anti-c-Met antibody or an antigen-binding fragment thereof, and an anti-Ang2 antibody or an antigen-binding fragment thereof, wherein the anti-Ang2 antibody or an antigen-binding fragment thereof is linked to C-terminus or N-terminus, e.g., C-terminus, of the anti-c-Met antibody or an antigen-binding fragment thereof.

As used herein, the term "bispecific antibody" refers to a fusion polypeptide having an antibody or antibody-like structure, which comprises a first antibody specifically recognizing and/or binding to a first antigen or an antigen-binding fragment of the first antibody, and a second antibody specifically recognizing and/or binding to a second antigen (different from the first antigen) or an antigen-binding fragment of the second antibody, wherein the second antigen or an antigen-binding fragment thereof is linked to the C-terminus of the heavy chain or the light chain of the first antibody or an antigen-binding fragment thereof directly or via a proper linker.

In the anti-c-Met/anti-Ang2 bispecific antibody, in order to fully perform the anti-c-Met antibody's activity to mediate intracellular migration and degradation of c-Met proteins, it may be advantageous that the anti-c-Met antibody has its own intact antibody structure. In addition, in case of the anti-Ang2 antibody, its specific recognition and binding to Ang2 is important, and thus it will be fine that just an antigen-binding fragment recognizing Ang2 is included in the bispecific antibody. Therefore, the anti-c-Met/anti-Ang2 bispecific antibody may comprise a complete anti-c-Met antibody (e.g., IgG type antibody; comprising two heavy chains and two light chains) and an antigen binding fragment (e.g., scFv or scFv-Fc) of the anti-Ang2 antibody linked to the C terminus of the anti-c-Met antibody, but not be limited thereto.

In the anti-c-Met/anti-Ang2 bispecific antibody, the anti-c-Met antibody or the antigen binding fragment thereof, and the anti-Ang2 antibody or the antigen binding fragment thereof, may be linked via a peptide linker or without it. Furthermore, a heavy chain portion and a light chain portion within the antigen binding fragment, for example, a heavy chain variable region and a light chain variable region within the scFv fragment, may be linked via a peptide linker or without it. The peptide linker which links the anti-c-Met antibody or the antigen binding fragment thereof, and the anti-EGFR antibody or the antigen binding fragment thereof, and the peptide linker which links the heavy chain portion and the light chain portion within the antigen binding fragment may be identical or different. The peptide linker may be about 1 to about 100, particularly about 2 to about 50, amino acids in length and include any kinds of amino acids. The peptide linker may include for example, Gly, Asn and/or Ser residues, and also include neutral amino acids such as Thr and/or Ala. Amino acid sequences suitable for the peptide linker are known in the relevant art. The length of the peptide linker may be determined within such a limit that the functions of the fusion protein (bispecific antibody) will not be affected. For instance, the peptide linker may be formed by including a total of about 1 to about 100, about 2 to about 50, or about 5 to about 25 of one or more amino acids selected from the group consisting of Gly, Asn, Ser, Thr, and Ala. In one embodiment, the peptide linker may be represented as (GGGGS)n, wherein n is a repeat number of (GGGGS), which is an integer of about 1 to about 10, particularly an integer of about 2 to about 5.

In a particular embodiment, the anti-c-Met/anti-Ang2 bispecific antibody may include an anti-c-Met antibody, and an scFv, $(scFv)_2$, Fab, Fab' or $F(ab')_2$, for example, scFv, of an anti-Ang2 antibody linked to the C terminus of the anti-c-Met antibody. For instance, scFv, $(scFv)_2$, Fab, Fab' or $F(ab')_2$ of the anti-EGFR antibody may include a heavy chain variable region including the amino acid sequence selected from SEQ ID NO: 156 to SEQ ID NO: 163, and a light chain variable region including the amino acid sequence selected from SEQ ID NO: 164 to SEQ ID NO: 171.

Hence, in a particular embodiment, the anti-c-Met/anti-Ang2 bispecific antibody may include an anti-c-Met antibody, and an scFv, $(scFv)_2$, Fab, Fab' or $F(ab')_2$ of an anti-Ang2 antibody including a heavy chain variable region including the amino acid sequence selected from SEQ ID NO: 156 to SEQ ID NO: 163, and a light chain variable region the amino acid sequence selected from SEQ ID NO: 164 to SEQ ID NO: 171, which is linked to the C terminal of the anti-c-Met antibody.

In an embodiment, the heavy chain of the anti-c-Met/anti-Ang2 bispecific antibody may include the amino acid sequence of SEQ ID NO: 189 (wherein the amino acid sequence from the $1^{st}$ to $17^{th}$ positions is a signal peptide) or the amino acid sequence from the $18^{th}$ to $738^{th}$ positions of the amino acid sequence of SEQ ID NO: 189. The light chain of the anti-c-Met/anti-Ang2 bispecific antibody may be the same with that of the above described anti-c-Met antibody, and for example, light chain may include an amino acid sequence selected from the group consisting of the amino acid sequence of SEQ ID NO: 68 (wherein the amino acid sequence from the $1^{st}$ to $20^{th}$ positions is a signal peptide), the amino acid sequence from the $21^{st}$ to $240^{th}$ positions of the amino acid sequence of SEQ ID NO: 68, the amino acid sequence of SEQ ID NO: 70 (wherein the amino acid sequence from the $1^{st}$ to $20^{th}$ positions is a signal peptide), the amino acid sequence from the 21" to $240^{th}$ positions of the amino acid sequence of SEQ ID NO: 70, and the amino acid sequence of SEQ ID NO: 108.

Due to internalization and degradation activities of the anti-c-Met antibody, the anti-c-Met/anti-Ang2 bispecific antibody is capable of not only inhibiting the activities of c-Met and Ang2, but also decreasing the total amount of c-Met and Ang2 by degrading them, thereby leading to more fundamental blocking of activity of the c-Met and Ang2. Therefore, the anti-c-Met/anti-Ang2 bispecific antibody can exhibit therapeutic effects even when it is applied to a subject who has a resistance against a preexisting Ang2-targeting drug, such as an anti-Ang2, or an anti-c-Met antibody.

In another embodiment, provided is a pharmaceutical composition including the anti-c-Met/anti-Ang2 bispecific antibody.

Another embodiment provides a pharmaceutical composition for preventing and/or treating a disease associated with Ang2/Tie2 signal transduction system and/or HGF/c-Met signal transduction system, wherein the composition includes the anti-c-Met/anti-Ang2 bispecific antibody as an active ingredient.

Another embodiment provides a method of preventing and/or treating a disease associated with Ang2/Tie2 signal transduction system and/or HGF/c-Met signal transduction system, including administering the anti-c-Met/anti-Ang2 bispecific antibody to a subject in need of preventing and/or treating a disease associated with Ang2/Tie2 signal transduction system and/or HGF/c-Met signal transduction system. The anti-c-Met/anti-Ang2 bispecific antibody may be administered in a pharmaceutically effective amount for preventing and/or treating a disease associated with Ang2/Tie2 signal transduction system and/or HGF/c-Met signal transduction system. The method may further include a step of identifying the subject in need of preventing and/or treating a disease associated with Ang2/Tie2 signal transduction system and/or HGF/c-Met signal transduction system, before the step of administering.

The disease associated with Ang2/Tie2 signal transduction system and/or HGF/c-Met signal transduction system may be a disease related to increase of angiogenesis and/or increase of vascular permeability and/or over-expression of Ang2 and/or c-Met, and for example, the disease may be at least one selected from the group consisting of cancers; cancer metastasis; eye diseases such as retinopathy of prematurity, macular degeneration (e.g., age-related macular degeneration), diabetic retinopathy, glaucoma (e.g., neovascular glaucoma) etc.; inflammatory diseases (infection) such as psoriasis, rheumatoid arthritis, pneumonia, chronic inflammation, etc.; cardiovascular diseases such as hypertension, arteriosclerosis, etc.; renal diseases; sepsis; malaria; asthma; edema; hereditary hemorrhagic telangiectasia (HHT); and the like.

Another embodiment may provide a pharmaceutical composition for presenting and/or treating a cancer, wherein the composition includes the anti-c-Met/anti-Ang2 bispecific antibody as an active ingredient.

Another embodiment provides a method of preventing and/or treating a cancer, including administering the anti-c-Met/anti-Ang2 bispecific antibody to a subject in need of preventing and/or treating a cancer. The anti-c-Met/anti-Ang2 bispecific antibody may be administered in a pharmaceutically effective amount for preventing and/or treating a cancer. The method may further include a step of identifying the subject in need of preventing and/or treating cancer, before the step of administering.

The prevention and/or treatment of a cancer may refer to prevention and/or treatment of a cancer and/or cancer metastasis.

The cancer may be a solid cancer or a blood cancer, and it may be at least one selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatocellular cancer, gastrointestinal cancer, gastric cancer, pancreatic cancer, glioblastoma, cervical cancer, ovarian cancer, liver cancer, bladder cancer, hepatoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, and the like, but not limited thereto. In particular, the cancer may be one having a resistance against a preexisting anticancer drug, such as an antagonist to c-Met or an antagonist to Ang2. The cancer may be a primary cancer or a metastatic cancer.

In the pharmaceutical composition or method, the anti-c-Met/anti-Ang2 bispecific antibody may be administered together with one or more additives selected from the group consisting of pharmaceutically acceptable carriers, diluents, excipients, and the like.

The pharmaceutically acceptable carrier may be any one commonly used in the formulation of drugs, which may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but is not limited thereto. The pharmaceutical composition may further include one or more selected from the group consisting of a diluent, an excipient, a lubricant, a wetting agent, a sweetener, a flavor enhancer, an emulsifying agent, a suspension agent, and a preservative.

The pharmaceutical composition, the anti-Ang2 antibody or an antigen-binding fragment thereof, or the anti-c-Met/anti-Ang2 bispecific antibody may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in stomach. In addition, the composition may be administered using an optional device that enables an active substance to be delivered to target cells.

The suitable dose of the pharmaceutical composition, the anti-Ang2 antibody or an antigen-binding fragment thereof, or the anti-c-Met/anti-Ang2 bispecific antibody may be prescribed in a variety of ways, depending on factors such as formulation methods, administration methods, age of subjects, body weight, gender, pathologic conditions, diets, administration time, administration interval, administration route, excretion speed, and reaction sensitivity. For example, a daily dosage of the composition the anti-Ang2 antibody or an antigen-binding fragment thereof, or the anti-c-Met/anti-Ang2 bispecific antibody may be within the range of about 0.001 to about 1000 mg/kg (e.g., about 0.001 mg/kg, about 0.01 mg/kg, about 1 mg/kg, or about 10 mg/kg), particularly about 0.01 to about 100 mg/kg (e.g., about 0.01 mg/kg, about 0.1 mg/kg, about 0.5 mg/kg, about 1 mg/kg, or about 5 mg/kg), and more particularly about 0.1 to about 50 mg/kg (e.g., about 0.1 mg/kg, about 1 mg/kg, about 10 mg/kg, or about 50 mg/kg), but is not limited thereto. The daily dosage may be formulated into a single formulation in a unit dosage form or formulated in suitably divided dosage forms, or it may be manufactured to be contained in a multiple dosage container. The term "pharmaceutically effective amount" as used herein refers to a content or dose of an active ingredient capable of showing desirable pharmacological effects and it may be determined in a variety of ways, depending on factors such as formulation methods, administration methods, age of subjects, body weight, gender, pathologic conditions, diets, administration time, administration interval, administration route, excretion speed, and reaction sensitivity.

The pharmaceutical composition or the anti-c-Met/anti-Ang2 bispecific antibody may be formulated with a pharmaceutically acceptable carrier and/or excipient into a unit or a multiple dosage form by a method easily carried out by a skilled person in the pertinent art. The dosage form may be a solution in oil or an aqueous medium, a suspension, syrup, an emulsifying solution, an extract, powder, granules, a tablet, or a capsule, and may further include a dispersing or a stabilizing agent.

In addition, the pharmaceutical composition or the anti-c-Met/anti-Ang2 bispecific antibody may be administered as an individual drug, or together with other drugs, and may be administered sequentially or simultaneously with pre-existing drugs.

In particular, the pharmaceutical composition including an antibody or an antigen-binding fragment thereof may be formulated into an immunoliposome since it contains an antibody or an antigen-binding fragment. A liposome containing an antibody may be prepared using any methods widely known in the art. The immunoliposome may be a lipid composition including phosphatidylcholine, cholesterol, and polyethyleneglycol-derivatized phosphatidylethanolamine, and may be prepared by a reverse phase evaporation method. For example, Fab' fragments of an antibody may be conjugated to the liposome through a disulfide-exchange reaction.

The subject to whom the pharmaceutical composition or the anti-c-Met/anti-Ang2 bispecific antibody is administered may be mammals, for example, primates such as humans and monkeys, or rodents such as rats and mice, or a cell or a tissue isolated from the mammal or a culture thereof, but are not be limited thereto. The subject may be a cancer patient having resistance against pre-existing anticancer drugs, for example, antagonists against a cancer-related target (e.g., c-Met, Ang2, etc.).

Another embodiment provides a polynucleotide encoding the anti-c-Met/anti-Ang2 bispecific antibody. For example, the polynucleotide may comprise or consist essentially of (i) a polynucleotide encoding a polypeptide comprising a heavy chain of an anti-c-Met antibody and an antigen-binding fragment (e.g., an scFv fragment) of an anti-Ang2 antibody linked to the C-terminus of the heavy chain of an anti-c-Met antibody, (ii) a polynucleotide encoding a polypeptide comprising a light chain of an anti-c-Met antibody, or (iii) a combination of (i) and (ii).

Another embodiment provides a recombinant vector comprising (or carrying) the polynucleotide. Another embodiment provides a recombinant cell comprising (or transfected with) the polynucleotide or the recombinant vector.

Another embodiment provides a method of preparing the anti-c-Met/anti-Ang2 bispecific antibody, comprising expressing a polynucleotide encoding the anti-c-Met/anti-Ang2 bispecific antibody in a cell. As described above, the polynucleotide may comprise or consist essentially of (i) a polynucleotide encoding a polypeptide comprising a heavy chain of an anti-c-Met antibody and an antigen-binding fragment (e.g., an scFv fragment) of an anti-Ang2 antibody linked to the C-terminus of the heavy chain of an anti-c-Met antibody, (ii) a polynucleotide encoding a polypeptide comprising a light chain of an anti-c-Met antibody, or (iii) a combination of (i) and (ii). In the method, the nucleotides (i) and (ii) are carried into a cell together by one vector or separately by two vectors. Another embodiment provides a method of preparing the anti-c-Met/anti-Ang2 bispecific antibody, comprising linking an anti-Ang2 antibody or an antigen-binding fragment thereof to C-terminus or N-terminus of an anti-c-Met antibody or an antigen-binding fragment thereof. For example, the method may comprise linking an antigen-binding fragment (e.g., an scFv fragment) of an anti-Ang2 antibody to a c-terminus of an anti-c-Met antibody.

In the nucleotide, the vector, the cell, and the method, the anti-c-Met/anti-Ang2 bispecific antibody, the heavy chain of an anti-c-Met antibody, the light chain of an anti-c-Met antibody, and the antigen-binding fragment (e.g., an scFv fragment) of an anti-Ang2 antibody are as described above.

The anti-c-Met/anti-Ang2 antibody possess both characteristics as an inhibitor against Ang2/Tie2 signal transduction and c-Met/HGF signal transduction, and may exhibit the following effects of:

1. Increasing the therapeutic efficacy compared to administration of Ang2/Tie2 inhibitor alone, HGF/c-Met inhibitor alone, or a combination thereof, thereby decreasing the administration amount, 2. being used in treatment of a metastatic cancer as well as a primary cancer, and 3. being applied to a disease associated with Ang2/Tie2 signal transduction and HGF/c-Met signal transduction, other than cancers.

EXAMPLES

Hereafter, the present invention will be described in detail by examples.

The following examples are intended merely to illustrate the invention and are not construed to restrict the invention.

Reference Example 1

Construction of an Anti-c-Met Antibody 1.1. Production of "AbF46", a Mouse Antibody to c-Met 1.1.1. Immunization of a Mouse To obtain immunized mice necessary for the development of a hybridoma cell line, each of five BALB/c mice (Japan SLC, Inc.), 4 to 6 weeks old, was intraperitoneally injected with a mixture of 100 μg of human c-Met/Fc fusion protein (R&D Systems) and one volume of complete Freund's adjuvant. Two weeks after the injection, a second intraperitoneal injection was conducted on the same mice with a mixture of 50 μg of human c-Met/Fc protein and one volume of incomplete Freund's adjuvant. One week after the second immunization, the immune response was finally boosted. Three days later, blood was taken from the tails of the mice and the sera were 1/1000 diluted in PBS and used to examine a titer of antibody to c-Met by ELISA. Mice found to have a sufficient antibody titer were selected for use in the cell fusion process.

1.1.2. Cell fusion and Production of a Hybridoma

Three days before cell fusion, BALB/c mice (Japan SLC, Inc.) were immunized with an intraperitoneal injection of a mixture of 50 μg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1\times10^8$ cells) were mixed with myeloma cells (Sp2/0) ($1\times10^8$ cells), followed by spinning to give a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in a water bath at 37° C. for 5 min. Then the cell volume was adjusted to 50 mL before centrifugation. The cell pellet thus formed was resuspended at a density of $1\sim2\times10^5$ cells/mL in a selection medium (HAT medium) and 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 μL (2 μg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 μL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 9, 2009, under Accession No. KCLRF-BP-00220 according to the Budapest Treaty (see Korean Patent Laid-Open Publication No. 2011-0047698).

1.1.4. Production and Purification of a Monoclonal Antibody

The hybridoma cell line obtained in Reference Example 1.1.3 was cultured in a serum-free medium, and the monoclonal antibody (AbF46) was produced and purified from the cell culture.

First, the hybridoma cells cultured in 50 mL of a medium (DMEM) supplemented with 10% (v/v) fetal bovine serum (FBS) were centrifuged and the cell pellet was washed twice or more with 20 mL of PBS to remove the FBS therefrom. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with an filter (Amicon). The antibody was stored in PBS before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mouse antibody AbF46 produced in Reference Example 1.1.4 by replacing the constant region, but not the variable region responsible for antibody specificity, with an amino sequence of the human IgG1 antibody.

In this regard, a gene was designed to include the nucleotide sequence of "EcoRI-signal sequence-VH-NheI-CH-TGA-XhoI" (SEQ ID NO: 38) for a heavy chain and the nucleotide sequence of "EcoRI-signal sequence-VL-BsiWI-CL-TGA-XhoI" (SEQ ID NO: 39) for a light chain and synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a vector from the pOptiVEC™-TOPO TA Cloning Kit enclosed in an OptiCHO™ Antibody Express Kit (Cat no. 12762-019, Invitrogen), and a vector from the pcDNA™ 3.3-TOPO TA Cloning Kit (Cat no. 8300-01), respectively.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE Healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest identity/homology with the VH gene of the mouse antibody AbF46 purified in Reference Example 1.2 were analyzed. An Ig BLAST (www.ncbi.nlm.nih.gov/igblast/) result revealed that VH3-71 has an identity/identity/homology of 83% at the amino acid level. CDR-H1, CDR-H2, and CDR-H3 of the mouse antibody AbF46 were defined according to Kabat numbering. A design was made to introduce the CDR of the mouse antibody AbF46 into the framework of VH3-71. Hereupon, back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a BLAST search. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest identity/homology with the VH gene of the mouse antibody AbF46 were analyzed. An Ig BLAST search result revealed that VK4-1 has a identity/homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1. Hereupon, back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest identity/homology with the VL gene of the mouse antibody AbF46 were analyzed by a BLAST search. As a result, VK2-40 was selected. VL and VK2-40 of the mouse antibody AbF46 were found to have a identity/homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A Blast search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Hereupon, back mutations were conducted at positions 36 (Y→H), 46 (L→M), and 49 (Y→I) on H4-light.

Thereafter, DNA fragments having the heavy chain nucleotide sequences (H1-heavy: SEQ ID NO: 47, H3-heavy: SEQ ID NO: 48, H4-heavy: SEQ ID NO: 49) and DNA fragments having the light chain nucleotide sequences (H1-light: SEQ ID NO: 50, H2-light: SEQ ID NO: 51, H3-light: SEQ ID NO: 52, H4-light: SEQ ID NO: 53) were digested with EcoRI (NEB, R0101S) and XhoI (NEB, R0146S) before cloning into a vector from the pOptiVEC™-TOPO TA Cloning Kit enclosed in an OptiCHO™ Antibody Express Kit (Cat no. 12762-019, Invitrogen) and a vector from the pcDNA™ 3.3-TOPO TA Cloning Kit (Cat no. 8300-01), respectively, so as to construct recombinant vectors for expressing a humanized antibody.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5\times10^5$ cells/ml. After 24 hours, when the cell number reached $1\times10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE Healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples included a combination of H4-heavy (SEQ ID NO: 42) and H4-light (SEQ ID NO: 46).

1.4. Construction of an scFV Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker having the amino acid sequence "GLGGLGGGGSGGGGSGGSSGVGS" (SEQ ID NO: 54). A polynucleotide sequence (SEQ ID NO: 55) encoding the designed scFv of huAbF46 was synthesized in Bioneer and an expression vector for the polynucleotide had the nucleotide sequence of SEQ ID NO: 56.

After expression, the product was found to exhibit specificity to c-Met.

1.5. Construction of Library Genes for Affinity Maturation 1.5.1. Selection of Target CDRs and Synthesis of Primers The affinity maturation of huAbF46 was achieved. First, six complementary determining regions (CDRs) were defined according to Kabat numbering. The CDRs are given in Table 4, below.

TABLE 4

| CDR | Amino Acid Sequence |
|---|---|
| CDR-H1 | DYYMS(SEQ ID NO: 1) |
| CDR-H2 | FIRNKANGYTTEYSASVKG(SEQ ID NO: 2) |
| CDR-H3 | DNWFAY(SEQ ID NO: 3) |
| CDR-L1 | KSSQSLLASGNQNNYLA(SEQ ID NO: 10) |
| CDR-L2 | WASTRVS(SEQ ID NO: 11) |
| CDR-L3 | QQSYSAPLT(SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

1.5.2. Construction of a Library of huAbF46 Antibodies and Affinity for c-Met

The construction of antibody gene libraries through the introduction of random sequences was carried out using the primers synthesized in the same manner as in Reference Example 1.5.1. Two PCR products were obtained using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of an Antibody with Improved Affinity from Libraries

After maturation of the affinity of the constructed libraries for c-Met, the nucleotide sequence of scFv from each clone was analyzed. The nucleotide sequences thus obtained are summarized in Table 2 and were converted into IgG forms. Four antibodies which were respectively produced from clones L3-1, L3-2, L3-3, and L3-5 were used in the subsequent experiments.

TABLE 5

| Clone | Library constructed | CDR Sequence |
|---|---|---|
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides encoding heavy chains of the four selected antibodies were designed to have the structure of "EcoRI-signal sequence-VH-NheI-CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences (DNA fragment including L3-1-derived CDR-L3: SEQ ID NO: 58, DNA fragment including L3-2-derived CDR-L3: SEQ ID NO: 59, DNA fragment including L3-3-derived CDR-L3: SEQ ID NO: 60, and DNA fragment including L3-5-derived CDR-L3: SEQ ID NO: 61) were digested with EcoRI (NEB, R0101S) and XhoI (NEB, R0146S) before cloning into a vector from the pOptiVEC™-TOPO TA Cloning Kit enclosed in an OptiCHO™ Antibody Express Kit (Cat no. 12762-019, Invitrogen) and a vector from the pcDNA™ 3.3-TOPO TA Cloning Kit (Cat no. 8300-01), respectively, so as to construct recombinant vectors for expressing affinity-matured antibodies.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE Healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of (a) a heavy chain including the heavy chain variable region of huAbF46-H4-A1, U6-HC7 hinge, and the constant region of human IgG1 constant region, and (b) a light chain including the light chain variable region of huAbF46-H4-A1 and human kappa constant region. The antibody huAbF46-H4-A1 (IgG2 hinge) was composed of (a) a heavy chain including a heavy chain variable region, a human IgG2 hinge region, and a human IgG1 constant region, and (b) a light chain including the light chain variable region of huAbF46-H4-A1 and a human kappa constant region. The antibody huAbF46-H4-A1 (IgG2 Fc) was composed of (a) the heavy chain variable region of huAbF46-H4-A1, a human IgG2 hinge region, and a human IgG2 constant region, and (b) a light chain including the light variable region of huAbF46-H4-A1 and a human kappa constant region. Hereupon, the histidine residue at position 36 on the human kappa constant region of the light chain was changed to tyrosine in all of the three antibodies to increase antibody production.

For use in constructing the three antibodies, a polynucleotide (SEQ ID NO: 63) encoding a polypeptide (SEQ ID NO: 62) composed of the heavy chain variable region of huAbF46-H4-A1, a U6-HC7 hinge region, and a human IgG1 constant region, a polynucleotide (SEQ ID NO: 65) encoding a polypeptide (SEQ ID NO: 64) composed of the heavy chain variable region of huAbF46-H4-A1, a human IgG2 hinge region, and a human IgG1 region, a polynucleotide (SEQ ID NO: 67) encoding a polypeptide (SEQ ID NO: 66) composed of the heavy chain variable region of huAbF46-H4-A1, a human IgG2 region, and a human IgG2 constant region, and a polynucleotide (SEQ ID NO: 69) encoding a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a vector from the pOptiVEC™-TOPO TA Cloning Kit enclosed in an OptiCHO™ Antibody Express Kit (Cat no. 12762-019, Invitrogen) while DNA fragments having light chain nucleotide sequences were inserted into a vector from the pcDNA™ 3.3-TOPO TA Cloning Kit (Cat no. 8300-01) so as to construct vectors for expressing the antibodies.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE Healthcare, 17-0405-03), followed by elution with IgG elution buffer (Thermo Scientific, 21004). The buffer was exchanged with PBS to finally purify three antibodies (huAbF46-H4-A1 (U6-HC7), huAbF46-H4-A1 (IgG2 hinge), and huAbF46-H4-A1 (IgG2 Fc)). Among the three antibodies, huAbF46-H4-A1 (IgG2 Fc) was representatively selected for the following examples, and referred as L3-1Y-IgG2.

Reference Example 2

Preparation of Anti-Ang2 Antibody 2.1. Ang2-Binding scFv Clone

With regard to human Ang2 polypeptide (R&D systems; Human Ang2; Accession #O15123 (hAng2); SEQ ID NO: 172), a complete human anti-Ang2 antibody was prepared using a phage display scFv library (obtained from Ewha Women's University-Industry Collaboration Foundation). A detailed protocol thereof is as follows:

The Ang2 polypeptide was applied to a Maxisorp immunotube in amounts of about 10 μg/ml, 1 μg/ml and 0.1 μg/ml, respectively to enrich antibodies responding to Ang2 through 1$^{st}$, 2$^{nd}$, and 3$^{rd}$ pannings. After the surface of the immunotube was blocked with about 3% (v/v) milk dissolved in PBS, about $1\times10^{12}$ of phage particles derived from the same phage display scFv library as described above were added to about 0.5 ml of 3% (v/v) milk, which was isothermally treated together at 37° C. for 1 hours for blocking. After that, the phages blocked with milk were put into the immunotube applied with Ang2, followed by isothermal treatment at a room temperature for 1 hour to allow Ang2 and the phages to be bound.

After the isothermal treatment of the phages, the surface of the phages were washed 3 to 5 times with PBS and about 0.1% (v/v) Tween 20 and then, the bound phages were eluted using 100 mM triethanolamine. The eluted phages were transfected into *E. coli* ER2537 cells (New England Biolabs, USA), amplified, and then obtained to be ready for use in the next screening step. The procedure was repeated three times by applying the Ang2 polypeptide to a Maxisorp immunotube in amounts of about 10 μg/ml, 1 μg/ml, and 0.1 μg/ml, respectively and then, about 600 specific Ang2 bound scFv clones recognizing human Ang2 (Accession #O15123) or mouse Ang2 (Accession #NP_031452) were identified when measured using ELISA (Enzyme-Linked ImmunoSorbent Assay) affinity assay (see Example 2.2) as described below.

2.2. Selection of an Anti-Ang2 Antibody Producing Clone and Purification of an Antibody Based on binding potential with Ang2 using an ELISA format, 70 clones which produce anti-Ang2 antibodies were selected from the about 600 Ang2 bound scFv clones obtained in Example 2.1 above. Specifically, clones with high ELISA OD were selected among the clones which can bind to Ang2 and inhibit Tie2 binding. Then, each clone was cultured in SB media to which ampicillin was added up to the level of OD 600=1.0, 1 mM IPTG (Isopropyl-β-D-Thiogalactopyranoside) was injected thereto and then, periplasm fractions were collected to partially purify anti-Ang2 monoclonal antibodies using NI-NTA column (QIAGEN).

2.3. Ang2:Tie2 Neutralization ELISA (Competitive ELISA)

To verify molecular interaction of the bound assemblies, a competitive ELISA was performed. A 96-well MaxiSorp™ flat-bottom plate (Nunc) was coated with 4 μg/μl of hTie2-Fc (R&D Systems), which is a protein with the Fc of human IgG1 bound thereto. After that, the plate was washed five times with 0.05% (v/v) Tween-20-containing PBS (Phosphate Buffer Saline) and then blocked with 1% (v/v) BSA (Bovine serum albumin; Sigma)-containing PBS at a room temperature for 2 hours.

To perform Ang2:Tie2 neutralization ELISA, the anti-Ang2 antibodies in their scfv forms purified in Example 2.2 (1, 10, 100, and 1000 nM) were added to each well of the plate coated with hTie2-Fc, along with 1% (v/v) BSA and 400 ng/ml of FLAG-Tagged hAng2 and then, the plate was allowed to react at a room temperature for 2 hours. Thereafter, the plate was washed five times with 0.05% Tween-20-containing PBS and then, an HRP-conjugated anti-FLAG antibody (SIGMA) diluted in 1% (v/v) BSA-containing PBS at 1:5,000 ratio (v/v) was added in the amount of 100 μl (microliter) to each well to react at a room temperature for 1 hour, followed by washing five times with 0.1% (v/v) Tween-20-containing PBS. Finally, 100 μl (microliter) of TMB substrate (cell signal) was added to each well of the plate to induce color development at a room temperature for 3 min. Then, the reaction was ceased by the addition of 50 μl of 5N $H_2SO_4$ solution and OD450 values were measured on a plate reader (Molecular Devices). Through them, 50% inhibition concentrations (IC50) against Ang2:Tie2 binding were obtained and shown in the following Table 6.

TABLE 6

| antibody | 50% inhibition concentration against Ang2:Tie2 binding ($IC_{50}$, nM) |
|---|---|
| SAIT-ANG-2-AB-2-E6 | 18.9 |
| SAIT-ANG-2-AB-4-H10 | 24.3 |
| SAIT-ANG-2-AB-8-A5 | 36.3 |
| SAIT-ANG-2-AB-7-C9 | 39.7 |
| SAIT-ANG-2-AB-3-D3 | 9.9 |
| SAIT-ANG-2-AB-4-C11 | 6.5 |
| SAIT-ANG-2-AB-4-F5 | 10 |
| SAIT-ANG-2-AB-4-F11 | 6.6 |

As in Table 6 above, it was confirmed that the anti-Ang2 antibodies can neutralize the binding between Ang2 and Tie2 receptors.

2.4. Binding ELISA of hAng2 and mAng2

To measure binding of the antibodies prepared above with each antigen, ELISA was performed. A 96-well MaxiSorp™ flat-bottom plate (Nunc) was coated with 5~20 μg/ml of human Ang2 and mouse Ang2 (Accession #NP_031452) (both, R&D Systems). After that, the plate was washed five times with 0.05% (v/v) Tween-20-containing PBS and then blocked with 1% (v/v) BSA-containing PBS at a room temperature for 2 hours. The anti-Ang2 antibodies in their scFv forms prepared above were added to each well of the plate which was then allowed to react at a room temperature for 2 hours.

Thereafter, the plate was washed five times with 0.05% Tween-20-containing PBS and then, an HRP-conjugated anti-HA (HA-probe Antibody (F-7) HRP conjugated) antibody (Santacruz) diluted in 1% (v/v) BSA-containing PBS at 1:1,000 ratio (v/v) was added in the amount of 50 μl to each well to react at a room temperature for 1 hour, followed by washing five times with 0.1% (v/v) Tween-20-containing PBS. Finally, 100 μl of TMB substrate (cell signal) was added to each well of the plate to induce color development at a room temperature for 3 min and then, the reaction was ceased by the addition of 50 μl of 5N $H_2SO_4$ solution and OD450 values were measured on a plate reader (Molecular Devices). By obtaining 50% binding concentrations (Kd) to human Ang2 and mouse Ang2 proteins through them, the binding degrees of the anti-Ang2 antibodies to each antigen were measured. The obtained results are shown in the following Table 7.

TABLE 7

| Antibody | human Ang2 (Kd, nM) | mouse Ang2 (Kd, nM) |
|---|---|---|
| SAIT-ANG2-AB-2-E6 | 9.3 | 5.1 |
| SAIT-ANG2-AB-4-H10 | 5.3 | 15.8 |
| SAIT-ANG2-AB-8-A5 | 5.3 | 11.7 |
| SAIT-ANG2-AB-7-C9 | 3.8 | 8.7 |
| SAIT-ANG2-AB-3-D3 | 4.3 | 37.8 |
| SAIT-ANG2-AB-4-C11 | 4.9 | 28.6 |
| SAIT-ANG2-AB-4-F5 | 12.1 | 23.8 |
| SAIT-ANG2-AB-4-F11 | 3 | 20.7 |

2.5. Ang2 Epitope Mapping

To identify each epitope for the anti-Ang2 antibodies obtained above, ELISA was performed using recombinant proteins in which the receptor binding sites of Ang2 protein were artificially mutated.

A 96-well MaxiSorp™ flat-bottom plate (Nunc) was coated with 50 μl of the anti-Ang2 scFv selected above. After that, the plate was washed five times with 0.05% (v/v) Tween-20-containing PBS and then blocked with 1% (v/v) BSA-containing PBS at a room temperature for 2 hours.

S417, Q418, P419, N421, I434, D448, A449, P452, Y460, N467, K468, or F469 residue of Ang2 was mutated with alanine and tagged with FLAG (N-DYKDDDDK-C; 1012 Da, SEQ ID NO: 201) and then 250 ng of them was each added to each well to the plate, which was allowed to react at a room temperature for 2 hours. Thereafter, the plate was washed five times with 0.05% Tween-20-containing PBS and then, an HRP-conjugated anti-FLAG antibody (SIGMA) diluted in 1% (v/v) BSA-containing PBS at 1:5,000 ratio (v/v) was added in the amount of 50 µl to each well to react at a room temperature for 1 hour, followed by washing five times with 0.1% (v/v) Tween-20-containing PBS.

Finally, 100 µl of TMB substrate (cell signal) was added to each well of the plate to induce color development and then, the reaction was ceased by the addition of 50 µl of 5N $H_2SO_4$ solution and OD450 values were measured on a plate reader (Molecular Devices). By comparing binding with mutated Ang2 to binding with non-mutated Ang2, each epitope for the Ang2 antibodies was identified. The obtained results are shown in the following Tables 8 and 9.

TABLE 8

| | Relative binding (%) with Mutant Ang2 compared to the binding with native Ang2 | | | | | | |
|---|---|---|---|---|---|---|---|
| | I434 | A449 | P452 | Y460 | N467 | K468 | F469 |
| AB-2-E6 | 5.3 | 3.3 | 24.0 | 40.0 | 72.1 | 94.0 | 112.3 |
| AB-4-H10 | 32.9 | 71.0 | 269.8 | 245.8 | 29.8 | 214.5 | 276.7 |
| AB-8-A5 | 4.0 | 30.5 | 86.5 | 91.6 | 90.7 | 101.0 | 101.5 |
| AB-7-C9 | 8.7 | 14.5 | 85.0 | 78.1 | 86.6 | 97.3 | 89.4 |
| AB-3-D3 | 93.4 | 100.6 | 97.3 | 95.1 | 90.9 | 95.9 | 96.4 |
| AB-4-C11 | 7.2 | 4.8 | 70.0 | 74.3 | 81.7 | 94.8 | 102.3 |
| AB-4-F5 | 68.6 | 14.0 | 15.0 | 21.8 | 11.3 | 87.4 | 259.0 |
| AB-4-F11 | 69.0 | 16.7 | 91.6 | 96.1 | 92.0 | 101.5 | 104.9 |
| Control Antibody 1 | 93.3 | 95.8 | 95.4 | 86.7 | 94.4 | 86.9 | 3.2 |

(Of the above table, control antibody 1 is Regeneron Ang2 antibody.)

TABLE 9

| | Clone # | Epitope (binding region) |
|---|---|---|
| 1 | AB-2-E6, AB-7-C9, AB-4-C11 | I434, A449 |
| 2 | AB-8-A5 | I434 |
| 3 | AB-4-F11 | A449 |
| 4 | AB-4-F5 | A449, P452, N467 |

2.6. Human Anti-Ang2 Antibody Gene Cloning

The gene sequences of heavy chain and light chain variable regions of monoclonal antibodies to be produced from each clone were amplified using a thermocycler (GeneAmp PCR System 9700, Applied Biosystem) from each antibody producing *E. coli* glycerol stock obtained from the above antibody selection results.

PCR Conditions 5 min. at 94° C.;

[1 min. at 94° C., 1 min. at 55° C., and 2 min. at 72° C.]×30 cycles;

6 min. at 72° C.;

Cooling to 4° C.

Primers: pC3X-f: 3'-GCACGACAGGTTTCCCGAC-5' (SEQ ID NO: 190), pC3X-b: 3'-AACCATCGA-TAGCAGCACCG-5'(SEQ ID NO: 191).

The PCR products obtained from each reaction were washed with QIAquick Multiwell PCR Purification kit (Qiagen) according to the Manufacturer's protocol.

The PCR results obtained above were cloned and subjected to DNA sequencing by a well-known method. As a result, CDR sequences shown in the following Table 10 and Table 11 were able to be obtained.

TABLE 10

| | Amino acid sequence of heavy chain CDR | | |
|---|---|---|---|
| antibody | CDRH1-KABAT | CDRH2-KABAT | CDRH3-KABAT |
| SAIT-ANG-2-AB-2-E6 | DYAMS (SEQ ID NO: 109) | AIYPDSGNKYYADSVKG (SEQ ID NO: 115) | ARHSSDPKVKSGYYDDGMDV (SEQ ID NO: 122) |
| SAIT-ANG-2-AB-8-A5 | DYYMS (SEQ ID NO: 110) | GIYPSGGSTYYADSVKG (SEQ ID NO: 116) | ARDPSTLTYAGFDY(SEQ ID NO: 123) |
| SAIT-ANG-2-AB-7-C9 | NYAMS (SEQ ID NO: 111) | AISSGGGNIYYADSVKG (SEQ ID NO: 117) | AKSGIQPSPPSMSSAYAMDV (SEQ ID NO: 124) |
| SAIT-ANG-2-AB-4-C11 | DYAMS (SEQ ID NO: 109) | SIYPDDGNTYYADSVKG (SEQ ID NO: 118) | ARHTSHHTSIDGYYYYGMDG (SEQ ID NO: 125) |
| SAIT-ANG-2-AB-4-F5 | DYDMS (SEQ ID NO: 112) | SISHGDSNKYYADSVKG (SEQ ID NO: 119) | AKSSGIQESPPTYYYYGMDV (SEQ ID NO: 126) |
| SAIT-ANG-2-AB-4-F11 | DYAMS (SEQ ID NO: 109) | SIYPDDGNTYYADSVKG (SEQ ID NO: 118) | AKHPVRLNLHPMYYYYGMDV (SEQ ID NO: 127) |
| SAIT-ANG-2-AB-4-H10 | SYDMS (SEQ ID NO: 113) | LISPDSSSIYYADSVKG (SEQ ID NO: 120) | AKDLISFWRGGFDY(SEQ ID NO: 128) |
| SAIT-ANG-2-AB-3-D3 | DYDMS (SEQ ID NO: 114) | GISSDDGNTYYADSVKG (SEQ ID NO: 121) | ARPTIDKYTLRGYYSYGMDV (SEQ ID NO: 129) |

TABLE 11

| antibody | Amino acid sequence of light chain CDR: CDRL1-KABAT | CDRL2-KABAT | CDRL3-KABAT |
|---|---|---|---|
| SAIT-ANG-2-AB-2-E6 | SGSSSNIGNNAVN (SEQ ID NO: 130) | ADSNRPS (SEQ ID NO: 138) | GSWDYSLSG (SEQ ID NO: 145) |
| SAIT-ANG-2-AB-8-A5 | SGSSSNIGNNYVT (SEQ ID NO: 131) | ADSHRPS (SEQ ID NO: 139) | ATWDYSLSG (SEQ ID NO: 146) |
| SAIT-ANG-2-AB-7-C9 | SGSSSNIGNNDVY (SEQ ID NO: 132) | ANSHRPS (SEQ ID NO: 140) | GTWDYSLSG (SEQ ID NO: 147) |
| SAIT-ANG-2-AB-4-C11 | TGSSSNIGNNDVS (SEQ ID NO: 133) | SDSKRPS (SEQ ID NO: 141) | GSWDYSLSG (SEQ ID NO: 145) |
| SAIT-ANG-2-AB-4-F5 | SGSSSNIGSNAVN (SEQ ID NO: 134) | ADSNRPS (SEQ ID NO: 138) | GSWDYSLSG (SEQ ID NO: 145) |
| SAIT-ANG-2-AB-4-F11 | TGSSSNIGNNAVS (SEQ ID NO: 135) | SDSQRPS (SEQ ID NO: 142) | ATWDYSLSA (SEQ ID NO: 148) |
| SAIT-ANG-2-AB-4-H10 | SGSSSNIGSNYVN (SEQ ID NO: 136) | SDSHRPS (SEQ ID NO: 143) | GAWDDSLSG (SEQ ID NO: 149) |
| SAIT-ANG-2-AB-3-D3 | TGSSSNIGSNYVS (SEQ ID NO: 137) | SDNKRPS (SEQ ID NO: 144) | GTWDDSLNG (SEQ ID NO: 150) |

2.7. Expression and Purification of Intact Antibody

The heavy chain and light chain variable regions obtained in Example 2.6 above (see Tables 12 and 13 below) were each cloned into different vectors. The heavy chain variable region was cloned into a vector pOPTI-VAC (Invitrogen) having a CMV promoter (cytomegalovirus promoter) and including the constant region and Fc region of human IgG1. The light chain variable region was cloned into a vector pFUSE2-CLIg-h12 (Invivogen) having a CMV promoter (cytomegalovirus promoter) and including the constant region of human IgG1.

In particular, the heavy chain and the vector including it were treated with ecorI (neb) and NheI (neb) restriction enzymes and the light chain and the vector including it were treated with ecorI (neb) and avrII (neb) restriction enzymes and then, they were ligated with a T4 DNA Ligase (New England Biolab) to prepare a heavy chain vector and a light chain vector for human antibody expression including the desirable regions.

The thus obtained heavy chain vector and light chain vector were transfected together into 293-F cells (Invitrogen). The cells were cultured in a serum-free 293-f expression medium (Invitrogen) at 37° C. and on 5 days, the culture medium was collected. As a result of SDS-PAGE, the culture medium obtained from the culture included human antibodies consisting of heavy chains and light chains having variable region sequences set forth in the following Tables 12 and 13. The culture medium containing the expressed chimeric antibodies was centrifuged at the speed of 1000×g for 10 min to remove the remaining cells and impurities, followed by affinity chromatography using Protein A (GE-Healthcare) having a strong affinity to antibody Fc regions to purify antibodies through a low PH elution.

The amino acid sequences and the nucleotide sequences of the heavy chain variable regions and the light chain variable regions of the antibodies purified above were analyzed and shown in the following Table 12 and Table 13.

TABLE 12

| antibody | Amino acid sequence of heavy chain variable region | Amino acid sequence of light chain variable region |
|---|---|---|
| SAIT-ANG-2-AB-2-E6 | EVQLLESGGGLVQTGGSLRLSCAASGFTFS**DYAM**SWVRQAPGKGLEWVS**AIYPDSGNKYYADSVKG**RFTISRDNSKNTLYLQMNSLRAEDTAVYYC**ARHSSDPKVKSGYYDDGMDV**WGQGTLVAVSS (SEQ ID NO: 156) | QSVLTQPPSASGTPGQRVTISC**SGSSSNIGNNAVN**WYQQLPGTAPKLLIY**ADSNRPS**GVPDRFSGSKSGTSASLAISGLRSEDEADYYC**GSWDYSLSG**YVFGGGTKLTVLG (SEQ ID NO: 164) |
| SAIT-ANG-2-AB-8-A5 | EVQLLESGGGLVQPGGSLRLSCAASGFTFS**DYYMS**WVRQAPGKGLEWVS**GIYPSGGSTYYADSVKG**RFTISRDNSKNTLYLQMNSLRAEDTAVYYC**ARDPSTLTYAGFDY**WGQGTLVTVSS (SEQ ID NO: 157) | QSVLTQPPSASGTPGQRVTISC**SGSSSNIGNNYVT**WYQQLPGTAPKLLIY**ADSHRPS**GVPDRFSGSKSGTSASLAISGLRSEDEADYYC**ATWDYSLSG**YVFGGGTKLTVLG (SEQ ID NO: 165) |
| SAIT-ANG-2-AB-7-C9 | EVQLLESGGGLVQPGGSLRLSCAASGFTFS**NYAMS**WVRQAPGKGLEWVS**AISSGGGNIYYADSVKG**RFTISRDNSKNTLYLQMNSLRAEDTAVYYC**AKSGIQPSPPSMSSAYAMDV**WGQGTLVTVSS (SEQ ID NO: 158) | QSVLTQPPSASGTPGQRVTISC**SGSSSNIGNNDVY**WYQQLPGTAPKLLIY**ANSHRPS**GVPDRFSGSKSGTSASLAISGLRSEDEADYYC**GTWDYSLSG**YVFGGGTKLTVLG (SEQ ID NO: 166) |

TABLE 12-continued

| antibody | Amino acid sequence of heavy chain variable region | Amino acid sequence of light chain variable region |
|---|---|---|
| SAIT-ANG-2-AB-4-C11 | EVQLLESGGGLVQPGGSLRLSCAA SGFTFS**DYAMS**WVRQAPGKGLEW VS**SIYPDDGNTYYADSVKG**RFTIS RDNSKNTLYLQMNSLRAEDTAVY YC**ARHTSHHTSIDGYYYYGMDG** WGQGTLVTVSS (SEQ ID NO: 159) | QSVLTQPPSASGTPGQRVTISC**TGS SSNIGNNDVS**WYQQLPGTAPKLLI Y**SDSKRPS**GVPDRFSGSKSGTSASL AISGLRSEDEADYYC**GSWDYSLSG** YVFGGGTKLTVLG (SEQ ID NO: 167) |
| SAIT-ANG-2-AB-4-F5 | EVQLLESGGGLVQPGGSLRLSCAA SGFTFS**DYDMS**WVRQAPGKGLEW VS**SISHGDSNKYYADSVKG**RFTIS RDNSKNTLYLQMNSLRAEDTAVY YC**AKSSGIQESPPTYYYYGMDV**W GQGTLVTVSS (SEQ ID NO: 160) | QSVLTQPPSASGTPGQRVTISC**SGS SSNIGSNAVN**WYQQLPGTAPKLLI Y**ADSNRPS**GVPDRFSGSKSGTSAS LAISGLRSEDEADYYC**GSWDYSLS G**YVFGGGTKLTVLG (SEQ ID NO: 168) |
| SAIT-ANG-2-AB-4-F11 | EVQLLESGGGLVQTGGSLRLSCAA SGFTFS**DYAMS**WVRQAPGKGLEW VS**SIYPDDGNTYYADSVKG**RFTIS RDNSKNTLYLQMNSLRAEDTAVY YC**AKHPVRLNLHPMYYYYGMD** VWGQGTLVTVSS (SEQ ID NO: 161) | QSVLTQPPSASGTPGQRVTISC**TGS SSNIGNNAVS**WYQQLPGTAPKLLI Y**SDSQRPS**GVPDRFSGSKSGTSASL AISGLRSEDEADYYC**ATWDYSLSA** YVFGGGTKLTVLG (SEQ ID NO: 169) |
| SAIT-ANG-2-AB-4-H10 | EVQLLESGGGLVQPGGSLRLSCAA SGFTFS**SYDMS**WVRQAPGKGLEW VS**LISPDSSSIYYADSVKG**RFTISR DNSKNTLYLQMNSLRAEDTAVYY C**AKDLISFWRGGFDY**WGQGTLV TVSS (SEQ ID NO: 162) | QSVLTQPPSASGTPGQRVTISC**SGS SSNIGSNYVN**WYQQLPGTAPKLLI Y**SDSNRPS**GVPDRFSGSKSGTSAS LAISGLRSEDEADYYC**GAWDDSLS G**YVFGGGTKLTVLG (SEQ ID NO: 170) |
| SAIT-ANG-2-AB-3-D3 | EVQLLESGGGLVQPGGSLRLSCAA SGFTFS**DYDMS**WVRQAPGKGLEW VS**GISSDDGNTYYADSVKG**RFTIS RDNSKNTLYLQMNSLRAEDTAVY YC**ARPTIDKYTLRGYYSYGMDV** WGQGTLVTVSS (SEQ ID NO: 163) | QSVLTQPPSASGTPGQRVTISC**TGS SSNIGSNYVS**WYQQLPGTAPKLLI Y**SDNKRPS**GVPDRFSGSKSGTSAS LAISGLRSEDEADYYC**GTWDDSL NG**YVFGGGTKLTVLG (SEQ ID NO: 171) |

(Of the above Table, portions marked in bold types are CDR1, CDR2, and CDR3 in order.)

TABLE 13

| antibody | Amino acid sequence of heavy chain variable region | Amino acid sequence of light chain variable region |
|---|---|---|
| SAIT-ANG-2-AB-2-E6 | GAAGTGCAGCTTCTGGAATCAGGCG GTGGACTGGTGCAGCCAGGAGGCAG CCTCAGGCTGTCTTGCGCAGCCAGC GGATTTACCTTCTCCGATTACGCCAT GAGCTGGGTTAGACAGGCCCCTGGC AAGGGGCTGGAGTGGGTCAGTGCCA TTTACCCCGACTCCGGGAATAAGTA TTACGCTGACTCTGTGAAAGGTAGA TTCACTATCTCAAGAGACAACTCCA AAAATACATTGTACTTACAGATGAA CTCACTGCGCGCTGAGGATACAGCA GTGTATTATTGTGCGCGGCACTCGA GTGATCCTAAGGTCAAAAGCGGATA CTATGACGACGGCATGGATGTTTGG GGCCAAGGGACTCTCGTAACCGTGT CTTCT (SEQ ID NO: 173) | CAGTCAGTCCTGACACAGCCCCCTAG TGCTTCCGGAACCCCTGGGCAGAGGG TGACCATCTCATGCTCAGGTAGCTCC AGCAACATTGGAAACAATGCAGTTAA TTGGTATCAGCAACTGCCCGGGACCG CCCCAAAGCTTCTGATCTACGCTGAT AGTAATAGACCATCTGGAGTGCCTGA CAGATTCAGTGGTTCGAAAAGCGGCA CTTCTGCATCCTTGGCCATTTCTGGCT TAAGATCTGAAGATGAGGCCGACTAT TACTGTGGCTCTTGGGACTACTCCCTG AGCGGATATGTGTTTGGGGGCGGAAC TAAGCTCACAGTCCTAGGC (SEQ ID NO: 174) |
| SAIT-ANG-2-AB-8-A5 | GAGGTCCAGCTGCTCGAATCAGGCG GTGGGCTGGTGCAGCCAGGCGGCTC CCTGAGGTTAAGTTGCGCCGCTTCTG GCTTTACATTTAGCGATTATTACATG TCCTGGGTCCGCCAGGCCCCCGGGA AAGGTCTGGAGTGGGTGAGCGGAAT TTACCCTTCCGGGGGAAGCACCTAT TACGCGGATTCTGTAAAGGGTAGAT TCACTATCTCAAGAGACAATTCTAA GAATACCCTGTATTTGCAGATGAAC AGTCTTAGAGCCGAAGACACAGCAG TTTATTATTGTGCAAGAGACCCCAGT ACTCTAACCTACGCTGGCTTCGATTA CTGGGGACAAGGAACGCTCGTGACA GTGTCAAGC (SEQ ID NO: 175) | CAAAGTGTTCTCACACAGCCGCCATC CGCTTCCGGGACCCCTGGACAGAGAG TGACCATCAGTTGTAGTGGCTCTTCGA GCAATATTGGCAATAACTATGTGACA TGGTATCAGCAGCTTCCTGGAACAGC CCCCAAACTGCTCATCTATGCCGACA GCCACAGACCATCAGGTGTCCCCGAT AGATTTTCTGGGTCAAAGTCAGGAAC TAGCGCAAGCCTGGCCATTTCTGGAT TAAGGTCCGAGGACGAAGCTGATTAC TATTGCGCAACTTGGGACTACTCTCTG TCTGGTTACGTGTTCGGCGGCGGAAC CAAGTTGACGGTCCTAGGC (SEQ ID NO: 176) |

TABLE 13-continued

| antibody | Amino acid sequence of heavy chain variable region | Amino acid sequence of light chain variable region |
|---|---|---|
| SAIT-ANG-2-AB-7-C9 | GAGGTGCAACTCCTGGAGTCAGGAG<br>GCGGCCTGGTCCAGCCCGGCGGGAG<br>TCTTAGACTCTCGTGTGCCGCAAGC<br>GGGTTTACATTCAGTAACTACGCCA<br>TGTCCTGGGTCAGACAGGCTCCTGG<br>AAAGGGACTGGAATGGGTTTCTGCC<br>ATTAGCTCCGGCGGAGGTAATATCT<br>ATTACGCTGATTCCGTTAAAGGGAG<br>GTTTACAATCTCTCGGGATAACAGC<br>AAAAATACTTTGTATCTGCAGATGA<br>ATAGCTTAAGAGCCGAAGACACTGC<br>AGTGTACTACTGCGCGAAGAGCGGT<br>ATTCAACCCTCTCCACCATCCATGTC<br>ATCAGCTTATGCAATGGACGTATGG<br>GGGCAGGGCACCCTGGTGACCGTGA<br>GTTCT (SEQ ID NO: 177) | CAGAGCGTCCTGACACAACCTCCATC<br>CGCTTCTGGGACGCCTGGACAGAGAG<br>TGACAATTTCTTGCAGCGGCTCATCTT<br>CAAATATTGGAAACAATGACGTTTAT<br>TGGTACCAGCAGCTCCCAGGGACCGC<br>CCCAAAGCTGCTGATCTATGCAAACT<br>CACACAGACCCAGCGGAGTGCCCGAT<br>AGATTCAGTGGATCCAAATCCGGCAC<br>TAGTGCCAGCTTGGCAATCTCGGGGC<br>TGAGATCTGAAGACGAGGCTGATTAC<br>TATTGTGGTACCTGGGATTACTCCTTA<br>AGTGGTTACGTGTTTGGCGGGGGCAC<br>TAAGCTTACCGTCCTAGGC (SEQ ID<br>NO: 178) |
| SAIT-ANG-2-AB-4-C11 | GAAGTACAGCTGCTGGAGTCGGGTG<br>GTGGACTGGTTCAGCCAGGAGGCTC<br>ATTAAGGCTGAGCTGCGCCGCAAGC<br>GGTTTCACTTTTTCTGATTATGCTAT<br>GTCCTGGGTCAGACAGGCCCCTGGG<br>AAGGGACTCGAGTGGGTCTCAAGTA<br>TTTACCCCGACGATGGAAATACCTA<br>CTATGCCGATAGCGTGAAGGGGCGC<br>TTTACAATCTCTAGAGATAATTCTAA<br>AAACACCCTGTACCTTCAAATGAAC<br>TCATTGCGGGCAGAAGACACAGCGG<br>TGTACTATTGTGCTAGACACACGTCC<br>CACCATACCAGCATCGACGGCTACT<br>ATTATTACGGGATGGACGGCTGGGG<br>CCAGGGCACTCTCGTGACAGTGTCC<br>AGT (SEQ ID NO: 179) | CAGTCAGTCCTGACTCAGCCACCCTC<br>CGCAAGCGGGACACCTGGACAAAGA<br>GTTACTATCTCTTGCACCGGGTCAAGC<br>TCCAATATCGGTAACAATGATGTGAG<br>TTGGTACCAGCAGTTACCAGGCACCG<br>CCCCGAAACTGCTTATTTACTCAGAC<br>AGCAAAAGACCCTCTGGCGTGCCTGA<br>CAGATTCTCAGGAAGCAAGAGTGGCA<br>CGTCTGCTTCCTTGGCCATTTCGGGTC<br>TGAGATCCGAGGACGAAGCTGATTAT<br>TATTGTGGAAGCTGGGATTATAGTCT<br>GTCTGGCTACGTGTTTGGGGGCGGAA<br>CCAAGCTCACAGTCCTAGGC (SEQ ID<br>NO: 180) |
| IT-ANG-2-AB-4-F5 | GAGGTGCAGTTGCTCGAGTCCGGGG<br>GTGGCCTGGTGCAGCCAGGAGGAAG<br>CCTGAGACTGAGCTGCGCAGCCTCA<br>GGTTTCACATTCTCCGATTACGACAT<br>GTCCTGGGTTAGGCAAGCCCCCGGC<br>AAGGGGCTGGAATGGGTAAGCTCTA<br>TCAGCCACGGCGACAGTAACAAATA<br>TTATGCAGACTCTGTTAAGGGACGG<br>TTTACCATTTCACGCGATAACTCAAA<br>GAATACACTGTACCTTCAAATGAAT<br>AGTCTCAGAGCTGAAGATACCGCCG<br>TGTATTACTGTGCTAAATCGTCCGGA<br>ATCCAGGAGAGTCCCCCTACTTATT<br>ACTACTATGGGATGGATGTGTGGGG<br>CCAGGGCACCCTGGTCACTGTCTCTT<br>CTGCTAGC (SEQ ID NO: 181) | CAGTCTGTGTTGACCCAGCCCCCTTCT<br>GCATCTGGCACCCCCGGACAGAGAGT<br>CACTATAAGTTGTTCTGGTAGCTCCTC<br>AAATATCGGCTCAAACGCCGTGAATT<br>GGTACCAGCAATTACCAGGAACAGCT<br>CCTAAGCTGCTTATCTATGCAGACAG<br>TAACAGACCAAGCGGCGTTCCTGATA<br>GATTCTCAGGCTCCAAGTCCGGGACT<br>AGTGCCTCGCTGGCTATTAGCGGTCTC<br>AGAAGTGAAGATGAGGCCGATTACTA<br>TTGCGGAAGCTGGGACTACTCCCTGA<br>GCGGCTATGTGTTTGGAGGAGGGACA<br>AAACTCACCGTCCTAGGC (SEQ ID NO:<br>182) |
| SAIT-ANG-2-AB-4-F11 | GAGGTGCAACTGCTGGAGAGTGGTG<br>GGGGCCTTGTTCAGCCCGGCGGATC<br>CTTGAGGCTGTCATGCGCTGCGTCTG<br>GCTTTACTTTCAGCGATTACGCAATG<br>AGTTGGGTGAGACAGGCTCCAGGAA<br>AAGGCCTGGAATGGGTCAGCTCCAT<br>TTATCCTGACGATGGTAACACATATT<br>ACGCCGACAGCGTAAAAGGACGGTT<br>CACCATCTCTCGCGATAATTCTAAG<br>AACACCCTGTATCTCCAGATGAATA<br>GCCTGAGAGCAGAAGACACCGCCGT<br>GTACTACTGTGCCAAGCATCCTGTG<br>AGATTAAACCTGCACCCAATGTACT<br>ATTATTACGGCATGGACGTTTGGGG<br>GCAGGGGACACTCGTGACTGTCTCC<br>TCA (SEQ ID NO: 183) | CAGTCTGTGTTAACACAACCTCCAAG<br>TGCATCCGGAACGCCGGGCCAGAGAG<br>TGACTATCAGCTGCACCGGCAGCTCG<br>TCCAATATCGGTAACAACGCAGTTAG<br>TTGGTACCAGCAGCTTCCCGGCACAG<br>CTCCAAAGCTCTTGATTTACAGCGATT<br>CACAAAGACCTAGTGGTGTCCCCGAT<br>AGATTTTCTGGGAGTAAGAGCGGGAC<br>CAGTGCCTCCCTGGCTATATCAGGAC<br>TGAGATCTGAAGATGAGGCTGACTAT<br>TACTGTGCCACTTGGGACTATTCACTC<br>TCTGCCTATGTGTTCGGGGGCGGAAC<br>CAAACTGACAGTCCTAGGC (SEQ ID<br>NO: 184) |
| SAIT-ANG-2-AB-4-H10 | GAGGTTCAGTTGCTGGAGAGTGGCG<br>GCGGCTTAGTGCAGCCAGGTGGCAG<br>CCTGCGCCTTTCTTGTGCCGCCAGTG<br>GGTTTACCTTCTCCTCCTACGACATG<br>AGCTGGGTGCGGCAGGCTCCCGGCA<br>AAGGTCTTGAATGGGTGTCACTGAT<br>CAGCCCTGACAGTTCCTCAATCTATT<br>ATGCAGATTCAGTCAAGGGAAGATT | CAGAGCGTGCTCACCCAACCTCCCAG<br>TGCATCCGGAACGCCTGGTCAGAGAG<br>TGACAATTAGCTGCTCAGGGTCTTCCT<br>CTAACATCGGGTCCAATTATGTCAATT<br>GGTATCAGCAGTTGCCAGGTACAGCT<br>CCCAAACTGCTGATCTACAGTGATTC<br>CCACAGACCTAGCGGCGTTCCAGACA<br>GATTTAGCGGATCCAAGTCGGGAACT |

TABLE 13-continued

| antibody | Amino acid sequence of heavy chain variable region | Amino acid sequence of light chain variable region |
|---|---|---|
| | TACCATAAGCAGAGATAATTCCAAG AATACTCTGTACCTACAGATGAACT CGCTCAGAGCCGAAGATACCGCAGT CTACTACTGCGCTAAAGACCTGATTT CTTTCTGGAGGGGGGGATTCGACTA TTGGGGGCAAGGAACACTCGTAACA GTGTCTAGC (SEQ ID NO: 185) | TCTGCAAGCCTCGCTATTTCTGGCCTG AGAAGTGAGGACGAAGCCGATTATTA CTGTGGGGCCTGGGACGATTCATTAT CAGGATACGTGTTCGGAGGCGGCACC AAGCTTACTGTCCTAGGC (SEQ ID NO: 186) |
| SAIT-ANG-2-AB-3-D3 | GAGGTACAGCTGCTGGAAAGTGGGG GCGGTCTGGTGCAGCCAGGGGGAAG CCTCCGGCTTTCATGCGCCGCAAGC GGCTTTACATTCAGTGACTATGACAT GAGTTGGGTCCGACAAGCCCCCGGA AAGGGCCTGGAGTGGGTGTCTGGAA TCTCCTCCGATGACGGCAATACTTAT TACGCTGACTCCGTTAAAGGTAGGT TCACCATCTCTCGCGATAACTCTAA AAACACCCTCTACCTGCAGATGAAT AGCTTGAGGGCAGAAGATACGGCTG TCTACTATTGTGCCAGACCTACAATT GACAAGTACACATTAAGAGGGTATT ATTCATACGGCATGGATGTTTGGGG ACAGGGAACTCTAGTGACCGTGTCC AGC (SEQ ID NO: 187) | CAGTCAGTGCTGACACAGCCTCCAAG CGCTTCCGGGACACCTGGACAAAGAG TTACCATTTCGTGCACCGGATCCTCCT CAAACATCGGTAGCAATTATGTGTCT TGGTACCAGCAGCTCCCCGGGACTGC CCCCAAACTCTTGATCTACAGCGACA ACAAGAGACCATCTGGTGTGCCTGAT AGATTCAGTGGGAGTAAGTCAGGAAC GAGTGCCTCTCTGGCTATTTCTGGCCT GAGAAGCGAAGATGAGGCAGACTATT ATTGTGGCACCTGGGATGACTCCCTG AATGGCTACGTCTTTGGCGGCGGAAC AAAACTTACTGTCCTAGGC(SEQ ID NO: 188) |

2.8. Ang2:Tie2 Neutralization ELISA (Competitive ELISA)

To verify molecular interaction of the bound assemblies, a competitive ELISA was performed. A 96-well MaxiSorp™ flat-bottom plate (Nunc) was coated with 4 μg/μl of hTie2-Fc (R&D Systems), which is a protein with the Fc of human IgG1 bound thereto. After that, the plate was washed five times with 0.05% (v/v) Tween-20-containing PBS (Phosphate Buffer Saline) and then blocked with 1% (v/v) BSA (Bovine serum albumin; Sigma)-containing PBS at a room temperature for 2 hours.

To perform Ang2:Tie2 neutralization ELISA, the anti-Ang2 antibodies in their IgG forms purified in Example 2 (0.00, 0.01, 0.1, 1, 10, 100, and 1000 nM) were added to each well of the plate coated with hTie2-Fc, along with 1% (v/v) BSA and 400 ng/ml of FLAG-Tagged hAng2 and then, the plate was allowed to react at a room temperature for 2 hours. Thereafter, the plate was washed five times with 0.05% Tween-20-containing PBS and then, an HRP-conjugated anti-FLAG antibody (SIGMA) diluted in 1% (v/v) BSA-containing PBS at 1:5,000 ratio (v/v) was added in the amount of 100 μl to each well to react at a room temperature for 1 hour, followed by washing five times with 0.1% (v/v) Tween-20-containing PBS. Finally, 100 μl of TMB substrate (cell signal) was added to each well of the plate to induce color development at a room temperature for 3 min. Then, the reaction was ceased by the addition of 50 μl of 5N $H_2SO_4$ solution and OD450 values were measured on a plate reader (Molecular Devices). Through them, 50% inhibition concentrations (IC50) against Ang2:Tie2 binding were obtained and shown in the following Table 14.

TABLE 14

| antibody | 50% inhibition concentration against Ang2:Tie2 binding ($IC_{50}$, nM) |
|---|---|
| SAIT-ANG-2-AB-2-E6 | 0.605 |
| SAIT-ANG-2-AB-4-H10 | 0.417 |
| SAIT-ANG-2-AB-8-A5 | 0.341 |
| SAIT-ANG-2-AB-7-C9 | 0.392 |
| SAIT-ANG-2-AB-3-D3 | 0.44 |

TABLE 14-continued

| antibody | 50% inhibition concentration against Ang2:Tie2 binding ($IC_{50}$, nM) |
|---|---|
| SAIT-ANG-2-AB-4-C11 | 0.421 |
| SAIT-ANG-2-AB-4-F5 | 1.525 |
| SAIT-ANG-2-AB-4-F11 | 0.37 |

As in Table 14 above, it was confirmed that the anti-Ang2 antibodies can neutralize binding between Ang2 and Tie2 receptors.

2.9. Binding ELISA of mAng2

To measure binding of the antibodies prepared above with each antigen, ELISA was performed. A 96-well MaxiSorp™ flat-bottom plate (Nunc) was coated with 5~20 μg/ml of human Ang2 and mouse Ang2 (Accession #NP_031452) (both, R&D Systems). After that, the plate was washed five times with 0.05% (v/v) Tween-20-containing PBS and then blocked with 1% (v/v) BSA-containing PBS at a room temperature for 2 hours. The anti-Ang2 antibodies in their IgG forms prepared above (0.001, 0.01, 0.1, 1, 10, 100, and 1000 nM) were added to each well of the plate which was then allowed to react at a room temperature for 2 hours.

Thereafter, the plate was washed five times with 0.05% Tween-20-containing PBS and then, an HRP-conjugated anti-human FC (Anti-hFc-HRP conjugated) antibody (SIGMA) diluted in 1% (v/v) BSA-containing PBS at 1:5,000 ratio (v/v) was added in the amount of 50 μl to each well to react at a room temperature for 1 hour, followed by washing five times with 0.1% (v/v) Tween-20-containing PBS. Finally, 100 μl of TMB substrate (cell signal) was added to each well of the plate to induce color development at a room temperature for 3 min and then, the reaction was ceased by the addition of 50 μl of 5N $H_2SO_4$ solution and OD450 values were measured on a plate reader (Molecular Devices). By obtaining 50% binding concentrations (Kd) to human Ang2 and mouse Ang2 proteins through them, the binding degrees of the anti-Ang2 antibodies to each antigen were measured. The obtained results are shown in the following Table 15.

TALE 15

| antibody | mouse Ang2 (Kd, nM) |
|---|---|
| SAIT-ANG-2-AB-2-E6 | 0.35 |
| SAIT-ANG-2-AB-4-H10 | 0.21 |
| SAIT-ANG-2-AB-8-A5 | 0.19 |
| SAIT-ANG-2-AB-3-D3 | 0.30 |
| SAIT-ANG-2-AB-4-C11 | 0.28 |
| SAIT-ANG-2-AB-4-F11 | 0.36 |

2.10. Antigen Affinity (Kd values) Measurement Using Surface Plasmon Resonance (SPR) Method To measure accurate affinities toward an anti-Ang2 antigen, antigen affinities were measured by a SPR method using a BIAcore T100 (GE Healthcare). The SPR method uses refractive index change of light which passes a sensor chip according to the state of materials coated onto the sensor chip, and if an antigen or an antibody is flowed onto a chip coated with the antigen or antibody, it causes changes in refractive index due to their binding and Kd values are thus calculated from the measured values.

First, anti-His antibody was immobilized on a CMS sensor chip (GE healthcare) up to 8,000 RU levels using a pH 5.0 acetate solution and an amine coupling kit (GE Healthcare). 6 μg/ml of a recombinant hAng2 (C-His, R&D Systems) protein was flowed onto the chip to be captured at 100 to 200 RU levels. The antibodies obtained in Example 2 above were diluted serially to twice each time starting from 100 nM concentration and each of them was flowed onto the chip to allow them to be bound to (on), dissociated from (off), and regenerated (using 10 mM NaOH solution) from the antigen captured on the sensor chip, thereby to measure antigen-antibody affinities. The results are as shown in the following Table 16.

TABLE 16

| antibody | On rate (l/Ms) | Off Rate (l/s) | Affinity (Kd, nM) |
|---|---|---|---|
| SAIT-ANG-2-AB-2-E6 | $1.220 \times 10^6$ | $7.950 \times 10^{-4}$ | 0.65 |
| SAIT-ANG-2-AB-4-H10 | $2.812 \times 10^6$ | $3.328 \times 10^{-4}$ | 0.118 |
| SAIT-ANG-2-AB-8-A5 | $4.396 \times 10^6$ | $3.266 \times 10^{-4}$ | 0.074 |
| SAIT-ANG-2-AB-7-C9 | $1.785 \times 10^6$ | $3.661 \times 10^{-4}$ | 0.205 |
| SAIT-ANG-2-AB-3-D3 | $1.162 \times 10^6$ | $5.461 \times 10^{-4}$ | 0.47 |
| SAIT-ANG-2-AB-4-C11 | $8.327 \times 10^5$ | $4.899 \times 10^{-4}$ | 0.588 |
| SAIT-ANG-2-AB-4-F5 | $1.895 \times 10^6$ | 0.001117 | 0.589 |
| SAIT-ANG-2-AB-4-F11 | $1.765 \times 10^6$ | $7.774 \times 10^{-4}$ | 0.44 |

2.11. Test of Ang2 Receptor Inhibitory Activity of Ang2 Antibodies

As Ang2 induces a change in vascular endothelial cells by binding to a Tie2 receptor expressed in the vascular endothelial cells to induce the phosphorylation of the receptor and activate it, the Ang2 inhibitory activities of the anti-Ang2 antibodies were verified through the functional analysis of the antibodies using a cell-based assay.

For this, $1\times10^6$ of HUVEC (ATCC) cells (Kim et al., *Biochim Bioohys Acta.,* 2009) were cultured in a 60 mm culture dish using 5% (v/v) FBS (Gibco)-added EGM-2 (Endothelial growth media) media (Lonza) at 37° C. and when they reached 80~90% confluency, the media were replaced with serum-free EGM-2 media and cultured at 37° C. for 16 hours. The dish was washed once with PBS and after the replacement with 0.1 nM sodium orthovanadate-mixed EGM-2 media, they were further cultured for 10 min. After washed once with PBS, the cultured cells were treated with a mixture prepared by mixing the anti-Ang2 antibodies prepared in Example 2 at a 10 μg/ml concentration with 2 μg/ml human Ang2 protein (R&D systems) and letting them stand for 20 min and further cultured for 10 min.

The cells were washed using a cold PBS, treated with 300 μl of lysis buffer (Roche), collected to a tube to allow them to be dissolved at 4° C. for 30 min. and then, centrifuged at 13,000 rpm for 15 min. to measure a supernatant. 2 μg of anti Tie2 antibody (R&D system) was added to 0.5 mg of a cell lysate, which was then overnight reacted at 4° C. and then subjected to immunoprecipitation by the addition of protein A bead (GE Healthcare) thereto.

The reactant obtained above was centrifuged at 13,000 rpm for 15 min. to obtain a pellet, which was washed two to three times with lysis buffer (Roche), added to a sample buffer (Invitrogen) mixed with a reducing agent, and boiled at 95° C. for 5 min., and then, applied to NuPAGE Novex 4-12% Bis-Tris gel (Invitrogen) and transferred onto Nitrocellulose membrane (Invitrogen).

To verify the presence of the phosphorylation of Tie2, the above blots were blocked with PBST mixed with 3% (v/v) skim milk (Sigma) for 30 min. and identified using an HRP-conjugated anti-phospho tyrosine antibody (Millipore). For Tie2 identification, the blots were reacted in a stripping buffer (Thermo) for 15 min and then blocked again and identified using an anti Tie2 antibody (Santa cruz). After band intensities were measured using Image J software (http://rsb.info.nih.gov/ij/index.html), the inhibitory degrees of Tie2 phosphorylation after the treatment of the anti-Ang2 antibodies were calculated in relative % against the Ang2 single treatment group, and the results are shown in the following Table 17.

TABLE 17

| Antibody (treated amount: 50 nM) | Tie2 phosphorylation inhibition (%) |
|---|---|
| SAIT-ANG-2-AB-4-H10 | 69% |
| SAIT-ANG-2-AB-8-A5 | 60% |
| SAIT-ANG-2-AB-2-E6 | 62% |

2.12. Inhibition Test of Binding between Ang2 and Integrin

An ELISA plate was coated with a diluting solution of integrin (alpha5beta1 (α5β1 (α5: NCBI Accession No. P08648, β1: NCBI Accession No. P05556); R&D systems) protein diluted in PBS at a concentration of 5 μg/ml (18 hours, 4° C.) and then blocked with 1% (v/v) BSA at a room temperature for 2 hours. Thereafter, the plate was treated with Ang2 protein (FLAG-Ang2, 0.05 ml of Ang2 protein solution diluted in PBS at a concentration of 10 μg/ml) tagged with a FLAG sequence (DYKDDDDK SEQ ID NO: 201, Sigma) at N-terminal and an antibody (0.05 ml of antibody solution diluted in PBS at a concentration of 10 μg/ml) at the same time, incubated at a room temperature for 2 hours, and washed five times with PBS-t (0.1% (v/v) triton X-100 in PBS). After that, an anti-FLAG antibody (Sigma) conjugated with horseradish peroxidase (HRP) was added to react, and the plate was washed again five times with PBS-t. Bindings between Ang2 and the above the integrin were identified indirectly by measuring the amounts of the anti-FLAG antibody remaining in the ELISA plate via color development using TMB (3,3,5,5-tetramethylbenzidine) as a substrate of HRP. As positive controls, control antibody 1 (Regeneron Ang2 antibody) and control antibody 2 (Astra Zeneca Ang2 antibody) were used. Also, to show the background, a group coated with BSA instead of integrin was used.

Figure 2:
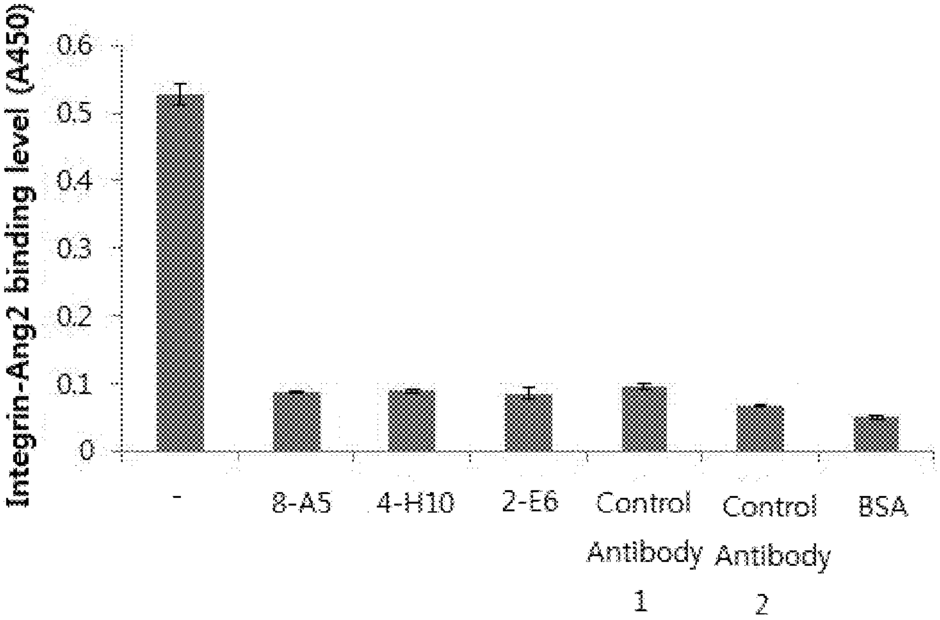
FIG. 2 is a graph showing the inhibition of binding between Ang2 and integrin by treatment of an anti-Ang2 antibody according to an embodiment (control antibody 1: Regeneron Ang2 antibody; control antibody 2: Astra Zeneca Ang2 antibody).

The results obtained above were shown in FIG. 2. As seen in FIG. 2, the anti-Ang2 antibodies provided in the invention remarkably suppressed binding between integrin and Ang2.

Example 1

Preparation of an Anti-c-Met/anti-Ang2 Bispecific Antibody

The anti-Ang2 scFv obtained on Reference Example 2 was fused to the C-terminus of Fc of the anti-c-Met antibody L3-1Y-IgG2 prepared in Reference Example 1, to prepare a bispecific antibody.

The heavy chain part of L3-1Y-IgG2 antibody which was used in the bispecific antibody cloning was prepared as follows. A DNA fragment encoding the heavy chain of the anti-c-Met antibody was synthesized by deleting the part encoding C-terminus part from position 1393 of SEQ ID NO: 67 and inserting "ggcggtggtggttccggaggcggcggatcc" (SEQ ID NO: 202) instead of the deleted part (Bioneer Corporation). Thereafter, the DNA fragment was ligated to a vector from the pOptiVEC™-TOPO TA Cloning Kit included in OptiCHO™ Antibody Express Kit (Cat no. 12762-019) (Invitrogen).

An anti-Ang2 scFv was prepared by linking the heavy chain variable region (SEQ ID NO: 162) and the light chain variable region (SEQ ID NO: 170) of anti-Ang2 antibody 4-H10 via a peptide linker $(GGGGS)_2$. In particular, a nucleotide sequence (SEQ ID NO: 185) encoding the heavy chain variable region of anti-Ang2 antibody 4-H10, a nucleotide sequence (SEQ ID NO: 186) encoding the light chain variable region of anti-Ang2 antibody 4-H10, and a nucleotide sequence encoding the peptide linker were all synthesized by Bioneer Corporation (in the form including a N-terminal BamHI restriction site and C-terminal XhoI restriction site).

Then, the obtained anti-Ang2 scFv was cloned in the prepared L3-1Y-IgG2 containing vector using restriction enzymes BamHI and XhoI, to construct an expression vector for the heavy chain of the bispecific antibody.

Each region of the amino acid sequence (SEQ ID NO: 189) encoding the heavy chain of the bispecific antibody (wherein the heavy chain of the c-Met antibody and the anti-Ang2 scFv are linked through the peptide linker) is summarized in following Table 18:

TABLE 18

| SEQ ID NO: 189<br>N-terminus → C-terminus | |
|---|---|
| Signal peptide | MEWSWVFLVTLLNGIQC (SEQ ID NO: 192) |
| Heavy chain variable region of anti-c-Met antibody | EVQLVESGGGLVQPGGSLRLSCAASGFTFTDYYMSWVRQAP GKGLEWLGFIRNKANGYTTEYSASVKGRFTISRDNSKNTLYL QMNSLRAEDTAVYYCARDNWFAYWGQGTLVTVSS (SEQ ID NO: 193) |
| Fc (IgG2) | ASTKGPSVFPLAPCSRSTSESTAALGCLVKDYFPEPVTVSWNS GALTSGVHTFPAVLQSSGLYSLSSVVTVPSSNFGTQTYTCNVD HKPSNTKVDKTVERKCCVECPPCPAPPVAGPSVFLFPPKPKDT LMISRTPEVTCVVVDVSHEDPEVQFNWYVDGVEVHNAKTKP REEQFNSTFRVVSVLTVVHQDWLNGKEYKCKVSNKGLPAPIE KTISKTKGQPREPQVYTLPPSREEMTKNQVSLTCLVKGFYPSDI AVEWESNGQPENNYKTTPPMLDSDGSFFLYSKLTVDKSRWQ QGNVFSCSVMHEALHNHYTQKSLSLSPG (SEQ ID NO: 194) |
| Peptide linker (linking the C-terminus of Fcand the anti-Ang2 scFv) | GGGGSGGGGS (SEQ ID NO: 195) |
| Heavy chain variable region of the anti-Ang2 scFv | EVQLLESGGGLVQPGGSLRLSCAASGFTFSSYDMSWVRLAPG KGLEWVSLISPDSSSIYYADSVKGRFTISRDNSKNTLYLQMNS LRAEDTAVYYCAKDLISFWRGGFDYWGQGTLVTVSS (SEQ ID NO: 196) |
| Peptide linker (linking the heavy chain variable region and the light chain variable region of the anti-Ang2 scFv) | GGGGSGGGGS (SEQ ID NO: 197) |
| Light chain variable region of the anti-Ang2 scFv | QSVLTQPPSASGTPGQRVTISCSGSSSNIGSNYVNWYQQLPGT APKLLIYSDSHRPSGVPDRFSGSKSGTSASLAISGLRSEDEADY YCGAWDDSLSGYVFGGGTKLTVLGQAGQHHHHHHGAYPYD VPDYAS (SEQ ID NO: 198) |

(CDRs are underlined)

In addition, the DNA fragment encoding the light chain of the anti-c-Met antibody was synthesized so that it has the nucleotide sequence of SEQ ID NO: 69 (Bioneer Corporation). The DNA fragment encoding the light chain of the anti-c-Met antibody was inserted into a vector from the pcDNA™ 3.3-TOPO TA Cloning Kit (Cat no. 8300-01) included in OptiCHO™ Antibody Express Kit (Cat no. 12762-019) (Invitrogen), to construct an expression vector for the light chain of the anti-c-Met antibody.

Each region of the amino acid sequence (SEQ ID NO: 68) encoding the light chain of the anti-c-Met antibody is summarized in following Table 19:

TABLE 19

| SEQ ID NO: 68<br>N-terminus → C-terminus | |
|---|---|
| Signal peptide | MDSQAQVLMLLLLSVSGTCG (SEQ ID NO: 199) |

TABLE 19-continued

| | SEQ ID NO: 68<br>N-terminus → C-terminus |
|---|---|
| Light chain variable region of the anti-c-Met antibody | DIQMTQSPSSLSASVGDRVTITCKSSQSLLA SGNQNNYLAWYQQKPGKAPKMLIIWASTR VSGVPSRFSGSGSGTDFTLTISSLQPEDFATYY CQQSYSRPYTFGQGTKVEIKRTVAAPSVFIFPPS DEQLKSGTASVVCLLNNFYPREAKVQWKVDNA LQSGNSQESVTEQDSKDSTYSLSSTLT LSKADYEKHKVYACEVTHQGLSSPVTKSF NRGEC (SEQ ID NO: 200) |

(CDRs are underlined)

Each of the constructed expression vectors for the heavy chain and the light chain was amplified using Qiagen Maxiprep kit (Cat no. 12662), and a temporary expression was performed using Freestyle™ MAX 293 Expression System (Invitrogen). For the expression, 293F cells were used and subjected to a suspension culture using FreeStyle™ 293 Expression Medium. One day before the temporary expression, the cells were provided at the amount of $5\times10^5$ cells/ml, and 24 hours after, when the number of the cells reaches $1\times10^6$ cells/ml, the temporary expression was performed. A transfection was performed by liposomal reagent method using Freestyle™ MAX reagent (Invitrogen). In 15 ml tube, the DNA fragments encoding the heavy chain and the light chain were provided at the ratio of 1:1 (heavy chain DNA: light chain DNA), and mixed with 2 ml of OptiPro™ SFM (Invtrogen) (mixture (A)). In another 15 ml tube, 100 ml of Freestyle™ MAX reagent and 2 ml of OptiPro™ SFM 2 ml were mixed (mixture (B)). Then mixtures (A) and (B) were mixed and incubated for 15 minutes, and the obtained mixture was slowly added to and mixed with the cell provided one day before. After the transfection was completed, the cells were incubated for 4 days under the conditions of 37° C., 80% humidity, and 8% $CO_2$ in 130 rpm incubator.

The incubated cells were centrifuged and 100 ml of each supernatant was collected and purified using AKTA Prime (GE Healthcare). AKTA Prime was equipped with HiTrap MabSelect SuRe column (GE Healthcare, 11-0034-95). The cell culture solution was flowed at the flow rate of 5 ml/min, and then, eluted with IgG elution buffer (Thermo Scientific, 21004), and the obtained eluate was exchanged with PBS buffer.

Finally, an antibody wherein the anti-Ang2 scFv is fused to the C-terminus of the anti-c-Met antibody L3-1Y-IgG2 was obtained and named as an anti-c-Met/anti-Ang2 bispecific antibody (referred to in the figures as "BS ab").

Example 2

Binding Affinity of the anti-c-Met/anti-Ang2 Bispecific Antibody to c-Met

The binding affinity of the anti-c-Met/anti-Ang2 bispecific antibody prepared in Example 1 to c-Met was measured using Biacore T100 (GE). For this, a human Fab binder (GE Healthcare) was fixed on the surface of CMS chip (#BR-1005-30, GE) according to manufacturer's manual. About 90~120 RU of the anti-c-Met/anti-Ang2 bispecific antibody was captured and then, c-Met-Fc (#358-MT/CF, R&D Systems) was added to the captured antibody at various concentrations. Hereto, 10 mM Glycine-HCl (pH 1.5) solution was added, to regenerate the surface. To measure the affinity, the above obtained data were fitted using BIAevaluation software (GE Healthcare, Biacore T100 evaluation software).

The obtained results are illustrated in Table 20:

TABLE 20

| $R_{max}$ (RU) | $K_D$ (nM) | $k_a$ (l/Ms) | $k_d$ (l/s) | $Chi^2$ | U-Value | T ($k_a$) | T ($k_d$) |
|---|---|---|---|---|---|---|---|
| 65.40 | 0.09 | $8.5\times10^5$ | $8.2\times10^{-5}$ | 4.04 | 15 | $9.1\times10^2$ | 54 |

As shown in Table 20, the bispecific antibody prepared in Example 1 shows the high affinity (about 0.09 nM) to c-Met.

Example 3

Binding Affinity of the anti-c-Met/anti-Ang2 Bispecific Antibody to Ang2

An ELISA for measuring the binding affinity of the anti-c-Met/anti-Ang2 bispecific antibody prepared in Example 1 to Ang2 was performed. 96-well MaxiSorp™ flat-bottom plate (Nunc) was coated with 1 μg/μl of human Ang2 (R&D Systems) at the amount of 50 ul/well. Thereafter, the plate was washed 5 times with 0.05% Tween-20-containing phosphate buffer saline (PBS) and blocked with 1% BSA-containing PBS for 2 hours at room temperature. The anti-c-Met/anti-Ang2 bispecific antibody prepared in Example 1 was added to the Ang2-coated well, and allowed to react for 1 hour at room temperature. The anti-c-Met/anti-Ang2 bispecific antibody was used by serially diluting from $10^4$ nM (see FIG. 3). Then, the well was washed 5 times with 0.05% Tween-20-containing PBS, and then, reacted with HRP-conjugated anti-Human Fc antibody (Sigma) that is diluted with 1% BSA-containing PBS to the ratio of 1:5,000, for 1 hour at room temperature, and then washed 5 times with 0.1% Tween-20-containing PBS. Finally, 100 μl of TMB substrate (SIGMA) was added to each well of the plate, to induce coloring response. Then, the response was stopped using 50 μl of 5N $H_2SO_4$ solution. The value of OD450 was measured on a plate reader (Molecular Devices). The binding affinity to Ang2 was obtained by determining the 50% binding concentrations to human Ang2 protein from the above results.

Figure 3:
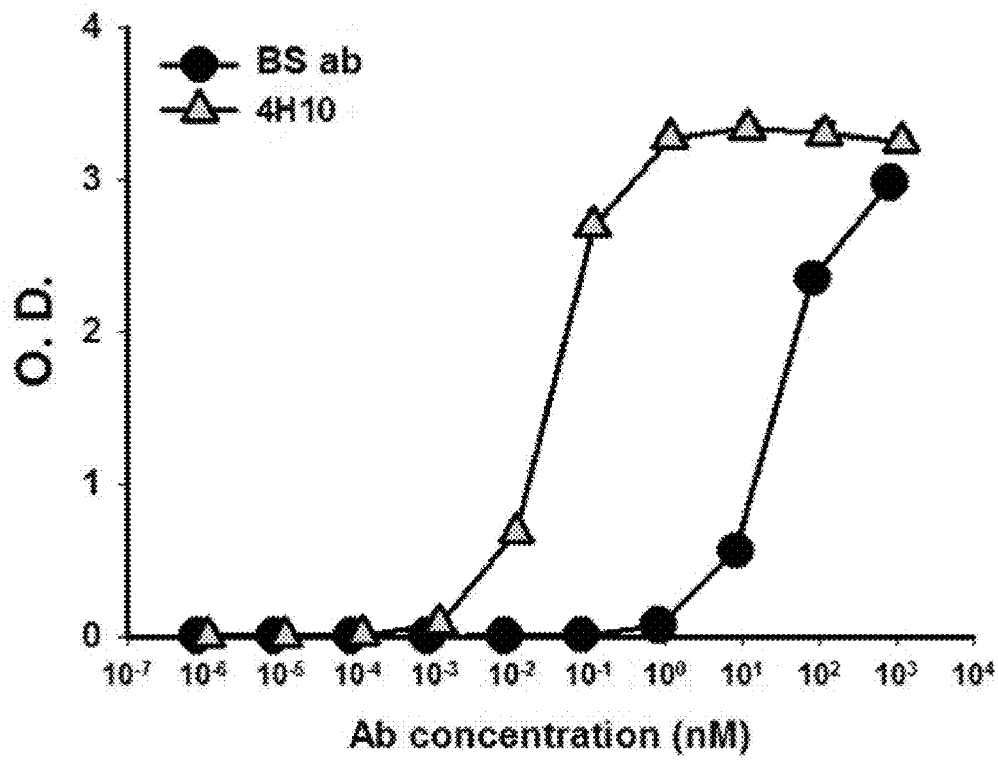
FIG. 3 is a graph showing the binding affinity of an anti-c-Met/anti-Ang2 bispecific antibody according to an embodiment to Ang2.

The obtained results are illustrated in Table 21 and FIG. 3:

TABLE 21

| | Kd (nM) |
|---|---|
| BS Ab | 31 |
| Anti-Ang2 Ab (4-H10) | 0.035 |

(BS ab: the anti-c-Met/anti-Ang2 bispecific antibody of Example 1)

As shown in Table 21 and FIG. 3, the bispecific antibody prepared in Example 1 has binding affinity to Ang2 of about 31 nM.

Example 4

Growth Inhibition of Vascular Cells by the Anti-c-Met/anti-Ang2 Bispecific Antibody To verify the effect of the anti-c-Met/anti-Ang2 bispecific antibody prepared in Example 1 on vascular cell growth, Cell Counting Kit-8 (CCK-8, supplied by Dojinho Molecular Technologies, Inc. Cat. #CK04-01) was used.

CCK-8 enables sensitive colorimetric assay, thereby achieving an exact measurement of cell viability in cell proliferation and cytotoxicity assay. A highly water-soluble tetrazolium salt, WST-8 [2-(2-methoxy-4-nitrophenyl)-3-(4-nitrophenyl)-5-(2,4-disulfophenyl)-2H-tetrazolium, monosodium salt; referring to the following chemical formula] is reduced by a dehydrogenase activity in a cell to be yellow formazan dye which can be dissolved in a tissue culturing medium.

The amount of formazan dye generated by dehydrogenase activity in a cell is direct proportional to the number of living cells, and thus, the cell viability can be determined by measuring the amount of formazan dye. In this example, it was tested how much the anti-c-Met/anti-Ang2 bispecific antibody or each inhibitor inhibits the cell growth which is increased by treating Ang2 and c-Met ligand, HGF/SF.

In particular, the vascular cell growth inhibition effect of the anti-c-Met/anti-Ang2 bispecific antibody prepared in Example 1 was tested in human umbilical vein endothelial cells (HUVEC) and lymphatic endothelial cells (LEC). The HUVEC cells were obtained from ATCC and the LEC cells were obtained from Lonza.

The cells were cultured in EGM-2 medium (Lonza) under the conditions of 5% $CO_2$ and 37° C. For a cell proliferation assay, the cells (5000 cells/well, 0.5% FBS in EBM2) were subcultured in 96 well plate, wherein the cells were treated with the anti-c-Met/anti-Ang2 bispecific antibody prepared in Example 1 at the amount of 2 μg/ml (40 nM) and cultured for 72 hours. 100 μg/ml of HGF (#294-HG/CF, R&D SYSTEMS, Minneapolis, Minn.) was treated to the culture together. As a negative control, a medium which is not treated with the antibody was used, and as positive controls, groups treated with 4-H10 anti-Ang2 antibody prepared in Reference Example 2, treated with L3-1Y-IgG2 antibody prepared in Reference Example 1, and co-treated with L3-1Y-IgG2 antibody and 4-H10 antibody were used, wherein each antibody was used at the amount of 60 nM (in the case of co-treatment, each antibody was treated the amount of 60 nM).

After the culture, the degree of cell proliferation was analyzed using Cell Counting Kit-8 assay (Dojindo Molecular Technologies, Gaithersburg, Md.) according to the manufacturer's manual. In brief, after the 72 hour culture, CCK8 solution was added to each well at the amount of 10 μl, and then, the cells were further cultured for 2.5 hours. Then, the absorbance at 450 nm was measured with microplate reader.

Figure 4:
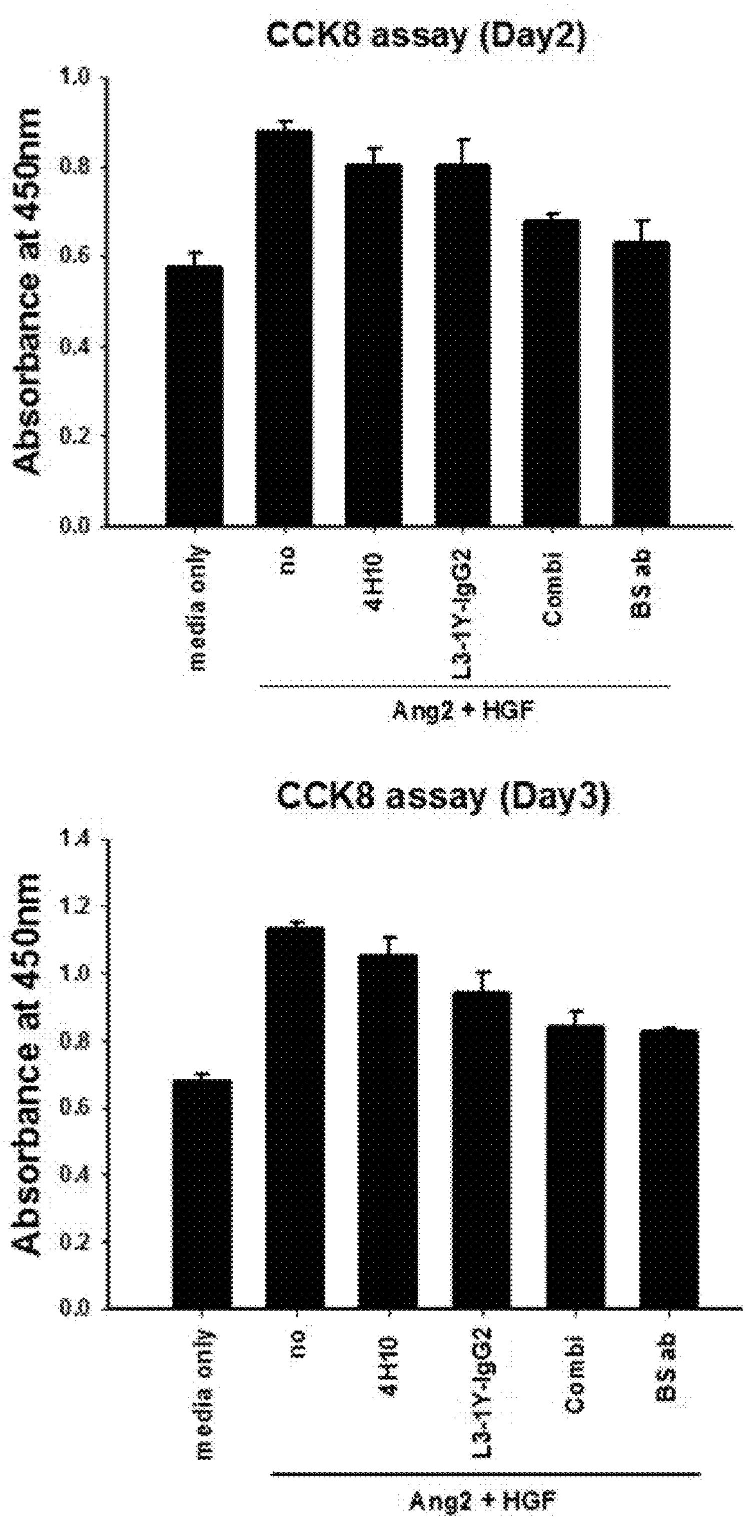
FIG. 4 is a graph showing the inhibition of cell (HUVEC) growth by treatment of an anti-c-Met/anti-Ang2 bispecific antibody according to an embodiment. A CCK8 assay was performed at day 2 or day 3 with added media only, or with stimulation by Ang2 and the c-Met ligand, HGF/SF. For the stimulated cells, the following were added: no antibody control ("no"), 4H10 antibody, L3-1Y-IgG2 antibody, a combination of 4H10 and L3-1Y-IgG2 antibodies ("Combi") or the bispecific antibody ("BS ab").
Figure 5:
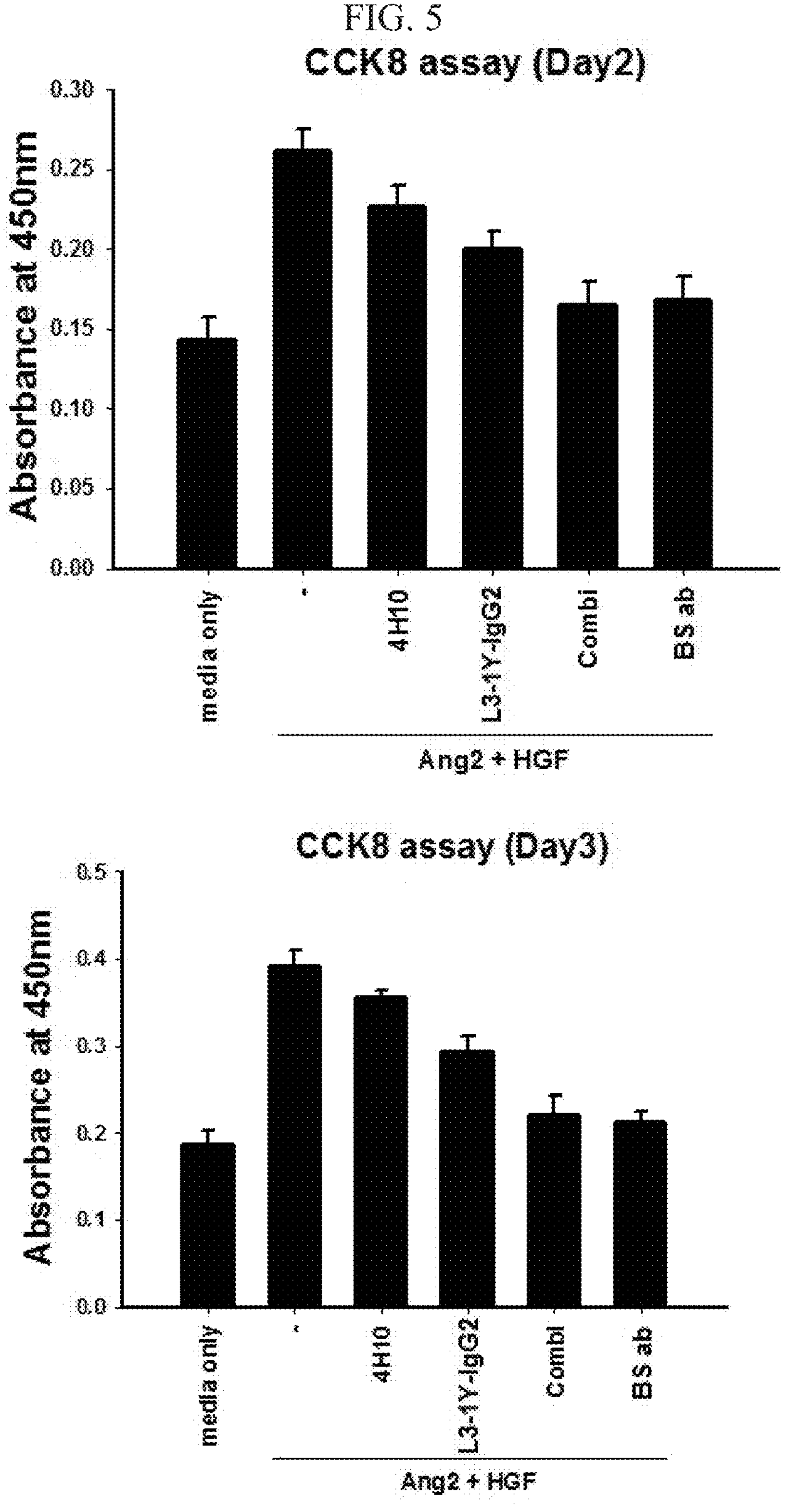
FIG. 5 is a graph showing the inhibition of cell (LEC) growth by treatment of an anti-c-Met/anti-Ang2 bispecific antibody according to an embodiment. A CCK8 assay was performed at day 2 or day 3 with added media only, or with stimulation by Ang2 and the c-Met ligand, HGF/SF. For the stimulated cells, the following were added: no antibody control ("-"), 4H10 antibody, L3-1Y-IgG2 antibody, a combination of 4H10 and L3-1Y-IgG2 antibodies ("Combi") or the bispecific antibody ("BS ab").

The obtained results were illustrated in FIG. 4 (for HUVEC) and FIG. 5 (for LEC). As shown in FIGS. 4 and 5, the anti-c-Met/anti-Ang2 bispecific antibody exhibits cell proliferation inhibitory effect which is considerable increased compared with the anti-c-Met antibody L3-1Y-IgG2 or the anti-Ang2 antibody 4-H10, and which is equal to or higher than that of the co-treatment of the anti-c-Met antibody L3-1Y-IgG2 or the anti-Ang2 antibody 4-H10.

Example 5

Inhibition of Cell Migration by the Anti-c-Met/anti-Ang2 Bispecific Antibody Since Ang2 and c-Met are both related to cancer metastasis as well as cancer cell proliferation, the effect of the anti-c-Met/anti-Ang2 bispecific antibody prepared in Example 1 on cell motility was observed. The inhibition effect of the bispecific antibody on HUVEC migration by Ang2+HGF was tested as follows:

The motility of endothelial cells was measured using xCelligence RTCA (Realtime cell analyzer; GE Healthcare). The RTCA is a non-invasive cell monitoring system capable of measuring impedance in real-time thereby determining changes of cells. For the cell migration assay, CIM-plate16 (GE Healthcare) consisting of a lower chamber and a upper chamber was used, wherein microelectrodes for measuring the impedance are arranged on the upper chamber, whereby when the cells seeded on the chamber migrate through micropores, the migration degree of cells attached to the microelectrodes can be confirmed. The migration degree was converted as a migration index. HUVEC cells (HUVEC P3-6, ATCC) which were grown in EGM-2 medium (Lonza) were incubated in 1% FBS-containing EBM medium for 6 hours.

To each well of the lower chamber of the CIM-plate16 including 2% FBS-containing EBM medium, HGF 100 ng/ml and Ang2 2 ug/ml were added together with 4H10 antibody (Reference Example 2), L3-1Y-IgG1 antibody (Reference Example 1), a combination of 4H10 and L3-1Y-IgG1, or the anti-c-Met/anti-Ang2 bispecific antibody (Example 1), wherein each antibody was used at the concentration of 100 nM (in the case of combination, each antibody was used at the concentration of 100 nM), and then, assembled with the upper chamber coated with fibronectin (Sigma). Serum free EBM medium was added to the upper chamber at the amount of 30 μl, and then, left in incubator for 1 hour for equilibration between the plate and the medium. The CIM-plate was equipped in a device station in the incubator and then, the background value was measured.

The incubated HUVEC cells were re-suspended with EBM-2 Serum-free media (Lonza), seeded at the amount of 60,000 cells/well, left for 15 minutes to be settle down, and then equipped in the device, to measure the cell migration degree in real-time. The cell migration degree was expressed as Slope (1/hr).

Figure 6:
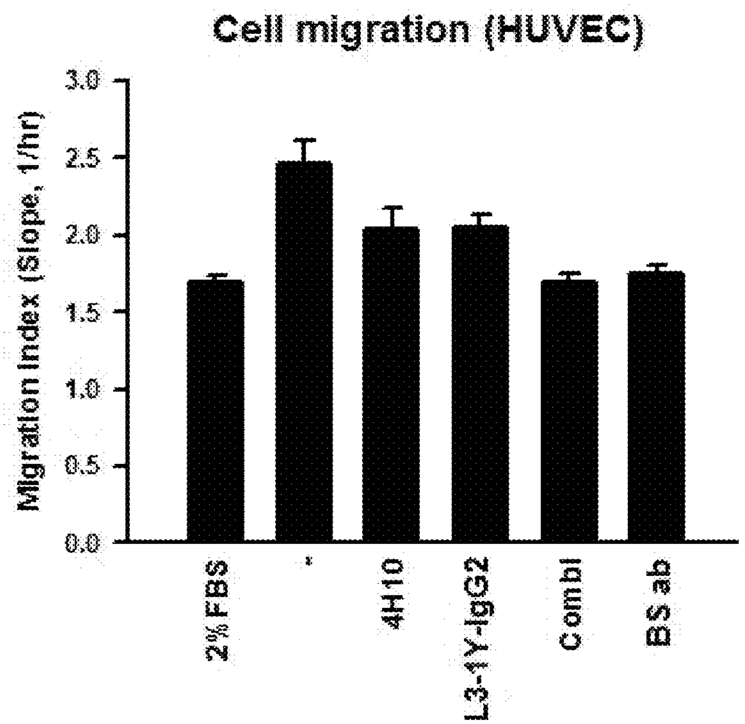
FIG. 6 is a graph showing the inhibition of cell migration by treatment of an anti-c-Met/anti-Ang2 bispecific antibody according to an embodiment. The migration assay was performed with added 2% FBS-containing EBM media only ("2% FBS"), or with stimulation by Ang2 and the c-Met ligand, HGF. For the stimulated cells, the following were added: no antibody control ("-"), 4H10 antibody, L3-1Y-IgG2 antibody, a combination of 4H10 and L3-1Y-IgG2 antibodies ("Combi") or the bispecific antibody ("BS ab").

The obtained results are illustrated in FIG. 6. As shown in FIG. 6, the anti-c-Met/anti-Ang2 bispecific antibody exhibits an inhibitory effect on HUVEC migration by Ang2+HGF wherein the inhibitory effect is considerably increased compared with that of L3-1Y-IgG2 or 4-H10 alone, and equal to or higher than that of a combination of L3-1Y-IgG2 and 4-H10.

While one or more embodiments of the present invention have been described with reference to the figures, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising,"

"having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An anti-c-Met/anti-Ang2 bispecific antibody comprising: (a) an anti-c-Met antibody or an antigen-binding fragment thereof and (b) an anti-Ang2 antibody or an antigen-binding fragment thereof, wherein the anti-Ang2 antibody or an antigen-binding fragment thereof comprises:

(a) a CDR-H1 comprising SEQ ID NO: 109, a CDR-H2 comprising SEQ ID NO: 115, and a CDR-H3 comprising SEQ ID NO: 122;
and
a CDR-L1 comprising SEQ ID NO: 130, a CDR-L2 comprising SEQ ID NO: 138; and a CDR-L3 comprising SEQ ID NO: 145;

(b) a CDR-H1 comprising SEQ ID NO: 110, a CDR-H2 comprising SEQ ID NO: 116, and a CDR-H3 comprising SEQ ID NO: 123;
and
a CDR-L1 comprising SEQ ID NO: 131, a CDR-L2 comprising SEQ ID NO: 139; and a CDR-L3 comprising SEQ ID NO: 146;

(c) a CDR-H1 comprising SEQ ID NO: 111, a CDR-H2 comprising SEQ ID NO: 117, and a CDR-H3 comprising SEQ ID NO: 124;
and
a CDR-L1 comprising SEQ ID NO: 132, a CDR-L2 comprising SEQ ID NO: 140; and a CDR-L3 comprising SEQ ID NO: 147;

(d) a CDR-H1 comprising SEQ ID NO: 109, a CDR-H2 comprising SEQ ID NO: 118, and a CDR-H3 comprising SEQ ID NO: 125;
and
a CDR-L1 comprising SEQ ID NO: 133, a CDR-L2 comprising SEQ ID NO: 141; and a CDR-L3 comprising SEQ ID NO: 145;

(e) a CDR-H1 comprising SEQ ID NO: 112, a CDR-H2 comprising SEQ ID NO: 119, and a CDR-H3 comprising SEQ ID NO: 126;
and
a CDR-L1 comprising SEQ ID NO: 134, a CDR-L2 comprising SEQ ID NO: 138; and a CDR-L3 comprising SEQ ID NO: 145;

(f) a CDR-H1 comprising SEQ ID NO: 109, a CDR-H2 comprising SEQ ID NO: 118, and a CDR-H3 comprising SEQ ID NO: 127;
and
a CDR-L1 comprising SEQ ID NO: 135, a CDR-L2 comprising SEQ ID NO: 142; and a CDR-L3 comprising SEQ ID NO: 148; or (g) a CDR-H1 comprising SEQ ID NO: 113, a CDR-H2 comprising SEQ ID NO: 120, and a CDR-H3 comprising SEQ ID NO: 128;
and
a CDR-L1 comprising SEQ ID NO: 136, a CDR-L2 comprising SEQ ID NO: 143; and a CDR-L3 comprising SEQ ID NO: 149.

2. The anti-c-Met/anti-Ang2 bispecific antibody of claim 1, wherein the anti-Ang2 antibody or an antigen-binding fragment thereof comprises:

(a) a heavy chain variable region comprising SEQ ID NO: 156;
and a light chain variable region comprising SEQ ID NO: 164;

(b) a heavy chain variable region comprising SEQ ID NO: 157;
and a light chain variable region comprising SEQ ID NO: 165;

(c) a heavy chain variable region comprising SEQ ID NO: 158;
and a light chain variable region comprising SEQ ID NO: 166;

(d) a heavy chain variable region comprising SEQ ID NO: 159;
and a light chain variable region comprising SEQ ID NO: 167;

(e) a heavy chain variable region comprising SEQ ID NO: 160;
and a light chain variable region comprising SEQ ID NO: 168;

(f) a heavy chain variable region comprising SEQ ID NO: 161;
and a light chain variable region comprising SEQ ID NO: 169; or (g) a heavy chain variable region comprising SEQ ID NO: 162;

and a light chain variable region comprising SEQ ID NO: 170.

3. The anti-c-Met/anti-Ang2 bispecific antibody of claim 1, comprising an anti-c-Met antibody that comprises two heavy chains and two light chains, and an anti-Ang2 scFv linked to the C-terminus of the anti-c-Met antibody.

4. A pharmaceutical composition comprising the anti-c-Met/anti-Ang2 bispecific antibody of claim 1 and a pharmaceutically acceptable carrier.

5. A method of treating a disease associated with c-Met or Ang2 in a subject, the method comprising administering the anti-c-Met/anti-Ang2 bispecific antibody of claim 1 to the subject, wherein the a disease associated with c-Met or Ang2 is cancer or cancer metastasis.

* * * * *

SEQUENCE LISTING

```
<160> NUMBER OF SEQ ID NOS: 202

<210> SEQ ID NO 1
<211> LENGTH: 5
<212> TYPE: PRT
<213> ORGANISM: Artificial Sequence
<220> FEATURE:
<223> OTHER INFORMATION: Synthetic (heavy chain CDR1 of AbF46)

<400> SEQUENCE: 1

Asp Tyr Tyr Met Ser
1               5


<210> SEQ ID NO 2
<211> LENGTH: 19
<212> TYPE: PRT
<213> ORGANISM: Artificial Sequence
<220> FEATURE:
<223> OTHER INFORMATION: Synthetic (heavy chain CDR2 of AbF46)

<400> SEQUENCE: 2

Phe Ile Arg Asn Lys Ala Asn Gly Tyr Thr Thr Glu Tyr Ser Ala Ser
1               5                   10                  15

Val Lys Gly


<210> SEQ ID NO 3
<211> LENGTH: 6
<212> TYPE: PRT
<213> ORGANISM: Artificial Sequence
<220> FEATURE:
<223> OTHER INFORMATION: Synthetic (heavy chain CDR3 of AbF46)

<400> SEQUENCE: 3

Asp Asn Trp Phe Ala Tyr
1               5


<210> SEQ ID NO 4
<211> LENGTH: 6
<212> TYPE: PRT
<213> ORGANISM: Artificial Sequence
<220> FEATURE:
<223> OTHER INFORMATION: Synthetic (heavy chain CDR1 of c-Met antibody)
<220> FEATURE:
<221> NAME/KEY: MOD_RES
<222> LOCATION: (1)
<223> OTHER INFORMATION: Xaa is Pro or Ser or absent
<220> FEATURE:
<221> NAME/KEY: MOD_RES
<222> LOCATION: (2)
<223> OTHER INFORMATION: Xaa is Glu or Asp
```

<400> SEQUENCE: 4

Xaa Xaa Tyr Tyr Met Ser
1 5

<210> SEQ ID NO 5
<211> LENGTH: 8
<212> TYPE: PRT
<213> ORGANISM: Artificial Sequence
<220> FEATURE:
<223> OTHER INFORMATION: Synthetic (heavy chain CDR2 of c-Met antibody)
<220> FEATURE:
<221> NAME/KEY: MOD_RES
<222> LOCATION: (3)
<223> OTHER INFORMATION: Xaa is Asn or Lys
<220> FEATURE:
<221> NAME/KEY: MOD_RES
<222> LOCATION: (4)
<223> OTHER INFORMATION: Xaa is Ala or Val
<220> FEATURE:
<221> NAME/KEY: MOD_RES
<222> LOCATION: (7)
<223> OTHER INFORMATION: Xaa is Asn or Thr

<400> SEQUENCE: 5

Arg Asn Xaa Xaa Asn Gly Xaa Thr
1 5

<210> SEQ ID NO 6
<211> LENGTH: 6
<212> TYPE: PRT
<213> ORGANISM: Artificial Sequence
<220> FEATURE:
<223> OTHER INFORMATION: Synthetic (heavy chain CDR3 of c-Met antibody)
<220> FEATURE:
<221> NAME/KEY: MOD_RES
<222> LOCATION: (5)
<223> OTHER INFORMATION: Xaa is Ser or Thr

<400> SEQUENCE: 6

Asp Asn Trp Leu Xaa Tyr
1 5

<210> SEQ ID NO 7
<211> LENGTH: 17
<212> TYPE: PRT
<213> ORGANISM: Artificial Sequence
<220> FEATURE:
<223> OTHER INFORMATION: Synthetic (light chain CDR1 of c-Met antibody)
<220> FEATURE:
<221> NAME/KEY: MOD_RES
<222> LOCATION: (4)
<223> OTHER INFORMATION: Xaa is His, Arg, Gln or Lys
<220> FEATURE:
<221> NAME/KEY: MOD_RES
<222> LOCATION: (9)
<223> OTHER INFORMATION: Xaa is Ser or Trp
<220> FEATURE:
<221> NAME/KEY: MOD_RES
<222> LOCATION: (12)
<223> OTHER INFORMATION: Xaa is His or Gln
<220> FEATURE:
<221> NAME/KEY: MOD_RES
<222> LOCATION: (13)
<223> OTHER INFORMATION: Xaa is Lys or Asn

<400> SEQUENCE: 7

Lys Ser Ser Xaa Ser Leu Leu Ala Xaa Gly Asn Xaa Xaa Asn Tyr Leu
1 5 10 15

Ala

<210> SEQ ID NO 8
<211> LENGTH: 7
<212> TYPE: PRT
<213> ORGANISM: Artificial Sequence
<220> FEATURE:
<223> OTHER INFORMATION: Synthetic (light chain CDR2 of c-Met antibody)
<220> FEATURE:
<221> NAME/KEY: MOD_RES
<222> LOCATION: (2)
<223> OTHER INFORMATION: Xaa is Ala or Gly
<220> FEATURE:
<221> NAME/KEY: MOD_RES
<222> LOCATION: (4)
<223> OTHER INFORMATION: Xaa is Thr or Lys
<220> FEATURE:
<221> NAME/KEY: MOD_RES
<222> LOCATION: (7)
<223> OTHER INFORMATION: Xaa is Ser or Pro

<400> SEQUENCE: 8

Trp Xaa Ser Xaa Arg Val Xaa
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic (light chain CDR3 of c-Met antibody)
<220> FEATURE:
<221> NAME/KEY: MOD_RES
<222> LOCATION: (1)
<223> OTHER INFORMATION: Xaa is Gly, Ala or Gln
<220> FEATURE:
<221> NAME/KEY: MOD_RES
<222> LOCATION: (6)
<223> OTHER INFORMATION: Xaa is Arg, His, Ser, Ala, Gly or Lys
<220> FEATURE:
<221> NAME/KEY: MOD_RES
<222> LOCATION: (8)
<223> OTHER INFORMATION: Xaa is Leu, Tyr, Phe or Met

<400> SEQUENCE: 9

Xaa Gln Ser Tyr Ser Xaa Pro Xaa Thr
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic (light chain CDR1 of AbF46)

<400> SEQUENCE: 10

Lys Ser Ser Gln Ser Leu Leu Ala Ser Gly Asn Gln Asn Asn Tyr Leu
1               5                   10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic (light chain CDR2 of AbF46)

<400> SEQUENCE: 11

Trp Ala Ser Thr Arg Val Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic (light chain CDR3 of AbF46)

<400> SEQUENCE: 12

Gln Gln Ser Tyr Ser Ala Pro Leu Thr
1 5

<210> SEQ ID NO 13
<211> LENGTH: 9
<212> TYPE: PRT
<213> ORGANISM: Artificial Sequence
<220> FEATURE:
<223> OTHER INFORMATION: Synthetic (CDR-L3 derived from L3-1 clone)

<400> SEQUENCE: 13

Gln Gln Ser Tyr Ser Arg Pro Tyr Thr
1 5

<210> SEQ ID NO 14
<211> LENGTH: 9
<212> TYPE: PRT
<213> ORGANISM: Artificial Sequence
<220> FEATURE:
<223> OTHER INFORMATION: Synthetic (CDR-L3 derived from L3-2 clone)

<400> SEQUENCE: 14

Gly Gln Ser Tyr Ser Arg Pro Leu Thr
1 5

<210> SEQ ID NO 15
<211> LENGTH: 9
<212> TYPE: PRT
<213> ORGANISM: Artificial Sequence
<220> FEATURE:
<223> OTHER INFORMATION: Synthetic (CDR-L3 derived from L3-3 clone)

<400> SEQUENCE: 15

Ala Gln Ser Tyr Ser His Pro Phe Ser
1 5

<210> SEQ ID NO 16
<211> LENGTH: 9
<212> TYPE: PRT
<213> ORGANISM: Artificial Sequence
<220> FEATURE:
<223> OTHER INFORMATION: Synthetic (CDR-L3 derived from L3-5 clone)

<400> SEQUENCE: 16

Gln Gln Ser Tyr Ser Arg Pro Phe Thr
1 5

<210> SEQ ID NO 17
<211> LENGTH: 117
<212> TYPE: PRT
<213> ORGANISM: Artificial Sequence
<220> FEATURE:
<223> OTHER INFORMATION: Synthetic (heavy chain variable region of anti
c-Met humanized antibody(huAbF46-H4))

<400> SEQUENCE: 17

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Thr Asp Tyr

-continued

```
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115


<210> SEQ ID NO 18
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg


<210> SEQ ID NO 19
<211> LENGTH: 114
<212> TYPE: PRT
<213> ORGANISM: Artificial Sequence
<220> FEATURE:
<223> OTHER INFORMATION: Synthetic (light chain variable region of anti
      c-Met humanized antibody(huAbF46-H4))

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80
```

-continued

Ile Ser Ser Leu Gln Pro Glu Asp Phe Ala Thr Tyr Tyr Cys Gly Gln
85 90 95

Ser Tyr Ser Arg Pro Leu Thr Phe Gly Gln Gly Thr Lys Val Glu Ile
100 105 110

Lys Arg

<210> SEQ ID NO 20
<211> LENGTH: 114
<212> TYPE: PRT
<213> ORGANISM: Artificial Sequence
<220> FEATURE:
<223> OTHER INFORMATION: Synthetic (light chain variable region of anti c-Met humanized antibody(huAbF46-H4))

<400> SEQUENCE: 20

Asp Ile Gln Met Thr Gln Ser Pro Ser Ser Leu Ser Ala Ser Val Gly
1 5 10 15

Asp Arg Val Thr Ile Thr Cys Lys Ser Ser Gln Ser Leu Leu Ala Ser
20 25 30

Gly Asn Gln Asn Asn Tyr Leu Ala Trp His Gln Gln Lys Pro Gly Lys
35 40 45

Ala Pro Lys Met Leu Ile Ile Trp Ala Ser Thr Arg Val Ser Gly Val
50 55 60

Pro Ser Arg Phe Ser Gly Ser Gly Ser Gly Thr Asp Phe Thr Leu Thr
65 70 75 80

Ile Ser Ser Leu Gln Pro Glu Asp Phe Ala Thr Tyr Tyr Cys Ala Gln
85 90 95

Ser Tyr Ser His Pro Phe Ser Phe Gly Gln Gly Thr Lys Val Glu Ile
100 105 110

Lys Arg

<210> SEQ ID NO 21
<211> LENGTH: 114
<212> TYPE: PRT
<213> ORGANISM: Artificial Sequence
<220> FEATURE:
<223> OTHER INFORMATION: Synthetic (light chain variable region of anti c-Met humanized antibody(huAbF46-H4)

<400> SEQUENCE: 21

Asp Ile Gln Met Thr Gln Ser Pro Ser Ser Leu Ser Ala Ser Val Gly
1 5 10 15

Asp Arg Val Thr Ile Thr Cys Lys Ser Ser Gln Ser Leu Leu Ala Ser
20 25 30

Gly Asn Gln Asn Asn Tyr Leu Ala Trp His Gln Gln Lys Pro Gly Lys
35 40 45

Ala Pro Lys Met Leu Ile Ile Trp Ala Ser Thr Arg Val Ser Gly Val
50 55 60

Pro Ser Arg Phe Ser Gly Ser Gly Ser Gly Thr Asp Phe Thr Leu Thr
65 70 75 80

Ile Ser Ser Leu Gln Pro Glu Asp Phe Ala Thr Tyr Tyr Cys Gln Gln
85 90 95

Ser Tyr Ser Arg Pro Phe Thr Phe Gly Gln Gly Thr Lys Val Glu Ile
100 105 110

Lys Arg

<210> SEQ ID NO 22

-continued

<211> LENGTH: 6
<212> TYPE: PRT
<213> ORGANISM: Artificial Sequence
<220> FEATURE:
<223> OTHER INFORMATION: Synthetic (CDR-H1 derived from H11-4 clone)

<400> SEQUENCE: 22

Pro Glu Tyr Tyr Met Ser
1 5

<210> SEQ ID NO 23
<211> LENGTH: 6
<212> TYPE: PRT
<213> ORGANISM: Artificial Sequence
<220> FEATURE:
<223> OTHER INFORMATION: Synthetic (CDR-H1 derived from YC151 clone)

<400> SEQUENCE: 23

Pro Asp Tyr Tyr Met Ser
1 5

<210> SEQ ID NO 24
<211> LENGTH: 6
<212> TYPE: PRT
<213> ORGANISM: Artificial Sequence
<220> FEATURE:
<223> OTHER INFORMATION: Synthetic (CDR-H1 derived from YC193 clone)

<400> SEQUENCE: 24

Ser Asp Tyr Tyr Met Ser
1 5

<210> SEQ ID NO 25
<211> LENGTH: 8
<212> TYPE: PRT
<213> ORGANISM: Artificial Sequence
<220> FEATURE:
<223> OTHER INFORMATION: Synthetic (CDR-H2 derived from YC244 clone)

<400> SEQUENCE: 25

Arg Asn Asn Ala Asn Gly Asn Thr
1 5

<210> SEQ ID NO 26
<211> LENGTH: 8
<212> TYPE: PRT
<213> ORGANISM: Artificial Sequence
<220> FEATURE:
<223> OTHER INFORMATION: Synthetic (CDR-H2 derived from YC321 clone)

<400> SEQUENCE: 26

Arg Asn Lys Val Asn Gly Tyr Thr
1 5

<210> SEQ ID NO 27
<211> LENGTH: 6
<212> TYPE: PRT
<213> ORGANISM: Artificial Sequence
<220> FEATURE:
<223> OTHER INFORMATION: Synthetic (CDR-H3 derived from YC354 clone)

<400> SEQUENCE: 27

Asp Asn Trp Leu Ser Tyr
1 5

<210> SEQ ID NO 28
<211> LENGTH: 6

-continued

<212> TYPE: PRT
<213> ORGANISM: Artificial Sequence
<220> FEATURE:
<223> OTHER INFORMATION: Synthetic (CDR-H3 derived from YC374 clone)

<400> SEQUENCE: 28

Asp Asn Trp Leu Thr Tyr
1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic (CDR-L1 derived from L1-1 clone)

<400> SEQUENCE: 29

Lys Ser Ser His Ser Leu Leu Ala Ser Gly Asn Gln Asn Asn Tyr Leu
1               5                   10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic (CDR-L1 derived from L1-3 clone)

<400> SEQUENCE: 30

Lys Ser Ser Arg Ser Leu Leu Ser Ser Gly Asn His Lys Asn Tyr Leu
1               5                   10                  15

Ala

<210> SEQ ID NO 31
<211> LENGTH: 17
<212> TYPE: PRT
<213> ORGANISM: Artificial Sequence
<220> FEATURE:
<223> OTHER INFORMATION: Synthetic (CDR-L1 derived from L1-4 clone)

<400> SEQUENCE: 31

Lys Ser Ser Lys Ser Leu Leu Ala Ser Gly Asn Gln Asn Asn Tyr Leu
1               5                   10                  15

Ala

<210> SEQ ID NO 32
<211> LENGTH: 17
<212> TYPE: PRT
<213> ORGANISM: Artificial Sequence
<220> FEATURE:
<223> OTHER INFORMATION: Synthetic (CDR-L1 derived from L1-12 clone)

<400> SEQUENCE: 32

Lys Ser Ser Arg Ser Leu Leu Ala Ser Gly Asn Gln Asn Asn Tyr Leu
1               5                   10                  15

Ala

<210> SEQ ID NO 33
<211> LENGTH: 17
<212> TYPE: PRT
<213> ORGANISM: Artificial Sequence
<220> FEATURE:
<223> OTHER INFORMATION: Synthetic (CDR-L1 derived from L1-22 clone)

<400> SEQUENCE: 33

Lys Ser Ser His Ser Leu Leu Ala Ser Gly Asn Gln Asn Asn Tyr Leu
1 5 10 15

Ala

<210> SEQ ID NO 34
<211> LENGTH: 7
<212> TYPE: PRT
<213> ORGANISM: Artificial Sequence
<220> FEATURE:
<223> OTHER INFORMATION: Synthetic (CDR-L2 derived from L2-9 clone)

<400> SEQUENCE: 34

Trp Ala Ser Lys Arg Val Ser
1 5

<210> SEQ ID NO 35
<211> LENGTH: 7
<212> TYPE: PRT
<213> ORGANISM: Artificial Sequence
<220> FEATURE:
<223> OTHER INFORMATION: Synthetic (CDR-L2 derived from L2-12 clone)

<400> SEQUENCE: 35

Trp Gly Ser Thr Arg Val Ser
1 5

<210> SEQ ID NO 36
<211> LENGTH: 7
<212> TYPE: PRT
<213> ORGANISM: Artificial Sequence
<220> FEATURE:
<223> OTHER INFORMATION: Synthetic (CDR-L2 derived from L2-16 clone)

<400> SEQUENCE: 36

Trp Gly Ser Thr Arg Val Pro
1 5

<210> SEQ ID NO 37
<211> LENGTH: 9
<212> TYPE: PRT
<213> ORGANISM: Artificial Sequence
<220> FEATURE:
<223> OTHER INFORMATION: Synthetic (CDR-L3 derived from L3-32 clone)

<400> SEQUENCE: 37

Gln Gln Ser Tyr Ser Lys Pro Phe Thr
1 5

<210> SEQ ID NO 38
<211> LENGTH: 1416
<212> TYPE: DNA
<213> ORGANISM: Artificial Sequence
<220> FEATURE:
<223> OTHER INFORMATION: Synthetic (nucleotide sequence of heavy chain
of chAbF46)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:

<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 38
gaattcgccg ccaccatgga atggagctgg gtttttctcg taacactttt aaatggtatc 60
cagtgtgagg tgaagctggt ggagtctgga ggaggcttgg tacagcctgg gggttctctg 120
agactctcct gtgcaacttc tgggttcacc ttcactgatt actacatgag ctgggtccgc 180
cagcctccag gaaaggcact tgagtggttg ggttttatta gaaacaaagc taatggttac 240
acaacagagt acagtgcatc tgtgaagggt cggttcacca tctccagaga taattcccaa 300
agcatcctct atcttcaaat ggacaccctg agagctgagg acagtgccac ttattactgt 360
gcaagagata actggtttgc ttactggggc caagggactc tggtcactgt ctctgcagct 420
agcaccaagg gcccatcggt cttcccctg gcaccctcct ccaagagcac ctctgggggc 480
acagcggccc tgggctgcct ggtcaaggac tacttccccg aaccggtgac ggtgtcgtgg 540
aactcaggcg ccctgaccag cggcgtgcac accttcccgg ctgtcctaca gtcctcagga 600
ctctactccc tcagcagcgt ggtgaccgtg ccctccagca gcttgggcac ccagacctac 660
atctgcaacg tgaatcacaa gcccagcaac accaaggtgg acaagaaagt tgagcccaaa 720
tcttgtgaca aaactcacac atgcccaccg tgcccagcac ctgaactcct ggggggaccg 780
tcagtcttcc tcttcccccc aaaacccaag gacaccctca tgatctcccg gacccctgag 840
gtcacatgcg tggtggtgga cgtgagccac gaagaccctg aggtcaagtt caactggtac 900
gtggacggcg tggaggtgca taatgccaag acaaagccgc gggaggagca gtacaacagc 960
acgtaccgtg tggtcagcgt cctcaccgtc ctgcaccagg actggctgaa tggcaaggag 1020
tacaagtgca aggtctccaa caaagccctc ccagccccca tcgagaaaac catctccaaa 1080
gccaaagggc agccccgaga accacaggtg tacaccctgc ccccatcccg ggaggagatg 1140
accaagaacc aggtcagcct gacctgcctg gtcaaaggct tctatcccag cgacatcgcc 1200
gtggagtggg agagcaatgg gcagccggag aacaactaca agaccacgcc tcccgtgctg 1260
gactccgacg gctccttctt cctctacagc aagctcaccg tggacaagag caggtggcag 1320
caggggaacg tcttctcatg ctccgtgatg catgaggctc tgcacaacca ctacacgcag 1380
aagagcctct ccctgtctcc gggtaaatga ctcgag 1416

<210> SEQ ID NO 39
<211> LENGTH: 759
<212> TYPE: DNA
<213> ORGANISM: Artificial Sequence
<220> FEATURE:
<223> OTHER INFORMATION: Synthetic (nucleotide sequence of light chain
of chAbF46)
<220> FEATURE:
<221> NAME/KEY: misc_difference
<222> LOCATION: (1)..(6)
<223> OTHER INFORMATION: EcoRI restriction site
<220> FEATURE:

<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 39
gaattcacta gtgattaatt cgccgccacc atggattcac aggcccaggt cctcatgttg 60
ctgctgctat cggtatctgg tacctgtgga gacattttga tgacccagtc tccatcctcc 120
ctgactgtgt cagcaggaga gaaggtcact atgagctgca agtccagtca gagtctttta 180
gctagtggca accaaaataa ctacttggcc tggcaccagc agaaaccagg acgatctcct 240
aaaatgctga taatttgggc atccactagg gtatctggag tccctgatcg cttcataggc 300
agtggatctg ggacggattt cactctgacc atcaacagtg tgcaggctga agatctggct 360
gtttattact gtcagcagtc ctacagcgct ccgctcacgt tcggtgctgg gaccaagctg 420
gagctgaaac gtacggtggc tgcaccatct gtcttcatct tcccgccatc tgatgagcag 480
ttgaaatctg gaactgcctc tgttgtgtgc ctgctgaata acttctatcc cagagaggcc 540
aaagtacagt ggaaggtgga taacgccctc caatcgggta actcccagga gagtgtcaca 600
gagcaggaca gcaaggacag cacctacagc ctcagcagca ccctgacgct gagcaaagca 660
gactacgaga aacacaaagt ctacgcctgc gaagtcaccc atcagggcct gagctcgccc 720
gtcacaaaga gcttcaacag gggagagtgt tgactcgag 759

<210> SEQ ID NO 40
<211> LENGTH: 447
<212> TYPE: PRT
<213> ORGANISM: Artificial Sequence
<220> FEATURE:
<223> OTHER INFORMATION: Synthetic (amino acid sequence of H1-heavy)

<400> SEQUENCE: 40

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Thr Asp Tyr
20 25 30

Tyr Met Ser Trp Val Arg Gln Ala Pro Gly Lys Gly Leu Glu Trp Leu
35 40 45

Gly Phe Ile Arg Asn Lys Ala Asn Gly Tyr Thr Thr Glu Tyr Ser Ala
50 55 60

Ser Val Lys Gly Arg Phe Thr Ile Ser Arg Asp Asn Ser Lys Asn Ser
65 70 75 80

Leu Tyr Leu Gln Met Asn Ser Leu Lys Thr Glu Asp Thr Ala Val Tyr
85 90 95

Tyr Cys Ala Arg Asp Asn Trp Phe Ala Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Lys Val Glu Pro Lys Ser Cys Asp Lys Thr His
210 215 220

Thr Cys Pro Pro Cys Pro Ala Pro Glu Leu Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Lys
435 440 445

<210> SEQ ID NO 41
<211> LENGTH: 447
<212> TYPE: PRT
<213> ORGANISM: Artificial Sequence
<220> FEATURE:
<223> OTHER INFORMATION: Synthetic (amino acid sequence of H3-heavy)

<400> SEQUENCE: 41

Glu Val Gln Leu Val Glu Ser Gly Gly Gly Leu Val Gln Pro Gly Gly
1 5 10 15

-continued

```
Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430
```

-continued

His Asn His Tyr Thr Gln Lys Ser Leu Ser Leu Ser Pro Gly Lys
435 440 445

<210> SEQ ID NO 42
<211> LENGTH: 447
<212> TYPE: PRT
<213> ORGANISM: Artificial Sequence
<220> FEATURE:
<223> OTHER INFORMATION: Synthetic (amino acid sequence of H4-heavy)

<400> SEQUENCE: 42

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Thr Asp Tyr
20 25 30

Tyr Met Ser Trp Val Arg Gln Ala Pro Gly Lys Gly Leu Glu Trp Leu
35 40 45

Gly Phe Ile Arg Asn Lys Ala Asn Gly Tyr Thr Thr Glu Tyr Ser Ala
50 55 60

Ser Val Lys Gly Arg Phe Thr Ile Ser Arg Asp Asn Ser Lys Asn Thr
65 70 75 80

Leu Tyr Leu Gln Met Asn Ser Leu Arg Ala Glu Asp Thr Ala Val Tyr
85 90 95

Tyr Cys Ala Arg Asp Asn Trp Phe Ala Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Lys Val Glu Pro Lys Ser Cys Asp Lys Thr His
210 215 220

Thr Cys Pro Pro Cys Pro Ala Pro Glu Leu Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

-continued

```
Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 43
<211> LENGTH: 220
<212> TYPE: PRT
<213> ORGANISM: Artificial Sequence
<220> FEATURE:
<223> OTHER INFORMATION: Synthetic (amino acid sequence of H1-light)

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 44
<211> LENGTH: 220
<212> TYPE: PRT
<213> ORGANISM: Artificial Sequence
<220> FEATURE:
<223> OTHER INFORMATION: Synthetic (amino acid sequence of H2-light)

<400> SEQUENCE: 44
```

```
Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Ala Ser
            20                  25                  30

Gly Asn Gln Asn Asn Tyr Leu Ala Trp His Leu Gln Lys Pro Gly Gln
        35                  40                  45

Ser Pro Gln Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Ser Tyr Ser Ala Pro Leu Thr Phe Gly Gln Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 45
<211> LENGTH: 220
<212> TYPE: PRT
<213> ORGANISM: Artificial Sequence
<220> FEATURE:
<223> OTHER INFORMATION: Synthetic (amino acid sequence of H3-light)

<400> SEQUENCE: 45

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp Tyr Gln Gln Lys Pro Gly Gln
        35                  40                  45

Pro Pro Lys Leu Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140
```

```
Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 46
<211> LENGTH: 219
<212> TYPE: PRT
<213> ORGANISM: Artificial Sequence
<220> FEATURE:
<223> OTHER INFORMATION: Synthetic (amino acid sequence of H4-light)

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu
    210                 215


<210> SEQ ID NO 47
<211> LENGTH: 1350
<212> TYPE: DNA
<213> ORGANISM: Artificial Sequence
<220> FEATURE:
<223> OTHER INFORMATION: Synthetic (nucleotide sequence of H1-heavy)

<400> SEQUENCE: 47

gaggtgcagc tggtggagtc tgggggaggc ttggtccagc ctggagggtc cctgagactc      60
```

```
tcctgtgcag cctctggatt caccttcact gactactaca tgagctgggt ccgccaggct    120

ccagggaagg ggctggagtg gttgggcttt attagaaaca aagctaacgg ttacaccaca    180

gaatacagtg cgtctgtgaa aggcagattc accatctcaa gagataattc aaagaactca    240

ctgtatctgc aaatgaacag cctgaaaacc gaggacacgg ccgtgtatta ctgtgctaga    300

gataactggt ttgcttactg gggtcaagga accctggtca ccgtctcctc ggctagcacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga aagttgagcc caaatcttgt    660

gacaaaactc acacatgccc accgtgccca gcacctgaac tcctgggggg accgtcagtc    720

ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840

ggcgtggagg tgcataatgc caagacaaag ccgcgggagg agcagtacaa cagcacgtac    900

cgtgtggtca gcgtcctcac cgtcctgcac caggactggc tgaatggcaa ggagtacaag    960

tgcaaggtct ccaacaaagc cctcccagcc cccatcgaga aaaccatctc caaagccaaa   1020

gggcagcccc gagaaccaca ggtgtacacc ctgcccccat cccgggagga gatgaccaag   1080

aaccaggtca gcctgacctg cctggtcaaa ggcttctatc ccagcgacat cgccgtggag   1140

tgggagagca atgggcagcc ggagaacaac tacaagacca cgcctcccgt gctggactcc   1200

gacggctcct tcttcctcta cagcaagctc accgtggaca agagcaggtg gcagcagggg   1260

aacgtcttct catgctccgt gatgcatgag gctctgcaca accactacac gcagaagagc   1320

ctctccctgt ctccgggtaa atgactcgag                                    1350
```

<210> SEQ ID NO 48
<211> LENGTH: 1350
<212> TYPE: DNA
<213> ORGANISM: Artificial Sequence
<220> FEATURE:
<223> OTHER INFORMATION: Synthetic (nucleotide sequence of H3-heavy)

<400> SEQUENCE: 48

```
gaggtgcagc tggtggagtc tgggggaggc ttggtccagc ctggagggtc cctgagactc     60

tcctgtgcag cctctggatt caccttcact gactactaca tgagctgggt ccgccaggct    120

ccagggaagg ggctggagtg gttgggcttt attagaaaca aagctaacgg ttacaccaca    180

gaatacagtg cgtctgtgaa aggcagattc accatctcaa gagataattc aaagaactca    240

ctgtatctgc aaatgaacag cctgcgtgct gaggacacgg ccgtgtatta ctgtgctaga    300

gataactggt ttgcttactg gggtcaagga accctggtca ccgtctcctc ggctagcacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga aagttgagcc caaatcttgt    660

gacaaaactc acacatgccc accgtgccca gcacctgaac tcctgggggg accgtcagtc    720
```

```
ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840

ggcgtggagg tgcataatgc caagacaaag ccgcgggagg agcagtacaa cagcacgtac    900

cgtgtggtca gcgtcctcac cgtcctgcac caggactggc tgaatggcaa ggagtacaag    960

tgcaaggtct ccaacaaagc cctcccagcc cccatcgaga aaaccatctc caaagccaaa   1020

gggcagcccc gagaaccaca ggtgtacacc ctgcccccat cccgggagga gatgaccaag   1080

aaccaggtca gcctgacctg cctggtcaaa ggcttctatc ccagcgacat cgccgtggag   1140

tgggagagca atgggcagcc ggagaacaac tacaagacca cgcctcccgt gctggactcc   1200

gacggctcct tcttcctcta cagcaagctc accgtggaca agagcaggtg gcagcagggg   1260

aacgtcttct catgctccgt gatgcatgag gctctgcaca accactacac gcagaagagc   1320

ctctccctgt ctccgggtaa atgactcgag                                    1350


<210> SEQ ID NO 49
<211> LENGTH: 1350
<212> TYPE: DNA
<213> ORGANISM: Artificial Sequence
<220> FEATURE:
<223> OTHER INFORMATION: Synthetic (nucleotide sequence of H4-heavy)

<400> SEQUENCE: 49

gaggttcagc tggtggagtc tggcggtggc ctggtgcagc caggggggctc actccgtttg     60

tcctgtgcag cttctggctt caccttcact gattactaca tgagctgggt gcgtcaggcc    120

ccgggtaagg gcctggaatg gttgggtttt attagaaaca aagctaatgg ttacacaaca    180

gagtacagtg catctgtgaa gggtcgtttc actataagca gagataattc caaaaacaca    240

ctgtacctgc agatgaacag cctgcgtgct gaggacactg ccgtctatta ttgtgctaga    300

gataactggt ttgcttactg gggccaaggg actctggtca ccgtctcctc ggctagcacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga aagttgagcc caaatcttgt    660

gacaaaactc acacatgccc accgtgccca gcacctgaac tcctgggggg accgtcagtc    720

ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840

ggcgtggagg tgcataatgc caagacaaag ccgcgggagg agcagtacaa cagcacgtac    900

cgtgtggtca gcgtcctcac cgtcctgcac caggactggc tgaatggcaa ggagtacaag    960

tgcaaggtct ccaacaaagc cctcccagcc cccatcgaga aaaccatctc caaagccaaa   1020

gggcagcccc gagaaccaca ggtgtacacc ctgcccccat cccgggagga gatgaccaag   1080

aaccaggtca gcctgacctg cctggtcaaa ggcttctatc ccagcgacat cgccgtggag   1140

tgggagagca atgggcagcc ggagaacaac tacaagacca cgcctcccgt gctggactcc   1200

gacggctcct tcttcctcta cagcaagctc accgtggaca agagcaggtg gcagcagggg   1260

aacgtcttct catgctccgt gatgcatgag gctctgcaca accactacac gcagaagagc   1320

ctctccctgt ctccgggtaa atgactcgag                                    1350
```

-continued

<210> SEQ ID NO 50
<211> LENGTH: 669
<212> TYPE: DNA
<213> ORGANISM: Artificial Sequence
<220> FEATURE:
<223> OTHER INFORMATION: Synthetic (nucleotide sequence of H1-light)

<400> SEQUENCE: 50
gacatcgtga tgacccagtc tccagactcc ctggctgtgt ctctgggcga gagggccacc 60
atcaactgca agtccagcca gagtctttta gctagcggca accaaaataa ctacttagct 120
tggcaccagc agaaaccagg acagcctcct aagatgctca ttatttgggc atctacccgg 180
gtatccgggg tccctgaccg attcagtggc agcgggtctg ggacagattt cactctcacc 240
atcagcagcc tgcaggctga agatgtggca gtttattact gtcagcaatc ctatagtgct 300
cctctcacgt tcggaggcgg taccaaggtg gagatcaaac gtacggtggc tgcaccatct 360
gtcttcatct tcccgccatc tgatgagcag ttgaaatctg gaactgcctc tgttgtgtgc 420
ctgctgaata acttctatcc cagagaggcc aaagtacagt ggaaggtgga taacgccctc 480
caatcgggta actcccagga gagtgtcaca gagcaggaca gcaaggacag cacctacagc 540
ctcagcagca ccctgacgct gagcaaagca gactacgaga aacacaaagt ctacgcctgc 600
gaagtcaccc atcagggcct gagctcgccc gtcacaaaga gcttcaacag gggagagtgt 660
tgactcgag 669

<210> SEQ ID NO 51
<211> LENGTH: 669
<212> TYPE: DNA
<213> ORGANISM: Artificial Sequence
<220> FEATURE:
<223> OTHER INFORMATION: Synthetic (nucleotide sequence of H2-light)

<400> SEQUENCE: 51
gatattgtga tgacccagac tccactctcc ctgcccgtca cccctggaga gccggcctcc 60
atctcctgca agtccagtca gagtctttta gctagtggca accaaaataa ctacttggcc 120
tggcacctgc agaagccagg gcagtctcca cagatgctga tcatttgggc atccactagg 180
gtatctggag tcccagacag gttcagtggc agtgggtcag gcactgattt cacactgaaa 240
atcagcaggg tggaggctga ggatgttgga gtttattact gccagcagtc ctacagcgct 300
ccgctcacgt tcggacaggg taccaagctg gagctcaaac gtacggtggc tgcaccatct 360
gtcttcatct tcccgccatc tgatgagcag ttgaaatctg gaactgcctc tgttgtgtgc 420
ctgctgaata acttctatcc cagagaggcc aaagtacagt ggaaggtgga taacgccctc 480
caatcgggta actcccagga gagtgtcaca gagcaggaca gcaaggacag cacctacagc 540
ctcagcagca ccctgacgct gagcaaagca gactacgaga aacacaaagt ctacgcctgc 600
gaagtcaccc atcagggcct gagctcgccc gtcacaaaga gcttcaacag gggagagtgt 660
tgactcgag 669

<210> SEQ ID NO 52
<211> LENGTH: 669
<212> TYPE: DNA
<213> ORGANISM: Artificial Sequence
<220> FEATURE:
<223> OTHER INFORMATION: Synthetic (nucleotide sequence of H3-light)

<400> SEQUENCE: 52
gacatcgtga tgacccagtc tccagactcc ctggctgtgt ctctgggcga gagggccacc 60

```
atcaactgca agtccagcca gagtctttta gctagcggca accaaaataa ctacttagct    120

tggtaccagc agaaaccagg acagcctcct aagctgctca ttatttgggc atctacccgg    180

gtatccgggg tccctgaccg attcagtggc agcgggtctg ggacagattt cactctcacc    240

atcagcagcc tgcaggctga agatgtggca gtttattact gtcagcaatc ctatagtgct    300

cctctcacgt tcggaggcgg taccaaggtg gagatcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660

tgactcgag                                                            669
```

<210> SEQ ID NO 53
<211> LENGTH: 669
<212> TYPE: DNA
<213> ORGANISM: Artificial Sequence
<220> FEATURE:
<223> OTHER INFORMATION: Synthetic (nucleotide sequence of H4-light)

<400> SEQUENCE: 53

```
gatatccaga tgacccagtc cccgagctcc ctgtccgcct ctgtgggcga tagggtcacc     60

atcacctgca agtccagtca gagtctttta gctagtggca accaaaataa ctacttggcc    120

tggcaccaac agaaaccagg aaaagctccg aaaatgctga ttatttgggc atccactagg    180

gtatctggag tcccttctcg cttctctgga tccgggtctg ggacggattt cactctgacc    240

atcagcagtc tgcagccgga agacttcgca acttattact gtcagcagtc ctacagcgct    300

ccgctcacgt tcggacaggg taccaaggtg gagatcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660

tgactcgag                                                            669
```

<210> SEQ ID NO 54
<211> LENGTH: 23
<212> TYPE: PRT
<213> ORGANISM: Artificial Sequence
<220> FEATURE:
<223> OTHER INFORMATION: Synthetic (linker between VH and VL)

<400> SEQUENCE: 54

```
Gly Leu Gly Gly Leu Gly Gly Gly Gly Ser Gly Gly Gly Gly Ser Gly
1               5                   10                  15

Gly Ser Ser Gly Val Gly Ser
            20
```

<210> SEQ ID NO 55
<211> LENGTH: 1088
<212> TYPE: DNA
<213> ORGANISM: Artificial Sequence
<220> FEATURE:
<223> OTHER INFORMATION: Synthetic (polynucleotide encoding scFv of huAbF46 antibody)

<400> SEQUENCE: 55

```
gctagcgttt tagcagaagt tcaattggtt gaatctggtg gtggtttggt tcaaccaggt      60
ggttctttga gattgtcttg tgctgcttct ggttttactt tcaccgatta ttacatgtcc     120
tgggttagac aagctccagg taaaggtttg gaatggttgg gtttcattag aaacaaggct     180
aacggttaca ctaccgaata ttctgcttct gttaagggta gattcaccat ttctagagac     240
aactctaaga acaccttgta cttgcaaatg aactccttga gagctgaaga tactgctgtt     300
tattactgcg ctagagataa ttggtttgct tattggggtc aaggtacttt ggttactgtt     360
tcttctggcc tcgggggcct cggaggagga ggtagtggcg gaggaggctc cggtggatcc     420
agcggtgtgg gttccgatat tcaaatgacc caatctccat cttctttgtc tgcttcagtt     480
ggtgatagag ttaccattac ttgtaagtcc tcccaatctt tgttggcttc tggtaatcag     540
aacaattact tggcttggca tcaacaaaaa ccaggtaaag ctccaaagat gttgattatt     600
tgggcttcta ccagagtttc tggtgttcca tctagatttt ctggttctgg ttccggtact     660
gattttactt tgaccatttc atccttgcaa ccagaagatt tcgctactta ctactgtcaa     720
caatcttact ctgctccatt gacttttggt caaggtacaa aggtcgaaat caagagagaa     780
ttcggtaagc ctatccctaa ccctctcctc ggtctcgatt ctacgggtgg tggtggatct     840
ggtggtggtg gttctggtgg tggtggttct caggaactga caactatatg cgagcaaatc     900
ccctcaccaa ctttagaatc gacgccgtac tctttgtcaa cgactactat tttggccaac     960
gggaaggcaa tgcaaggagt ttttgaatat tacaaatcag taacgtttgt cagtaattgc    1020
ggttctcacc cctcaacaac tagcaaaggc agccccataa acacacagta tgtttttttga    1080
gtttaaac                                                             1088
```

<210> SEQ ID NO 56
<211> LENGTH: 5597
<212> TYPE: DNA
<213> ORGANISM: Artificial Sequence
<220> FEATURE:
<223> OTHER INFORMATION: Synthetic (expression vector including polynucleotide encoding scFv of huAbF46 antibody)
<220> FEATURE:
<221> NAME/KEY: misc_difference
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:

<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56

```
acggattaga agccgccgag cgggtgacag ccctccgaag gaagactctc ctccgtgcgt     60
cctcgtcttc accggtcgcg ttcctgaaac gcagatgtgc ctcgcgccgc actgctccga    120
acaataaaga ttctacaata ctagctttta tggttatgaa gaggaaaaat tggcagtaac    180
ctggccccac aaaccttcaa atgaacgaat caaattaaca accataggat gataatgcga    240
ttagtttttt agccttattt ctggggtaat taatcagcga agcgatgatt tttgatctat    300
taacagatat ataaatgcaa aaactgcata accactttaa ctaatacttt caacattttc    360
ggtttgtatt acttcttatt caaatgtaat aaaagtatca acaaaaaatt gttaatatac    420
ctctatactt taacgtcaag gagaaaaaac cccggatcgg actactagca gctgtaatac    480
gactcactat agggaatatt aagctaattc tacttcatac attttcaatt aagatgcagt    540
tacttcgctg tttttcaata ttttctgtta ttgctagcgt tttagcagaa gttcaattgg    600
ttgaatctgg tggtggtttg gttcaaccag gtggttcttt gagattgtct tgtgctgctt    660
ctggttttac tttcaccgat tattacatgt cctgggttag acaagctcca ggtaaaggtt    720
tggaatggtt gggtttcatt agaaacaagg ctaacggtta cactaccgaa tattctgctt    780
ctgttaaggg tagattcacc atttctagag acaactctaa gaacaccttg tacttgcaaa    840
tgaactcctt gagagctgaa gatactgctg tttattactg cgctagagat aattggtttg    900
cttattgggg tcaaggtact ttggttactg tttcttctgg cctcgggggc ctcggaggag    960
gaggtagtgg cggaggaggc tccggtggat ccagcggtgt gggttccgat attcaaatga   1020
cccaatctcc atcttctttg tctgcttcag ttggtgatag agttaccatt acttgtaagt   1080
cctcccaatc tttgttggct tctggtaatc agaacaatta cttggcttgg catcaacaaa   1140
aaccaggtaa agctccaaag atgttgatta tttgggcttc taccagagtt tctggtgttc   1200
catctagatt ttctggttct ggttccggta ctgattttac tttgaccatt tcatccttgc   1260
aaccagaaga tttcgctact tactactgtc aacaatctta ctctgctcca ttgacttttg   1320
gtcaaggtac aaaggtcgaa atcaagagag aattcggtaa gcctatccct aaccctctcc   1380
tcggtctcga ttctacgggt ggtggtggat ctggtggtgg tggttctggt ggtggtggtt   1440
ctcaggaact gacaactata tgcgagcaaa tcccctcacc aactttagaa tcgacgccgt   1500
actctttgtc aacgactact attttggcca acgggaaggc aatgcaagga gtttttgaat   1560
attacaaatc agtaacgttt gtcagtaatt gcggttctca cccctcaaca actagcaaag   1620
gcagccccat aaacacacag tatgtttttt gagtttaaac ccgctgatct gataacaaca   1680
gtgtagatgt aacaaaatcg actttgttcc cactgtactt ttagctcgta caaaatacaa   1740
tatacttttc atttctccgt aaacaacatg ttttcccatg taatatcctt ttctattttt   1800
cgttccgtta ccaactttac acatacttta tatagctatt cacttctata cactaaaaaa   1860
ctaagacaat tttaattttg ctgcctgcca tatttcaatt tgttataaat tcctataatt   1920
tatcctatta gtagctaaaa aaagatgaat gtgaatcgaa tcctaagaga attgggcaag   1980
```

-continued

```
tgcacaaaca atacttaaat aaatactact cagtaataac ctatttctta gcatttttga   2040
cgaaatttgc tattttgtta gagtctttta caccatttgt ctccacacct ccgcttacat   2100
caacaccaat aacgccattt aatctaagcg catcaccaac attttctggc gtcagtccac   2160
cagctaacat aaaatgtaag ctctcggggc tctcttgcct tccaacccag tcagaaatcg   2220
agttccaatc caaaagttca cctgtcccac ctgcttctga atcaaacaag ggaataaacg   2280
aatgaggttt ctgtgaagct gcactgagta gtatgttgca gtcttttgga aatacgagtc   2340
ttttaataac tggcaaaccg aggaactctt ggtattcttg ccacgactca tctccgtgca   2400
gttggacgat atcaatgccg taatcattga ccagagccaa aacatcctcc ttaggttgat   2460
tacgaaacac gccaaccaag tatttcggag tgcctgaact atttttatat gcttttacaa   2520
gacttgaaat tttccttgca ataaccgggt caattgttct ctttctattg ggcacacata   2580
taatacccag caagtcagca tcggaatcta gagcacattc tgcggcctct gtgctctgca   2640
agccgcaaac tttcaccaat ggaccagaac tacctgtgaa attaataaca gacatactcc   2700
aagctgcctt tgtgtgctta atcacgtata ctcacgtgct caatagtcac caatgccctc   2760
cctcttggcc ctctcctttt ctttttttcga ccgaatttct tgaagacgaa agggcctcgt   2820
gatacgccta tttttatagg ttaatgtcat gataataatg gtttcttagg acggatcgct   2880
tgcctgtaac ttacacgcgc ctcgtatctt ttaatgatgg aataatttgg gaatttactc   2940
tgtgtttatt tatttttatg ttttgtattt ggattttaga aagtaaataa agaaggtaga   3000
agagttacgg aatgaagaaa aaaaaataaa caaaggttta aaaaatttca acaaaaagcg   3060
tactttacat atatatttat tagacaagaa aagcagatta aatagatata cattcgatta   3120
acgataagta aaatgtaaaa tcacaggatt ttcgtgtgtg gtcttctaca cagacaagat   3180
gaaacaattc ggcattaata cctgagagca ggaagagcaa gataaaaggt agtatttgtt   3240
ggcgatcccc ctagagtctt ttacatcttc ggaaaacaaa aactattttt tctttaattt   3300
ctttttttac tttctatttt taatttatat atttatatta aaaaatttaa attataatta   3360
tttttatagc acgtgatgaa aaggacccag gtggcacttt tcggggaaat gtgcgcggaa   3420
cccctatttg tttatttttc taaatacatt caaatatgta tccgctcatg agacaataac   3480
cctgataaat gcttcaataa tattgaaaaa ggaagagtat gagtattcaa catttccgtg   3540
tcgcccttat tccctttttt gcggcatttt gccttcctgt ttttgctcac ccagaaacgc   3600
tggtgaaagt aaaagatgct gaagatcagt tgggtgcacg agtgggttac atcgaactgg   3660
atctcaacag cggtaagatc cttgagagtt ttcgccccga agaacgtttt ccaatgatga   3720
gcacttttaa agttctgcta tgtggcgcgg tattatcccg tgttgacgcc gggcaagagc   3780
aactcggtcg ccgcatacac tattctcaga atgacttggt tgagtactca ccagtcacag   3840
aaaagcatct tacggatggc atgacagtaa gagaattatg cagtgctgcc ataaccatga   3900
gtgataacac tgcggccaac ttacttctga caacgatcgg aggaccgaag gagctaaccg   3960
cttttttgca caacatgggg gatcatgtaa ctcgccttga tcgttgggaa ccggagctga   4020
atgaagccat accaaacgac gagcgtgaca ccacgatgcc tgtagcaatg gcaacaacgt   4080
tgcgcaaact attaactggc gaactactta ctctagcttc ccggcaacaa ttaatagact   4140
ggatggaggc ggataaagtt gcaggaccac ttctgcgctc ggcccttccg gctggctggt   4200
ttattgctga taaatctgga gccggtgagc gtgggtctcg cggtatcatt gcagcactgg   4260
ggccagatgg taagccctcc cgtatcgtag ttatctacac gacgggcagt caggcaacta   4320
```

tggatgaacg aaatagacag atcgctgaga taggtgcctc actgattaag cattggtaac 4380
tgtcagacca agtttactca tatatacttt agattgattt aaaacttcat ttttaattta 4440
aaaggatcta ggtgaagatc ctttttgata atctcatgac caaaatccct taacgtgagt 4500
tttcgttcca ctgagcgtca gaccccgtag aaaagatcaa aggatcttct tgagatcctt 4560
tttttctgcg cgtaatctgc tgcttgcaaa caaaaaaacc accgctacca gcggtggttt 4620
gtttgccgga tcaagagcta ccaactcttt ttccgaaggt aactggcttc agcagagcgc 4680
agataccaaa tactgtcctt ctagtgtagc cgtagttagg ccaccacttc aagaactctg 4740
tagcaccgcc tacatacctc gctctgctaa tcctgttacc agtggctgct gccagtggcg 4800
ataagtcgtg tcttaccggg ttggactcaa gacgatagtt accggataag gcgcagcggt 4860
cgggctgaac ggggggttcg tgcacacagc ccagcttgga gcgaacgacc tacaccgaac 4920
tgagatacct acagcgtgag cattgagaaa gcgccacgct tcccgaaggg agaaaggcgg 4980
acaggtatcc ggtaagcggc agggtcggaa caggagagcg cacgagggag cttccagggg 5040
ggaacgcctg gtatctttat agtcctgtcg ggtttcgcca cctctgactt gagcgtcgat 5100
ttttgtgatg ctcgtcaggg gggcgagcc tatggaaaaa cgccagcaac gcggcctttt 5160
tacggttcct ggccttttgc tggccttttg ctcacatgtt ctttcctgcg ttatcccctg 5220
attctgtgga taaccgtatt accgcctttg agtgagctga taccgctcgc cgcagccgaa 5280
cgaccgagcg cagcgagtca gtgagcgagg aagcggaaga gcgcccaata cgcaaaccgc 5340
ctctccccgc gcgttggccg attcattaat gcagctggca cgacaggttt cccgactgga 5400
aagcgggcag tgagcgcaac gcaattaatg tgagttacct cactcattag gcaccccagg 5460
ctttacactt tatgcttccg gctcctatgt tgtgtggaat tgtgagcgga taacaatttc 5520
acacaggaaa cagctatgac catgattacg ccaagctcgg aattaaccct cactaaaggg 5580
aacaaaagct ggctagt 5597

<210> SEQ ID NO 57
<211> LENGTH: 13
<212> TYPE: PRT
<213> ORGANISM: Artificial Sequence
<220> FEATURE:
<223> OTHER INFORMATION: Synthetic (U6-HC7 hinge)

<400> SEQUENCE: 57

Glu Pro Lys Ser Cys Asp Cys His Cys Pro Pro Cys Pro
1 5 10

<210> SEQ ID NO 58
<211> LENGTH: 435
<212> TYPE: DNA
<213> ORGANISM: Artificial Sequence
<220> FEATURE:
<223> OTHER INFORMATION: Synthetic (polynucleotide encoding CDR-L3 derived from L3-1 clone)

<400> SEQUENCE: 58
gaattcacta gtgattaatt cgccgccacc atggattcac aggcccaggt cctcatgttg 60
ctgctgctat cggtatctgg tacctgtgga gatatccaga tgacccagtc cccgagctcc 120
ctgtccgcct ctgtgggcga tagggtcacc atcacctgca agtccagtca gagtctttta 180
gctagtggca accaaaataa ctacttggcc tggcaccaac agaaaccagg aaaagctccg 240
aaaatgctga ttatttgggc atccactagg gtatctggag tcccttctcg cttctctgga 300
tccgggtctg ggacggattt cactctgacc atcagcagtc tgcagccgga agacttcgca 360

```
acttattact gtcagcagtc ctacagccgc ccgtacacgt tcggacaggg taccaaggtg    420

gagatcaaac gtacg                                                     435


<210> SEQ ID NO 59
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-2 clone)

<400> SEQUENCE: 59

gaattcacta gtgattaatt cgccgccacc atggattcac aggcccaggt cctcatgttg     60

ctgctgctat cggtatctgg tacctgtgga gatatccaga tgacccagtc cccgagctcc    120

ctgtccgcct ctgtgggcga tagggtcacc atcacctgca agtccagtca gagtctttta    180

gctagtggca accaaaataa ctacttggcc tggcaccaac agaaaccagg aaaagctccg    240

aaaatgctga ttatttgggc atccactagg gtatctggag tcccttctcg cttctctgga    300

tccgggtctg ggacggattt cactctgacc atcagcagtc tgcagccgga agacttcgca    360

acttattact gtgggcagtc ctacagccgt ccgctcacgt tcggacaggg taccaaggtg    420

gagatcaaac gtacg                                                     435


<210> SEQ ID NO 60
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-3 clone)

<400> SEQUENCE: 60

gaattcacta gtgattaatt cgccgccacc atggattcac aggcccaggt cctcatgttg     60

ctgctgctat cggtatctgg tacctgtgga gatatccaga tgacccagtc cccgagctcc    120

ctgtccgcct ctgtgggcga tagggtcacc atcacctgca agtccagtca gagtctttta    180

gctagtggca accaaaataa ctacttggcc tggcaccaac agaaaccagg aaaagctccg    240

aaaatgctga ttatttgggc atccactagg gtatctggag tcccttctcg cttctctgga    300

tccgggtctg ggacggattt cactctgacc atcagcagtc tgcagccgga agacttcgca    360

acttattact gtgcacagtc ctacagccat ccgttctctt tcggacaggg taccaaggtg    420

gagatcaaac gtacg                                                     435


<210> SEQ ID NO 61
<211> LENGTH: 435
<212> TYPE: DNA
<213> ORGANISM: Artificial Sequence
<220> FEATURE:
<223> OTHER INFORMATION: Synthetic (polynucleotide encoding CDR-L3
      derived from L3-5 clone)

<400> SEQUENCE: 61

gaattcacta gtgattaatt cgccgccacc atggattcac aggcccaggt cctcatgttg     60

ctgctgctat cggtatctgg tacctgtgga gatatccaga tgacccagtc cccgagctcc    120

ctgtccgcct ctgtgggcga tagggtcacc atcacctgca agtccagtca gagtctttta    180

gctagtggca accaaaataa ctacttggcc tggcaccaac agaaaccagg aaaagctccg    240

aaaatgctga ttatttgggc atccactagg gtatctggag tcccttctcg cttctctgga    300
```

tccgggtctg ggacggattt cactctgacc atcagcagtc tgcagccgga agacttcgca 360
acttattact gtcagcagtc ctacagccgc ccgtttacgt tcggacaggg taccaaggtg 420
gagatcaaac gtacg 435

<210> SEQ ID NO 62
<211> LENGTH: 462
<212> TYPE: PRT
<213> ORGANISM: Artificial Sequence
<220> FEATURE:
<223> OTHER INFORMATION: Synthetic (polypeptide consisting of heavy chain of huAbF46-H4-A1, U6-HC7 hinge and constant region of human IgG1)

<400> SEQUENCE: 62

```
Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Cys His
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320
```

-continued

```
Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460


<210> SEQ ID NO 63
<211> LENGTH: 1410
<212> TYPE: DNA
<213> ORGANISM: Artificial Sequence
<220> FEATURE:
<223> OTHER INFORMATION: Synthetic (polynucleotide encoding polypeptide
      consisting of heavy chain of huAbF46-H4-A1, U6-HC7 hinge and
      constant region of human IgG1)

<400> SEQUENCE: 63

gaattcgccg ccaccatgga atggagctgg gtttttctcg taacactttt aaatggtatc     60

cagtgtgagg ttcagctggt ggagtctggc ggtggcctgg tgcagccagg gggctcactc    120

cgtttgtcct gtgcagcttc tggcttcacc ttcactgatt actacatgag ctgggtgcgt    180

caggccccgg gtaagggcct ggaatggttg ggttttatta gaaacaaagc taatggttac    240

acaacagagt acagtgcatc tgtgaagggt cgtttcacta taagcagaga taattccaaa    300

aacacactgt acctgcagat gaacagcctg cgtgctgagg acactgccgt ctattattgt    360

gctagagata actggtttgc ttactggggc caagggactc tggtcaccgt ctcctcggct    420

agcaccaagg gcccatcggt cttccccctg gcaccctcct ccaagagcac ctctgggggc    480

acagcggccc tgggctgcct ggtcaaggac tacttccccg aaccggtgac ggtgtcgtgg    540

aactcaggcg ccctgaccag cggcgtgcac accttcccgg ctgtcctaca gtcctcagga    600

ctctactccc tcagcagcgt ggtgaccgtg ccctccagca gcttgggcac ccagacctac    660

atctgcaacg tgaatcacaa gcccagcaac accaaggtgg acaagaaagt tgagcccaaa    720

agctgcgatt gccactgtcc tccatgtcca gcacctgaac tcctgggggg accgtcagtc    780

ttcctcttcc ccccaaaacc caaggacacc ctcatgatct cccggacccc tgaggtcaca    840

tgcgtggtgg tggacgtgag ccacgaagac cctgaggtca agttcaactg gtacgtggac    900

ggcgtggagg tgcataatgc caagacaaag ccgcgggagg agcagtacaa cagcacgtac    960

cgtgtggtca gcgtcctcac cgtcctgcac caggactggc tgaatggcaa ggagtacaag   1020

tgcaaggtct ccaacaaagc cctcccagcc cccatcgaga aaaccatctc caaagccaaa   1080

gggcagcccc gagaaccaca ggtgtacacc ctgcccccat cccgggagga gatgaccaag   1140

aaccaggtca gcctgacctg cctggtcaaa ggcttctatc ccagcgacat cgccgtggag   1200
```

```
tgggagagca atgggcagcc ggagaacaac tacaagacca cgcctcccgt gctggactcc   1260

gacggctcct tcttcctcta cagcaagctc accgtggaca agagcaggtg gcagcagggg   1320

aacgtcttct catgctccgt gatgcatgag gctctgcaca accactacac gcagaagagc   1380

ctctccctgt ctccgggtaa atgactcgag                                    1410


<210> SEQ ID NO 64
<211> LENGTH: 461
<212> TYPE: PRT
<213> ORGANISM: Artificial Sequence
<220> FEATURE:
<223> OTHER INFORMATION: Synthetic (polypeptide consisting of heavy
      chain of huAbF46-H4-A1, human IgG2 hinge and constant region of
      human IgG1)

<400> SEQUENCE: 64

Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Thr Phe Thr Asp
        35                  40                  45

Tyr Tyr Met Ser Trp Val Arg Gln Ala Pro Gly Lys Gly Leu Glu Trp
    50                  55                  60

Leu Gly Phe Ile Arg Asn Lys Ala Asn Gly Tyr Thr Thr Glu Tyr Ser
65                  70                  75                  80

Ala Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Arg Lys Cys Cys Val Glu Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320
```

```
Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460


<210> SEQ ID NO 65
<211> LENGTH: 1407
<212> TYPE: DNA
<213> ORGANISM: Artificial Sequence
<220> FEATURE:
<223> OTHER INFORMATION: Synthetic (polynucleotide encoding polypeptide
      consisting of heavy chain of huAbF46-H4-A1, human IgG2 hinge and
      constant region of human IgG1)

<400> SEQUENCE: 65

gaattcgccg ccaccatgga atggagctgg gtttttctcg taacactttt aaatggtatc     60

cagtgtgagg ttcagctggt ggagtctggc ggtggcctgg tgcagccagg ggctcactc    120

cgtttgtcct gtgcagcttc tggcttcacc ttcactgatt actacatgag ctgggtgcgt    180

caggccccgg gtaagggcct ggaatggttg ggttttatta gaaacaaagc taatggttac    240

acaacagagt acagtgcatc tgtgaagggt cgtttcacta taagcagaga taattccaaa    300

aacacactgt acctgcagat gaacagcctg cgtgctgagg acactgccgt ctattattgt    360

gctagagata actggtttgc ttactggggc caagggactc tggtcaccgt ctcctcggct    420

agcaccaagg gcccatcggt cttccccctg gcaccctcct ccaagagcac ctctgggggc    480

acagcggccc tgggctgcct ggtcaaggac tacttccccg aaccggtgac ggtgtcgtgg    540

aactcaggcg ccctgaccag cggcgtgcac accttcccgg ctgtcctaca gtcctcagga    600

ctctactccc tcagcagcgt ggtgaccgtg ccctccagca gcttgggcac ccagacctac    660

atctgcaacg tgaatcacaa gcccagcaac accaaggtgg acaagaaagt tgagaggaag    720

tgctgtgtgg agtgcccccc ctgcccagca cctgaactcc tggggggacc gtcagtcttc    780

ctcttccccc caaaacccaa ggacaccctc atgatctccc ggacccctga ggtcacatgc    840

gtggtggtgg acgtgagcca cgaagaccct gaggtcaagt tcaactggta cgtggacggc    900

gtggaggtgc ataatgccaa gacaaagccg cgggaggagc agtacaacag cacgtaccgt    960

gtggtcagcg tcctcaccgt cctgcaccag gactggctga atggcaagga gtacaagtgc   1020

aaggtctcca acaaagccct cccagccccc atcgagaaaa ccatctccaa agccaaaggg   1080

cagccccgag aaccacaggt gtacaccctg cccccatccc gggaggagat gaccaagaac   1140

caggtcagcc tgacctgcct ggtcaaaggc ttctatccca gcgacatcgc cgtggagtgg   1200
```

-continued gagagcaatg ggcagccgga gaacaactac aagaccacgc ctcccgtgct ggactccgac 1260
ggctccttct tcctctacag caagctcacc gtggacaaga gcaggtggca gcaggggaac 1320
gtcttctcat gctccgtgat gcatgaggct ctgcacaacc actacacgca gaagagcctc 1380
tccctgtctc cgggtaaatg actcgag 1407

<210> SEQ ID NO 66
<211> LENGTH: 460
<212> TYPE: PRT
<213> ORGANISM: Artificial Sequence
<220> FEATURE:
<223> OTHER INFORMATION: Synthetic (polypeptide consisting of heavy chain of huAbF46-H4-A1, human IgG2 hinge and constant region of human IgG2)

<400> SEQUENCE: 66

Met Glu Trp Ser Trp Val Phe Leu Val Thr Leu Leu Asn Gly Ile Gln
1 5 10 15

Cys Glu Val Gln Leu Val Glu Ser Gly Gly Gly Leu Val Gln Pro Gly
20 25 30

Gly Ser Leu Arg Leu Ser Cys Ala Ala Ser Gly Phe Thr Phe Thr Asp
35 40 45

Tyr Tyr Met Ser Trp Val Arg Gln Ala Pro Gly Lys Gly Leu Glu Trp
50 55 60

Leu Gly Phe Ile Arg Asn Lys Ala Asn Gly Tyr Thr Thr Glu Tyr Ser
65 70 75 80

Ala Ser Val Lys Gly Arg Phe Thr Ile Ser Arg Asp Asn Ser Lys Asn
85 90 95

Thr Leu Tyr Leu Gln Met Asn Ser Leu Arg Ala Glu Asp Thr Ala Val
100 105 110

Tyr Tyr Cys Ala Arg Asp Asn Trp Phe Ala Tyr Trp Gly Gln Gly Thr
115 120 125

Leu Val Thr Val Ser Ser Ala Ser Thr Lys Gly Pro Ser Val Phe Pro
130 135 140

Leu Ala Pro Cys Ser Arg Ser Thr Ser Glu Ser Thr Ala Ala Leu Gly
145 150 155 160

Cys Leu Val Lys Asp Tyr Phe Pro Glu Pro Val Thr Val Ser Trp Asn
165 170 175

Ser Gly Ala Leu Thr Ser Gly Val His Thr Phe Pro Ala Val Leu Gln
180 185 190

Ser Ser Gly Leu Tyr Ser Leu Ser Ser Val Val Thr Val Pro Ser Ser
195 200 205

Asn Phe Gly Thr Gln Thr Tyr Thr Cys Asn Val Asp His Lys Pro Ser
210 215 220

Asn Thr Lys Val Asp Lys Thr Val Glu Arg Lys Cys Cys Val Glu Cys
225 230 235 240

Pro Pro Cys Pro Ala Pro Pro Val Ala Gly Pro Ser Val Phe Leu Phe
245 250 255

Pro Pro Lys Pro Lys Asp Thr Leu Met Ile Ser Arg Thr Pro Glu Val
260 265 270

Thr Cys Val Val Val Asp Val Ser His Glu Asp Pro Glu Val Gln Phe
275 280 285

Asn Trp Tyr Val Asp Gly Val Glu Val His Asn Ala Lys Thr Lys Pro
290 295 300

Arg Glu Glu Gln Phe Asn Ser Thr Phe Arg Val Val Ser Val Leu Thr

-continued

```
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460


<210> SEQ ID NO 67
<211> LENGTH: 1404
<212> TYPE: DNA
<213> ORGANISM: Artificial Sequence
<220> FEATURE:
<223> OTHER INFORMATION: Synthetic (polynucleotide encoding polypeptide
      consisting of heavy chain of huAbF46-H4-A1, human IgG2 hinge and
      constant region of human IgG2)

<400> SEQUENCE: 67

gaattcgccg ccaccatgga atggagctgg gtttttctcg taacactttt aaatggtatc     60

cagtgtgagg ttcagctggt ggagtctggc ggtggcctgg tgcagccagg gggctcactc    120

cgtttgtcct gtgcagcttc tggcttcacc ttcactgatt actacatgag ctgggtgcgt    180

caggccccgg gtaagggcct ggaatggttg ggttttatta gaaacaaagc taatggttac    240

acaacagagt acagtgcatc tgtgaagggt cgtttcacta taagcagaga taattccaaa    300

aacacactgt acctgcagat gaacagcctg cgtgctgagg acactgccgt ctattattgt    360

gctagagata actggtttgc ttactggggc caagggactc tggtcaccgt ctcctcggct    420

agcaccaagg gcccatcggt cttccccctg gcgccctgct ccaggagcac ctccgagagc    480

acagcggccc tgggctgcct ggtcaaggac tacttccccg aaccggtgac ggtgtcgtgg    540

aactcaggcg ctctgaccag cggcgtgcac accttcccag ctgtcctaca gtcctcagga    600

ctctactccc tcagcagcgt ggtgaccgtg ccctccagca acttcggcac ccagacctac    660

acctgcaacg tagatcacaa gcccagcaac accaaggtgg acaagacagt tgagcgcaaa    720

tgttgtgtcg agtgcccacc gtgcccagca ccacctgtgg caggaccgtc agtcttcctc    780

ttccccccaa aacccaagga caccctcatg atctcccgga cccctgaggt cacgtgcgtg    840

gtggtggacg tgagccacga agaccccgag gtccagttca actggtacgt ggacggcgtg    900

gaggtgcata atgccaagac aaagccacgg gaggagcagt tcaacagcac gttccgtgtg    960

gtcagcgtcc tcaccgttgt gcaccaggac tggctgaacg gcaaggagta caagtgcaag   1020

gtctccaaca aaggcctccc agcccccatc gagaaaacca tctccaaaac caaagggcag   1080

ccccgagaac cacaggtgta caccctgccc ccatcccggg aggagatgac caagaaccag   1140
```

-continued

```
gtcagcctga cctgcctggt caaaggcttc taccccagcg acatcgccgt ggagtgggag   1200

agcaatgggc agccggagaa caactacaag accacgcctc ccatgctgga ctccgacggc   1260

tccttcttcc tctacagcaa gctcaccgtg gacaagagca ggtggcagca ggggaacgtc   1320

ttctcatgct ccgtgatgca tgaggctctg cacaaccact acacgcagaa gagcctctcc   1380

ctgtctccgg gtaaatgact cgag                                          1404


<210> SEQ ID NO 68
<211> LENGTH: 240
<212> TYPE: PRT
<213> ORGANISM: Artificial Sequence
<220> FEATURE:
<223> OTHER INFORMATION: Synthetic (polypeptide consisting of light
      chain of huAbF46-H4-A1(H36Y) and human kappa constant region)

<400> SEQUENCE: 68

Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp Tyr Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240


<210> SEQ ID NO 69
<211> LENGTH: 758
<212> TYPE: DNA
<213> ORGANISM: Artificial Sequence
<220> FEATURE:
<223> OTHER INFORMATION: Synthetic (polynucleotide encoding polypeptide
      consisting of light chain of huAbF46-H4-A1(H36Y) and human kappa
      constant region)

<400> SEQUENCE: 69

aattcactag tgattaattc gccgccacca tggattcaca ggcccaggtc ctcatgttgc     60
```

```
tgctgctatc ggtatctggt acctgtggag atatccagat gacccagtcc ccgagctccc    120

tgtccgcctc tgtgggcgat agggtcacca tcacctgcaa gtccagtcag agtcttttag    180

ctagtggcaa ccaaaataac tacttggcct ggtaccaaca gaaaccagga aaagctccga    240

aaatgctgat tatttgggca tccactaggg tatctggagt cccttctcgc ttctctggat    300

ccgggtctgg gacggatttc actctgacca tcagcagtct gcagccggaa gacttcgcaa    360

cttattactg tcagcagtcc tacagccgcc cgtacacgtt cggacagggt accaaggtgg    420

agatcaaacg tacggtggct gcaccatctg tcttcatctt cccgccatct gatgagcagt    480

tgaaatctgg aactgcctct gttgtgtgcc tgctgaataa cttctatccc agagaggcca    540

aagtacagtg gaaggtggat aacgccctcc aatcgggtaa ctcccaggag agtgtcacag    600

agcaggacag caaggacagc acctacagcc tcagcagcac cctgacgctg agcaaagcag    660

actacgagaa acacaaagtc tacgcctgcg aagtcaccca tcagggcctg agctcgcccg    720

tcacaaagag cttcaacagg ggagagtgtt gactcgag                            758


<210> SEQ ID NO 70
<211> LENGTH: 240
<212> TYPE: PRT
<213> ORGANISM: Artificial Sequence
<220> FEATURE:
<223> OTHER INFORMATION: Synthetic (polypeptide consisting of light
      chain of huAbF46-H4-A1 and human kappa constant region)

<400> SEQUENCE: 70

Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Leu Ala Ser Gly Asn Gln Asn Asn Tyr Leu Ala Trp His Gln Gln
    50                  55                  60

Lys Pro Gly Lys Ala Pro Lys Met Leu Ile Ile Trp Ala Ser Thr Arg
65                  70                  75                  80

Val Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
```

-continued

```
225                 230                 235                 240


<210> SEQ ID NO 71
<211> LENGTH: 19
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 71

Phe Ser Pro Gln Ile Glu Glu Pro Ser Gln Cys Pro Asp Cys Val Val
1               5                   10                  15

Ser Ala Leu


<210> SEQ ID NO 72
<211> LENGTH: 10
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 72

Pro Gln Ile Glu Glu Pro Ser Gln Cys Pro
1               5                   10


<210> SEQ ID NO 73
<211> LENGTH: 5
<212> TYPE: PRT
<213> ORGANISM: Artificial Sequence
<220> FEATURE:
<223> OTHER INFORMATION: Synthetic (epitope in SEMA domain of c-Met)

<400> SEQUENCE: 73

Glu Glu Pro Ser Gln
1               5


<210> SEQ ID NO 74
<211> LENGTH: 117
<212> TYPE: PRT
<213> ORGANISM: Artificial Sequence
<220> FEATURE:
<223> OTHER INFORMATION: Synthetic (heavy chain variable region of
      anti-c-Met antibody (AbF46 or huAbF46-H1))

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115
```

-continued

<210> SEQ ID NO 75
<211> LENGTH: 114
<212> TYPE: PRT
<213> ORGANISM: Artificial Sequence
<220> FEATURE:
<223> OTHER INFORMATION: Synthetic (light chain variable region of anti-c-Met antibody (AbF46 or huAbF46-H1))

<400> SEQUENCE: 75

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg
```

<210> SEQ ID NO 76
<211> LENGTH: 1416
<212> TYPE: DNA
<213> ORGANISM: Artificial Sequence
<220> FEATURE:
<223> OTHER INFORMATION: Synthetic (nucleotide sequence of heavy chain of anti-c-Met antibody (AbF46 or huAbF46-H1))
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 76

```
gaattcgccg ccaccatgga atggagctgg gtttttctcg taacactttt aaatggtatc      60

cagtgtgagg tgaagctggt ggagtctgga ggaggcttgg tacagcctgg gggttctctg     120

agactctcct gtgcaacttc tgggttcacc ttcactgatt actacatgag ctgggtccgc     180

cagcctccag gaaaggcact tgagtggttg ggttttatta gaaacaaagc taatggttac     240
```

```
acaacagagt acagtgcatc tgtgaagggt cggttcacca tctccagaga taattcccaa    300

agcatcctct atcttcaaat ggacaccctg agagctgagg acagtgccac ttattactgt    360

gcaagagata actggtttgc ttactggggc caagggactc tggtcactgt ctctgcagct    420

agcaccaagg gcccatcggt cttcccctg gcaccctcct ccaagagcac ctctgggggc    480

acagcggccc tgggctgcct ggtcaaggac tacttccccg aaccggtgac ggtgtcgtgg    540

aactcaggcg ccctgaccag cggcgtgcac accttcccgg ctgtcctaca gtcctcagga    600

ctctactccc tcagcagcgt ggtgaccgtg ccctccagca gcttgggcac ccagacctac    660

atctgcaacg tgaatcacaa gcccagcaac accaaggtgg acaagaaagt tgagcccaaa    720

tcttgtgaca aaactcacac atgcccaccg tgcccagcac ctgaactcct ggggggaccg    780

tcagtcttcc tcttcccccc aaaacccaag gacaccctca tgatctcccg gacccctgag    840

gtcacatgcg tggtggtgga cgtgagccac gaagaccctg aggtcaagtt caactggtac    900

gtggacggcg tggaggtgca taatgccaag acaaagccgc gggaggagca gtacaacagc    960

acgtaccgtg tggtcagcgt cctcaccgtc ctgcaccagg actggctgaa tggcaaggag   1020

tacaagtgca aggtctccaa caaagccctc ccagccccca tcgagaaaac catctccaaa   1080

gccaaagggc agccccgaga accacaggtg tacaccctgc ccccatcccg ggaggagatg   1140

accaagaacc aggtcagcct gacctgcctg gtcaaaggct tctatcccag cgacatcgcc   1200

gtggagtggg agagcaatgg gcagccggag aacaactaca agaccacgcc tcccgtgctg   1260

gactccgacg gctccttctt cctctacagc aagctcaccg tggacaagag caggtggcag   1320

caggggaacg tcttctcatg ctccgtgatg catgaggctc tgcacaacca ctacacgcag   1380

aagagcctct ccctgtctcc gggtaaatga ctcgag                              1416
```

<210> SEQ ID NO 77
<211> LENGTH: 759
<212> TYPE: DNA
<213> ORGANISM: Artificial Sequence
<220> FEATURE:
<223> OTHER INFORMATION: Synthetic (nucleotide sequence of light chain of anti-c-Met antibody (AbF46 or huAbF46-H1)
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 77

-continued

```
gaattcacta gtgattaatt cgccgccacc atggattcac aggcccaggt cctcatgttg     60

ctgctgctat cggtatctgg tacctgtgga gacattttga tgacccagtc tccatcctcc    120

ctgactgtgt cagcaggaga gaaggtcact atgagctgca agtccagtca gagtctttta    180

gctagtggca accaaaataa ctacttggcc tggcaccagc agaaaccagg acgatctcct    240

aaaatgctga taatttgggc atccactagg gtatctggag tccctgatcg cttcataggc    300

agtggatctg ggacggattt cactctgacc atcaacagtg tgcaggctga agatctggct    360

gtttattact gtcagcagtc ctacagcgct ccgctcacgt tcggtgctgg gaccaagctg    420

gagctgaaac gtacggtggc tgcaccatct gtcttcatct tcccgccatc tgatgagcag    480

ttgaaatctg gaactgcctc tgttgtgtgc ctgctgaata acttctatcc cagagaggcc    540

aaagtacagt ggaaggtgga taacgccctc caatcgggta actcccagga gagtgtcaca    600

gagcaggaca gcaaggacag cacctacagc ctcagcagca ccctgacgct gagcaaagca    660

gactacgaga aacacaaagt ctacgcctgc gaagtcaccc atcagggcct gagctcgccc    720

gtcacaaaga gcttcaacag gggagagtgt tgactcgag                           759
```

```
<210> SEQ ID NO 78
<211> LENGTH: 4170
<212> TYPE: DNA
<213> ORGANISM: Artificial Sequence
<220> FEATURE:
<223> OTHER INFORMATION: Synthetic (polynucleotide encoding c-Met
      protein)

<400> SEQUENCE: 78
```

```
atgaaggccc ccgctgtgct tgcacctggc atcctcgtgc tcctgtttac cttggtgcag     60

aggagcaatg gggagtgtaa agaggcacta gcaaagtccg agatgaatgt gaatatgaag    120

tatcagcttc ccaacttcac cgcggaaaca cccatccaga atgtcattct acatgagcat    180

cacattttcc ttggtgccac taactacatt tatgttttaa atgaggaaga ccttcagaag    240

gttgctgagt acaagactgg gcctgtgctg gaacacccag attgtttccc atgtcaggac    300

tgcagcagca aagccaattt atcaggaggt gtttggaaag ataacatcaa catggctcta    360

gttgtcgaca cctactatga tgatcaactc attagctgtg gcagcgtcaa cagagggacc    420

tgccagcgac atgtctttcc ccacaatcat actgctgaca tacagtcgga ggttcactgc    480

atattctccc cacagataga agagcccagc cagtgtcctg actgtgtggt gagcgccctg    540

ggagccaaag tcctttcatc tgtaaaggac cggttcatca acttctttgt aggcaatacc    600

ataaattctt cttatttccc agatcatcca ttgcattcga tatcagtgag aaggctaaag    660

gaaacgaaag atggttttat gtttttgacg gaccagtcct acattgatgt tttacctgag    720

ttcagagatt cttaccccat taagtatgtc catgcctttg aaagcaacaa ttttatttac    780

ttcttgacgg tccaaaggga aactctagat gctcagactt ttcacacaag aataatcagg    840

ttctgttcca taaactctgg attgcattcc tacatggaaa tgcctctgga gtgtattctc    900

acagaaaaga gaaaaaagag atccacaaag aaggaagtgt ttaatatact tcaggctgcg    960

tatgtcagca agcctggggc ccagcttgct agacaaatag gagccagcct gaatgatgac   1020

attcttttcg gggtgttcgc acaaagcaag ccagattctg ccgaaccaat ggatcgatct   1080

gccatgtgtg cattccctat caaatatgtc aacgacttct tcaacaagat cgtcaacaaa   1140

aacaatgtga gatgtctcca gcatttttac ggacccaatc atgagcactg ctttaatagg   1200

acacttctga gaaattcatc aggctgtgaa gcgcgccgtg atgaatatcg aacagagttt   1260
```

accacagctt tgcagcgcgt tgacttattc atgggtcaat tcagcgaagt cctcttaaca 1320
tctatatcca ccttcattaa aggagacctc accatagcta atcttgggac atcagagggt 1380
cgcttcatgc aggttgtggt ttctcgatca ggaccatcaa cccctcatgt gaattttctc 1440
ctggactccc atccagtgtc tccagaagtg attgtggagc atacattaaa ccaaaatggc 1500
tacacactgg ttatcactgg gaagaagatc acgaagatcc cattgaatgg cttgggctgc 1560
agacatttcc agtcctgcag tcaatgcctc tctgccccac cctttgttca gtgtggctgg 1620
tgccacgaca aatgtgtgcg atcggaggaa tgcctgagcg ggacatggac tcaacagatc 1680
tgtctgcctg caatctacaa ggttttccca aatagtgcac cccttgaagg agggacaagg 1740
ctgaccatat gtggctggga ctttggattt cggaggaata ataaatttga tttaaagaaa 1800
actagagttc tccttggaaa tgagagctgc accttgactt taagtgagag cacgatgaat 1860
acattgaaat gcacagttgg tcctgccatg aataagcatt tcaatatgtc cataattatt 1920
tcaaatggcc acgggacaac acaatacagt acattctcct atgtggatcc tgtaataaca 1980
agtatttcgc cgaaatacgg tcctatggct ggtggcactt tacttacttt aactggaaat 2040
tacctaaaca gtgggaattc tagacacatt tcaattggtg gaaaaacatg tactttaaaa 2100
agtgtgtcaa acagtattct tgaatgttat accccagccc aaaccatttc aactgagttt 2160
gctgttaaat tgaaaattga cttagccaac cgagagacaa gcatcttcag ttaccgtgaa 2220
gatcccattg tctatgaaat tcatccaacc aaatctttta ttagtggtgg gagcacaata 2280
acaggtgttg ggaaaaacct gaattcagtt agtgtcccga gaatggtcat aaatgtgcat 2340
gaagcaggaa ggaactttac agtggcatgt caacatcgct ctaattcaga gataatctgt 2400
tgtaccactc cttccctgca acagctgaat ctgcaactcc ccctgaaaac caaagccttt 2460
ttcatgttag atgggatcct ttccaaatac tttgatctca tttatgtaca taatcctgtg 2520
tttaagcctt ttgaaaagcc agtgatgatc tcaatgggca atgaaaatgt actggaaatt 2580
aagggaaatg atattgaccc tgaagcagtt aaaggtgaag tgttaaaagt tggaaataag 2640
agctgtgaga atatacactt acattctgaa gccgttttat gcacggtccc caatgacctg 2700
ctgaaattga acagcgagct aaatatagag tggaagcaag caatttcttc aaccgtcctt 2760
ggaaaagtaa tagttcaacc agatcagaat ttcacaggat tgattgctgg tgttgtctca 2820
atatcaacag cactgttatt actacttggg tttttcctgt ggctgaaaaa gagaaagcaa 2880
attaaagatc tgggcagtga attagttcgc tacgatgcaa gagtacacac tcctcatttg 2940
gataggcttg taagtgcccg aagtgtaagc ccaactacag aaatggtttc aaatgaatct 3000
gtagactacc gagctacttt tccagaagat cagtttccta attcatctca gaacggttca 3060
tgccgacaag tgcagtatcc tctgacagac atgtccccca tcctaactag tggggactct 3120
gatatatcca gtccattact gcaaaatact gtccacattg acctcagtgc tctaaatcca 3180
gagctggtcc aggcagtgca gcatgtagtg attgggccca gtagcctgat tgtgcatttc 3240
aatgaagtca taggaagagg gcattttggt tgtgtatatc atgggacttt gttggacaat 3300
gatggcaaga aaattcactg tgctgtgaaa tccttgaaca gaatcactga cataggagaa 3360
gtttcccaat ttctgaccga gggaatcatc atgaaagatt ttagtcatcc caatgtcctc 3420
tcgctcctgg gaatctgcct gcgaagtgaa gggtctccgc tggtggtcct accatacatg 3480
aaacatggag atcttcgaaa tttcattcga aatgagactc ataatccaac tgtaaaagat 3540
cttattggct ttggtcttca agtagccaaa ggcatgaaat atcttgcaag caaaaagttt 3600

```
gtccacagag acttggctgc aagaaactgt atgctggatg aaaaattcac agtcaaggtt   3660

gctgattttg gtcttgccag agacatgtat gataaagaat actatagtgt acacaacaaa   3720

acaggtgcaa agctgccagt gaagtggatg gctttggaaa gtctgcaaac tcaaaagttt   3780

accaccaagt cagatgtgtg gtcctttggc gtgctcctct gggagctgat gacaagagga   3840

gccccacctt atcctgacgt aaacaccttt gatataactg tttacttgtt gcaagggaga   3900

agactcctac aacccgaata ctgcccagac cccttatatg aagtaatgct aaaatgctgg   3960

caccctaaag ccgaaatgcg cccatccttt tctgaactgg tgtcccggat atcagcgatc   4020

ttctctactt tcattgggga gcactatgtc catgtgaacg ctacttatgt gaacgtaaaa   4080

tgtgtcgctc cgtatccttc tctgttgtca tcagaagata acgctgatga tgaggtggac   4140

acacgaccag cctccttctg ggagacatca                                    4170
```

<210> SEQ ID NO 79
<211> LENGTH: 444
<212> TYPE: PRT
<213> ORGANISM: Artificial Sequence
<220> FEATURE:
<223> OTHER INFORMATION: Synthetic (SEMA domain of c-Met)

<400> SEQUENCE: 79

```
Leu His Glu His His Ile Phe Leu Gly Ala Thr Asn Tyr Ile Tyr Val
1               5                   10                  15

Leu Asn Glu Glu Asp Leu Gln Lys Val Ala Glu Tyr Lys Thr Gly Pro
            20                  25                  30

Val Leu Glu His Pro Asp Cys Phe Pro Cys Gln Asp Cys Ser Ser Lys
        35                  40                  45

Ala Asn Leu Ser Gly Gly Val Trp Lys Asp Asn Ile Asn Met Ala Leu
    50                  55                  60

Val Val Asp Thr Tyr Tyr Asp Asp Gln Leu Ile Ser Cys Gly Ser Val
65                  70                  75                  80

Asn Arg Gly Thr Cys Gln Arg His Val Phe Pro His Asn His Thr Ala
                85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125

Leu Ser Ser Val Lys Asp Arg Phe Ile Asn Phe Phe Val Gly Asn Thr
    130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
            180                 185                 190

Tyr Val His Ala Phe Glu Ser Asn Asn Phe Ile Tyr Phe Leu Thr Val
        195                 200                 205

Gln Arg Glu Thr Leu Asp Ala Gln Thr Phe His Thr Arg Ile Ile Arg
    210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Lys Arg Ser Thr Lys Lys Glu
                245                 250                 255

Val Phe Asn Ile Leu Gln Ala Ala Tyr Val Ser Lys Pro Gly Ala Gln
```

260 265 270

Leu Ala Arg Gln Ile Gly Ala Ser Leu Asn Asp Asp Ile Leu Phe Gly
275 280 285

Val Phe Ala Gln Ser Lys Pro Asp Ser Ala Glu Pro Met Asp Arg Ser
290 295 300

Ala Met Cys Ala Phe Pro Ile Lys Tyr Val Asn Asp Phe Phe Asn Lys
305 310 315 320

Ile Val Asn Lys Asn Asn Val Arg Cys Leu Gln His Phe Tyr Gly Pro
325 330 335

Asn His Glu His Cys Phe Asn Arg Thr Leu Leu Arg Asn Ser Ser Gly
340 345 350

Cys Glu Ala Arg Arg Asp Glu Tyr Arg Thr Glu Phe Thr Thr Ala Leu
355 360 365

Gln Arg Val Asp Leu Phe Met Gly Gln Phe Ser Glu Val Leu Leu Thr
370 375 380

Ser Ile Ser Thr Phe Ile Lys Gly Asp Leu Thr Ile Ala Asn Leu Gly
385 390 395 400

Thr Ser Glu Gly Arg Phe Met Gln Val Val Val Ser Arg Ser Gly Pro
405 410 415

Ser Thr Pro His Val Asn Phe Leu Leu Asp Ser His Pro Val Ser Pro
420 425 430

Glu Val Ile Val Glu His Thr Leu Asn Gln Asn Gly
435 440

<210> SEQ ID NO 80
<211> LENGTH: 451
<212> TYPE: PRT
<213> ORGANISM: Artificial Sequence
<220> FEATURE:
<223> OTHER INFORMATION: Synthetic (PSI-IPT domain of c-Met)

<400> SEQUENCE: 80

Tyr Thr Leu Val Ile Thr Gly Lys Lys Ile Thr Lys Ile Pro Leu Asn
1 5 10 15

Gly Leu Gly Cys Arg His Phe Gln Ser Cys Ser Gln Cys Leu Ser Ala
20 25 30

Pro Pro Phe Val Gln Cys Gly Trp Cys His Asp Lys Cys Val Arg Ser
35 40 45

Glu Glu Cys Leu Ser Gly Thr Trp Thr Gln Gln Ile Cys Leu Pro Ala
50 55 60

Ile Tyr Lys Val Phe Pro Asn Ser Ala Pro Leu Glu Gly Gly Thr Arg
65 70 75 80

Leu Thr Ile Cys Gly Trp Asp Phe Gly Phe Arg Arg Asn Asn Lys Phe
85 90 95

Asp Leu Lys Lys Thr Arg Val Leu Leu Gly Asn Glu Ser Cys Thr Leu
100 105 110

Thr Leu Ser Glu Ser Thr Met Asn Thr Leu Lys Cys Thr Val Gly Pro
115 120 125

Ala Met Asn Lys His Phe Asn Met Ser Ile Ile Ile Ser Asn Gly His
130 135 140

Gly Thr Thr Gln Tyr Ser Thr Phe Ser Tyr Val Asp Pro Val Ile Thr
145 150 155 160

Ser Ile Ser Pro Lys Tyr Gly Pro Met Ala Gly Gly Thr Leu Leu Thr
165 170 175

Leu Thr Gly Asn Tyr Leu Asn Ser Gly Asn Ser Arg His Ile Ser Ile

```
            180                 185                 190

Gly Gly Lys Thr Cys Thr Leu Lys Ser Val Ser Asn Ser Ile Leu Glu
        195                 200                 205

Cys Tyr Thr Pro Ala Gln Thr Ile Ser Thr Glu Phe Ala Val Lys Leu
    210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                245                 250                 255

Trp Trp Lys Glu Pro Leu Asn Ile Val Ser Phe Leu Phe Cys Phe Ala
            260                 265                 270

Ser Gly Gly Ser Thr Ile Thr Gly Val Gly Lys Asn Leu Asn Ser Val
        275                 280                 285

Ser Val Pro Arg Met Val Ile Asn Val His Glu Ala Gly Arg Asn Phe
    290                 295                 300

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
                325                 330                 335

Ala Phe Phe Met Leu Asp Gly Ile Leu Ser Lys Tyr Phe Asp Leu Ile
            340                 345                 350

Tyr Val His Asn Pro Val Phe Lys Pro Phe Glu Lys Pro Val Met Ile
        355                 360                 365

Ser Met Gly Asn Glu Asn Val Leu Glu Ile Lys Gly Asn Asp Ile Asp
    370                 375                 380

Pro Glu Ala Val Lys Gly Glu Val Leu Lys Val Gly Asn Lys Ser Cys
385                 390                 395                 400

Glu Asn Ile His Leu His Ser Glu Ala Val Leu Cys Thr Val Pro Asn
                405                 410                 415

Asp Leu Leu Lys Leu Asn Ser Glu Leu Asn Ile Glu Trp Lys Gln Ala
            420                 425                 430

Ile Ser Ser Thr Val Leu Gly Lys Val Ile Val Gln Pro Asp Gln Asn
        435                 440                 445

Phe Thr Gly
    450


<210> SEQ ID NO 81
<211> LENGTH: 313
<212> TYPE: PRT
<213> ORGANISM: Artificial Sequence
<220> FEATURE:
<223> OTHER INFORMATION: Synthetic (TyrKc domain of c-Met)

<400> SEQUENCE: 81

Val His Phe Asn Glu Val Ile Gly Arg Gly His Phe Gly Cys Val Tyr
1               5                   10                  15

His Gly Thr Leu Leu Asp Asn Asp Gly Lys Lys Ile His Cys Ala Val
            20                  25                  30

Lys Ser Leu Asn Arg Ile Thr Asp Ile Gly Glu Val Ser Gln Phe Leu
        35                  40                  45

Thr Glu Gly Ile Ile Met Lys Asp Phe Ser His Pro Asn Val Leu Ser
    50                  55                  60

Leu Leu Gly Ile Cys Leu Arg Ser Glu Gly Ser Pro Leu Val Val Leu
65                  70                  75                  80

Pro Tyr Met Lys His Gly Asp Leu Arg Asn Phe Ile Arg Asn Glu Thr
```

```
                85                  90                  95

His Asn Pro Thr Val Lys Asp Leu Ile Gly Phe Gly Leu Gln Val Ala
            100                 105                 110

Lys Gly Met Lys Tyr Leu Ala Ser Lys Lys Phe Val His Arg Asp Leu
        115                 120                 125

Ala Ala Arg Asn Cys Met Leu Asp Glu Lys Phe Thr Val Lys Val Ala
    130                 135                 140

Asp Phe Gly Leu Ala Arg Asp Met Tyr Asp Lys Glu Tyr Tyr Ser Val
145                 150                 155                 160

His Asn Lys Thr Gly Ala Lys Leu Pro Val Lys Trp Met Ala Leu Glu
                165                 170                 175

Ser Leu Gln Thr Gln Lys Phe Thr Thr Lys Ser Asp Val Trp Ser Phe
            180                 185                 190

Gly Val Leu Leu Trp Glu Leu Met Thr Arg Gly Ala Pro Pro Tyr Pro
        195                 200                 205

Asp Val Asn Thr Phe Asp Ile Thr Val Tyr Leu Leu Gln Gly Arg Arg
    210                 215                 220

Leu Leu Gln Pro Glu Tyr Cys Pro Asp Pro Leu Tyr Glu Val Met Leu
225                 230                 235                 240

Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
            260                 265                 270

Val His Val Asn Ala Thr Tyr Val Asn Val Lys Cys Val Ala Pro Tyr
        275                 280                 285

Pro Ser Leu Leu Ser Ser Glu Asp Asn Ala Asp Asp Glu Val Asp Thr
    290                 295                 300

Arg Pro Ala Ser Phe Trp Glu Thr Ser
305                 310
```

<210> SEQ ID NO 82
<211> LENGTH: 1332
<212> TYPE: DNA
<213> ORGANISM: Artificial Sequence
<220> FEATURE:
<223> OTHER INFORMATION: Synthetic (polynucleotide encoding SEMA domain of c-Met)

<400> SEQUENCE: 82

```
ctacatgagc atcacatttt ccttggtgcc actaactaca tttatgtttt aaatgaggaa     60

gaccttcaga aggttgctga gtacaagact gggcctgtgc tggaacaccc agattgtttc    120

ccatgtcagg actgcagcag caaagccaat ttatcaggag gtgtttggaa agataacatc    180

aacatggctc tagttgtcga cacctactat gatgatcaac tcattagctg tggcagcgtc    240

aacagaggga cctgccagcg acatgtcttt ccccacaatc atactgctga catacagtcg    300

gaggttcact gcatattctc cccacagata gaagagccca gccagtgtcc tgactgtgtg    360

gtgagcgccc tgggagccaa agtcctttca tctgtaaagg accggttcat caacttcttt    420

gtaggcaata ccataaattc ttcttatttc ccagatcatc cattgcattc gatatcagtg    480

agaaggctaa aggaaacgaa agatggtttt atgtttttga cggaccagtc ctacattgat    540

gttttacctg agttcagaga ttcttacccc attaagtatg tccatgcctt tgaaagcaac    600

aattttattt acttcttgac ggtccaaagg gaaactctag atgctcagac ttttcacaca    660

agaataatca ggttctgttc cataaactct ggattgcatt cctacatgga aatgcctctg    720
```

-continued gagtgtattc tcacagaaaa gagaaaaaag agatccacaa agaaggaagt gtttaatata 780
cttcaggctg cgtatgtcag caagcctggg gcccagcttg ctagacaaat aggagccagc 840
ctgaatgatg acattctttt cggggtgttc gcacaaagca agccagattc tgccgaacca 900
atggatcgat ctgccatgtg tgcattccct atcaaatatg tcaacgactt cttcaacaag 960
atcgtcaaca aaaacaatgt gagatgtctc cagcattttt acggacccaa tcatgagcac 1020
tgctttaata ggacacttct gagaaattca tcaggctgtg aagcgcgccg tgatgaatat 1080
cgaacagagt ttaccacagc tttgcagcgc gttgacttat tcatgggtca attcagcgaa 1140
gtcctcttaa catctatatc caccttcatt aaaggagacc tcaccatagc taatcttggg 1200
acatcagagg gtcgcttcat gcaggttgtg gtttctcgat caggaccatc aacccctcat 1260
gtgaattttc tcctggactc ccatccagtg tctccagaag tgattgtgga gcatacatta 1320
aaccaaaatg gc 1332

<210> SEQ ID NO 83
<211> LENGTH: 1299
<212> TYPE: DNA
<213> ORGANISM: Artificial Sequence
<220> FEATURE:
<223> OTHER INFORMATION: Synthetic (polynucleotide encoding PSI-IPT
domain of c-Met)

<400> SEQUENCE: 83
tacacactgg ttatcactgg gaagaagatc acgaagatcc cattgaatgg cttgggctgc 60
agacatttcc agtcctgcag tcaatgcctc tctgccccac cctttgttca gtgtggctgg 120
tgccacgaca aatgtgtgcg atcggaggaa tgcctgagcg ggacatggac tcaacagatc 180
tgtctgcctg caatctacaa ggttttccca aatagtgcac cccttgaagg agggacaagg 240
ctgaccatat gtggctggga ctttggattt cggaggaata ataaatttga tttaaagaaa 300
actagagttc tccttggaaa tgagagctgc accttgactt taagtgagag cacgatgaat 360
acattgaaat gcacagttgg tcctgccatg aataagcatt tcaatatgtc cataattatt 420
tcaaatggcc acgggacaac acaatacagt acattctcct atgtggatcc tgtaataaca 480
agtatttcgc cgaaatacgg tcctatggct ggtggcactt tacttacttt aactggaaat 540
tacctaaaca gtgggaattc tagacacatt tcaattggtg gaaaaacatg tactttaaaa 600
agtgtgtcaa acagtattct tgaatgttat accccagccc aaaccatttc aactgagttt 660
gctgttaaat tgaaaattga cttagccaac cgagagacaa gcatcttcag ttaccgtgaa 720
gatcccattg tctatgaaat tcatccaacc aaatctttta ttagtggtgg gagcacaata 780
acaggtgttg ggaaaaacct gaattcagtt agtgtcccga gaatggtcat aaatgtgcat 840
gaagcaggaa ggaactttac agtggcatgt caacatcgct ctaattcaga gataatctgt 900
tgtaccactc cttccctgca acagctgaat ctgcaactcc ccctgaaaac caaagccttt 960
ttcatgttag atgggatcct ttccaaatac tttgatctca tttatgtaca taatcctgtg 1020
tttaagcctt ttgaaaagcc agtgatgatc tcaatgggca atgaaaatgt actggaaatt 1080
aagggaaatg atattgaccc tgaagcagtt aaaggtgaag tgttaaaagt tggaaataag 1140
agctgtgaga atatacactt acattctgaa gccgttttat gcacggtccc caatgacctg 1200
ctgaaattga acagcgagct aaatatagag tggaagcaag caatttcttc aaccgtcctt 1260
ggaaaagtaa tagttcaacc agatcagaat ttcacagga 1299

<210> SEQ ID NO 84

<211> LENGTH: 939
<212> TYPE: DNA
<213> ORGANISM: Artificial Sequence
<220> FEATURE:
<223> OTHER INFORMATION: Synthetic (polynucleotide encoding TyrKc domain of c-Met)

<400> SEQUENCE: 84
gtgcatttca atgaagtcat aggaagaggg cattttggtt gtgtatatca tgggactttg 60
ttggacaatg atggcaagaa aattcactgt gctgtgaaat ccttgaacag aatcactgac 120
ataggagaag tttcccaatt tctgaccgag ggaatcatca tgaaagattt tagtcatccc 180
aatgtcctct cgctcctggg aatctgcctg cgaagtgaag ggtctccgct ggtggtccta 240
ccatacatga aacatggaga tcttcgaaat ttcattcgaa atgagactca taatccaact 300
gtaaaagatc ttattggctt tggtcttcaa gtagccaaag gcatgaaata tcttgcaagc 360
aaaaagtttg tccacagaga cttggctgca agaaactgta tgctggatga aaaattcaca 420
gtcaaggttg ctgattttgg tcttgccaga gacatgtatg ataaagaata ctatagtgta 480
cacaacaaaa caggtgcaaa gctgccagtg aagtggatgg ctttggaaag tctgcaaact 540
caaaagttta ccaccaagtc agatgtgtgg tcctttggcg tgctcctctg ggagctgatg 600
acaagaggag ccccacctta tcctgacgta aacacctttg atataactgt ttacttgttg 660
caagggagaa gactcctaca acccgaatac tgcccagacc ccttatatga agtaatgcta 720
aaatgctggc accctaaagc cgaaatgcgc ccatcctttt ctgaactggt gtcccggata 780
tcagcgatct tctctacttt cattggggag cactatgtcc atgtgaacgc tacttatgtg 840
aacgtaaaat gtgtcgctcc gtatccttct ctgttgtcat cagaagataa cgctgatgat 900
gaggtggaca cacgaccagc ctccttctgg gagacatca 939

<210> SEQ ID NO 85
<211> LENGTH: 13
<212> TYPE: PRT
<213> ORGANISM: Artificial Sequence
<220> FEATURE:
<223> OTHER INFORMATION: Synthetic (heavy chain CDR3 of anti-c-Met antibody)

<400> SEQUENCE: 85

Asp Asn Trp Phe Ala Tyr Trp Gly Gln Gly Thr Leu Val
1 5 10

<210> SEQ ID NO 86
<211> LENGTH: 10
<212> TYPE: PRT
<213> ORGANISM: Artificial Sequence
<220> FEATURE:
<223> OTHER INFORMATION: Synthetic (light chain CDR3 of anti-c-Met antibody)

<400> SEQUENCE: 86

Leu Thr Phe Gly Ala Gly Thr Lys Leu Glu
1 5 10

<210> SEQ ID NO 87
<211> LENGTH: 117
<212> TYPE: PRT
<213> ORGANISM: Artificial Sequence
<220> FEATURE:
<223> OTHER INFORMATION: Synthetic (heavy chain variable region of monoclonal antibody AbF46)

<400> SEQUENCE: 87

```
Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asp Thr Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ala
        115


<210> SEQ ID NO 88
<211> LENGTH: 114
<212> TYPE: PRT
<213> ORGANISM: Artificial Sequence
<220> FEATURE:
<223> OTHER INFORMATION: Synthetic (light chain variable region of
      anti-c-Met antibody)

<400> SEQUENCE: 88

Asp Ile Leu Met Thr Gln Ser Pro Ser Ser Leu Thr Val Ser Ala Gly
1               5                   10                  15

Glu Lys Val Thr Met Ser Cys Lys Ser Ser Gln Ser Leu Leu Ala Ser
            20                  25                  30

Gly Asn Gln Asn Asn Tyr Leu Ala Trp His Gln Gln Lys Pro Gly Arg
        35                  40                  45

Ser Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Gln
                85                  90                  95

Ser Tyr Ser Ala Pro Leu Thr Phe Gly Ala Gly Thr Lys Leu Glu Leu
            100                 105                 110

Lys Arg


<210> SEQ ID NO 89
<211> LENGTH: 17
<212> TYPE: PRT
<213> ORGANISM: Artificial Sequence
<220> FEATURE:
<223> OTHER INFORMATION: Synthetic (light chain CDR3 of anti-c-Met
      antibody)

<400> SEQUENCE: 89

Gln Gln Ser Tyr Ser Ala Pro Leu Thr Phe Gly Ala Gly Thr Lys Leu
1               5                   10                  15

Glu


<210> SEQ ID NO 90
<211> LENGTH: 117
<212> TYPE: PRT
```

```
<213> ORGANISM: Artificial Sequence
<220> FEATURE:
<223> OTHER INFORMATION: Synthetic (heavy chain variable region of
      AT-VH1)

<400> SEQUENCE: 90

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Ser Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115


<210> SEQ ID NO 91
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH2)

<400> SEQUENCE: 91

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115


<210> SEQ ID NO 92
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH3)

<400> SEQUENCE: 92

Glu Val Gln Leu Val Glu Ser Gly Gly Gly Leu Val Gln Pro Gly Gly
1               5                   10                  15
```

```
Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Ser Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115


<210> SEQ ID NO 93
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH4)

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115


<210> SEQ ID NO 94
<211> LENGTH: 117
<212> TYPE: PRT
<213> ORGANISM: Artificial Sequence
<220> FEATURE:
<223> OTHER INFORMATION: Synthetic (heavy chain variable region of
      AT-VH5)

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60
```

```
Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115


<210> SEQ ID NO 95
<211> LENGTH: 114
<212> TYPE: PRT
<213> ORGANISM: Artificial Sequence
<220> FEATURE:
<223> OTHER INFORMATION: Synthetic (light chain variable region of
      anti c-Met humanized antibody(huAbF46-H4))

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg


<210> SEQ ID NO 96
<211> LENGTH: 113
<212> TYPE: PRT
<213> ORGANISM: Artificial Sequence
<220> FEATURE:
<223> OTHER INFORMATION: Synthetic (light chain variable region of
      AT-Vk1)

<400> SEQUENCE: 96

Asp Ile Leu Met Thr Gln Ser Pro Ser Ser Leu Thr Ala Ser Val Gly
1               5                   10                  15

Asp Arg Val Thr Met Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110
```

Lys

<210> SEQ ID NO 97
<211> LENGTH: 113
<212> TYPE: PRT
<213> ORGANISM: Artificial Sequence
<220> FEATURE:
<223> OTHER INFORMATION: Synthetic (light chain variable region of AT-Vk2)

<400> SEQUENCE: 97

```
Asp Ile Leu Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys
```

<210> SEQ ID NO 98
<211> LENGTH: 113
<212> TYPE: PRT
<213> ORGANISM: Artificial Sequence
<220> FEATURE:
<223> OTHER INFORMATION: Synthetic (light chain variable region of AT-Vk3)

<400> SEQUENCE: 98

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys
```

<210> SEQ ID NO 99
<211> LENGTH: 113
<212> TYPE: PRT
<213> ORGANISM: Artificial Sequence
<220> FEATURE:
<223> OTHER INFORMATION: Synthetic (light chain variable region of AT-Vk4)

<400> SEQUENCE: 99

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys
```

<210> SEQ ID NO 100
<211> LENGTH: 13
<212> TYPE: PRT
<213> ORGANISM: Artificial Sequence
<220> FEATURE:
<223> OTHER INFORMATION: Synthetic (modified hinge region(U7-HC6))

<400> SEQUENCE: 100

```
Glu Pro Ser Cys Asp Lys His Cys Cys Pro Pro Cys Pro
1               5                   10
```

<210> SEQ ID NO 101
<211> LENGTH: 13
<212> TYPE: PRT
<213> ORGANISM: Artificial Sequence
<220> FEATURE:
<223> OTHER INFORMATION: Synthetic (modified hinge region(U6-HC7))

<400> SEQUENCE: 101

```
Glu Pro Lys Ser Cys Asp Cys His Cys Pro Pro Cys Pro
1               5                   10
```

<210> SEQ ID NO 102
<211> LENGTH: 12
<212> TYPE: PRT
<213> ORGANISM: Artificial Sequence
<220> FEATURE:
<223> OTHER INFORMATION: Synthetic (modified hinge region(U3-HC9))

<400> SEQUENCE: 102

```
Glu Arg Lys Cys Cys Val Glu Cys Pro Pro Cys Pro
1               5                   10
```

<210> SEQ ID NO 103
<211> LENGTH: 14
<212> TYPE: PRT
<213> ORGANISM: Artificial Sequence
<220> FEATURE:
<223> OTHER INFORMATION: Synthetic (modified hinge region(U6-HC8))

<400> SEQUENCE: 103

```
Glu Pro Arg Asp Cys Gly Cys Lys Pro Cys Pro Pro Cys Pro
1               5                   10
```

<210> SEQ ID NO 104

-continued

<211> LENGTH: 13
<212> TYPE: PRT
<213> ORGANISM: Artificial Sequence
<220> FEATURE:
<223> OTHER INFORMATION: Synthetic (modified hinge region(U8-HC5))

<400> SEQUENCE: 104

Glu Lys Cys Asp Lys Thr His Thr Cys Pro Pro Cys Pro
1 5 10

<210> SEQ ID NO 105
<211> LENGTH: 15
<212> TYPE: PRT
<213> ORGANISM: Artificial Sequence
<220> FEATURE:
<223> OTHER INFORMATION: Synthetic (human hinge region)

<400> SEQUENCE: 105

Glu Pro Lys Ser Cys Asp Lys Thr His Thr Cys Pro Pro Cys Pro
1 5 10 15

<210> SEQ ID NO 106
<211> LENGTH: 17
<212> TYPE: PRT
<213> ORGANISM: Artificial Sequence
<220> FEATURE:
<223> OTHER INFORMATION: Synthetic (CDR-L1 of antibody L3-11Y)

<400> SEQUENCE: 106

Lys Ser Ser Gln Ser Leu Leu Ala Trp Gly Asn Gln Asn Asn Tyr Leu
1 5 10 15

Ala

<210> SEQ ID NO 107
<211> LENGTH: 114
<212> TYPE: PRT
<213> ORGANISM: Artificial Sequence
<220> FEATURE:
<223> OTHER INFORMATION: Synthetic (amino acid sequence of light chain
variable region of antibody L3-11Y)

<400> SEQUENCE: 107

Asp Ile Gln Met Thr Gln Ser Pro Ser Ser Leu Ser Ala Ser Val Gly
1 5 10 15

Asp Arg Val Thr Ile Thr Cys Lys Ser Ser Gln Ser Leu Leu Ala Trp
20 25 30

Gly Asn Gln Asn Asn Tyr Leu Ala Trp Tyr Gln Gln Lys Pro Gly Lys
35 40 45

Ala Pro Lys Met Leu Ile Ile Trp Ala Ser Thr Arg Val Ser Gly Val
50 55 60

Pro Ser Arg Phe Ser Gly Ser Gly Ser Gly Thr Asp Phe Thr Leu Thr
65 70 75 80

Ile Ser Ser Leu Gln Pro Glu Asp Phe Ala Thr Tyr Tyr Cys Gln Gln
85 90 95

Ser Tyr Ser Arg Pro Tyr Thr Phe Gly Gln Gly Thr Lys Val Glu Ile
100 105 110

Lys Arg

<210> SEQ ID NO 108
<211> LENGTH: 220
<212> TYPE: PRT
<213> ORGANISM: Artificial Sequence
<220> FEATURE:

<223> OTHER INFORMATION: Synthetic (amino acid sequence of light chain
of antibody L3-11Y)

<400> SEQUENCE: 108

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Trp
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 109
<211> LENGTH: 5
<212> TYPE: PRT
<213> ORGANISM: Artificial Sequence
<220> FEATURE:
<223> OTHER INFORMATION: Synthetic (CDR-H1 of anti-Ang2 antibody)

<400> SEQUENCE: 109

```
Asp Tyr Ala Met Ser
1               5
```

<210> SEQ ID NO 110
<211> LENGTH: 5
<212> TYPE: PRT
<213> ORGANISM: Artificial Sequence
<220> FEATURE:
<223> OTHER INFORMATION: Synthetic (CDR-H1 of anti-Ang2 antibody)

<400> SEQUENCE: 110

```
Asp Tyr Tyr Met Ser
1               5
```

<210> SEQ ID NO 111
<211> LENGTH: 5
<212> TYPE: PRT
<213> ORGANISM: Artificial Sequence
<220> FEATURE:

<223> OTHER INFORMATION: Synthetic (CDR-H1 of anti-Ang2 antibody)

<400> SEQUENCE: 111

Asn Tyr Ala Met Ser
1 5

<210> SEQ ID NO 112
<211> LENGTH: 5
<212> TYPE: PRT
<213> ORGANISM: Artificial Sequence
<220> FEATURE:
<223> OTHER INFORMATION: Synthetic (CDR-H1 of anti-Ang2 antibody)

<400> SEQUENCE: 112

Asp Tyr Asp Met Ser
1 5

<210> SEQ ID NO 113
<211> LENGTH: 5
<212> TYPE: PRT
<213> ORGANISM: Artificial Sequence
<220> FEATURE:
<223> OTHER INFORMATION: Synthetic (CDR-H1 of anti-Ang2 antibody)

<400> SEQUENCE: 113

Ser Tyr Asp Met Ser
1 5

<210> SEQ ID NO 114
<211> LENGTH: 5
<212> TYPE: PRT
<213> ORGANISM: Artificial Sequence
<220> FEATURE:
<223> OTHER INFORMATION: Synthetic (CDR-H1 of anti-Ang2 antibody)

<400> SEQUENCE: 114

Asp Tyr Asp Met Ser
1 5

<210> SEQ ID NO 115
<211> LENGTH: 17
<212> TYPE: PRT
<213> ORGANISM: Artificial Sequence
<220> FEATURE:
<223> OTHER INFORMATION: Synthetic (CDR-H2 of anti-Ang2 antibody)

<400> SEQUENCE: 115

Ala Ile Tyr Pro Asp Ser Gly Asn Lys Tyr Tyr Ala Asp Ser Val Lys
1 5 10 15

Gly

<210> SEQ ID NO 116
<211> LENGTH: 17
<212> TYPE: PRT
<213> ORGANISM: Artificial Sequence
<220> FEATURE:
<223> OTHER INFORMATION: Synthetic (CDR-H2 of anti-Ang2 antibody)

<400> SEQUENCE: 116

Gly Ile Tyr Pro Ser Gly Gly Ser Thr Tyr Tyr Ala Asp Ser Val Lys
1 5 10 15

Gly

<210> SEQ ID NO 117
<211> LENGTH: 17

<212> TYPE: PRT
<213> ORGANISM: Artificial Sequence
<220> FEATURE:
<223> OTHER INFORMATION: Synthetic (CDR-H2 of anti-Ang2 antibody)

<400> SEQUENCE: 117

Ala Ile Ser Ser Gly Gly Gly Asn Ile Tyr Tyr Ala Asp Ser Val Lys
1 5 10 15

Gly

<210> SEQ ID NO 118
<211> LENGTH: 17
<212> TYPE: PRT
<213> ORGANISM: Artificial Sequence
<220> FEATURE:
<223> OTHER INFORMATION: Synthetic (CDR-H2 of anti-Ang2 antibody)

<400> SEQUENCE: 118

Ser Ile Tyr Pro Asp Asp Gly Asn Thr Tyr Tyr Ala Asp Ser Val Lys
1 5 10 15

Gly

<210> SEQ ID NO 119
<211> LENGTH: 17
<212> TYPE: PRT
<213> ORGANISM: Artificial Sequence
<220> FEATURE:
<223> OTHER INFORMATION: Synthetic (CDR-H2 of anti-Ang2 antibody)

<400> SEQUENCE: 119

Ser Ile Ser His Gly Asp Ser Asn Lys Tyr Tyr Ala Asp Ser Val Lys
1 5 10 15

Gly

<210> SEQ ID NO 120
<211> LENGTH: 17
<212> TYPE: PRT
<213> ORGANISM: Artificial Sequence
<220> FEATURE:
<223> OTHER INFORMATION: Synthetic (CDR-H2 of anti-Ang2 antibody)

<400> SEQUENCE: 120

Leu Ile Ser Pro Asp Ser Ser Ser Ile Tyr Tyr Ala Asp Ser Val Lys
1 5 10 15

Gly

<210> SEQ ID NO 121
<211> LENGTH: 17
<212> TYPE: PRT
<213> ORGANISM: Artificial Sequence
<220> FEATURE:
<223> OTHER INFORMATION: Synthetic (CDR-H2 of anti-Ang2 antibody)

<400> SEQUENCE: 121

Gly Ile Ser Ser Asp Asp Gly Asn Thr Tyr Tyr Ala Asp Ser Val Lys
1 5 10 15

Gly

<210> SEQ ID NO 122
<211> LENGTH: 20
<212> TYPE: PRT
<213> ORGANISM: Artificial Sequence
<220> FEATURE:
<223> OTHER INFORMATION: Synthetic (CDR-H3 of anti-Ang2 antibody)

<400> SEQUENCE: 122

Ala Arg His Ser Ser Asp Pro Lys Val Lys Ser Gly Tyr Tyr Asp Asp
1               5                   10                  15

Gly Met Asp Val
            20

<210> SEQ ID NO 123
<211> LENGTH: 14
<212> TYPE: PRT
<213> ORGANISM: Artificial Sequence
<220> FEATURE:
<223> OTHER INFORMATION: Synthetic (CDR-H3 of anti-Ang2 antibody)

<400> SEQUENCE: 123

Ala Arg Asp Pro Ser Thr Leu Thr Tyr Ala Gly Phe Asp Tyr
1               5                   10

<210> SEQ ID NO 124
<211> LENGTH: 20
<212> TYPE: PRT
<213> ORGANISM: Artificial Sequence
<220> FEATURE:
<223> OTHER INFORMATION: Synthetic (CDR-H3 of anti-Ang2 antibody)

<400> SEQUENCE: 124

Ala Lys Ser Gly Ile Gln Pro Ser Pro Pro Ser Met Ser Ser Ala Tyr
1               5                   10                  15

Ala Met Asp Val
            20

<210> SEQ ID NO 125
<211> LENGTH: 20
<212> TYPE: PRT
<213> ORGANISM: Artificial Sequence
<220> FEATURE:
<223> OTHER INFORMATION: Synthetic (CDR-H3 of anti-Ang2 antibody)

<400> SEQUENCE: 125

Ala Arg His Thr Ser His His Thr Ser Ile Asp Gly Tyr Tyr Tyr Tyr
1               5                   10                  15

Gly Met Asp Gly
            20

<210> SEQ ID NO 126
<211> LENGTH: 20
<212> TYPE: PRT
<213> ORGANISM: Artificial Sequence
<220> FEATURE:
<223> OTHER INFORMATION: Synthetic (CDR-H3 of anti-Ang2 antibody)

<400> SEQUENCE: 126

Ala Lys Ser Ser Gly Ile Gln Glu Ser Pro Pro Thr Tyr Tyr Tyr Tyr
1               5                   10                  15

Gly Met Asp Val
            20

<210> SEQ ID NO 127
<211> LENGTH: 20
<212> TYPE: PRT
<213> ORGANISM: Artificial Sequence
<220> FEATURE:
<223> OTHER INFORMATION: Synthetic (CDR-H3 of anti-Ang2 antibody)

<400> SEQUENCE: 127

Ala Lys His Pro Val Arg Leu Asn Leu His Pro Met Tyr Tyr Tyr Tyr
1 5 10 15

Gly Met Asp Val
20

<210> SEQ ID NO 128
<211> LENGTH: 14
<212> TYPE: PRT
<213> ORGANISM: Artificial Sequence
<220> FEATURE:
<223> OTHER INFORMATION: Synthetic (CDR-H3 of anti-Ang2 antibody)

<400> SEQUENCE: 128

Ala Lys Asp Leu Ile Ser Phe Trp Arg Gly Gly Phe Asp Tyr
1 5 10

<210> SEQ ID NO 129
<211> LENGTH: 20
<212> TYPE: PRT
<213> ORGANISM: Artificial Sequence
<220> FEATURE:
<223> OTHER INFORMATION: Synthetic (CDR-H3 of anti-Ang2 antibody)

<400> SEQUENCE: 129

Ala Arg Pro Thr Ile Asp Lys Tyr Thr Leu Arg Gly Tyr Tyr Ser Tyr
1 5 10 15

Gly Met Asp Val
20

<210> SEQ ID NO 130
<211> LENGTH: 13
<212> TYPE: PRT
<213> ORGANISM: Artificial Sequence
<220> FEATURE:
<223> OTHER INFORMATION: Synthetic (CDR-L1 of anti-Ang2 antibody)

<400> SEQUENCE: 130

Ser Gly Ser Ser Ser Asn Ile Gly Asn Asn Ala Val Asn
1 5 10

<210> SEQ ID NO 131
<211> LENGTH: 13
<212> TYPE: PRT
<213> ORGANISM: Artificial Sequence
<220> FEATURE:
<223> OTHER INFORMATION: Synthetic (CDR-L1 of anti-Ang2 antibody)

<400> SEQUENCE: 131

Ser Gly Ser Ser Ser Asn Ile Gly Asn Asn Tyr Val Thr
1 5 10

<210> SEQ ID NO 132
<211> LENGTH: 13
<212> TYPE: PRT
<213> ORGANISM: Artificial Sequence
<220> FEATURE:
<223> OTHER INFORMATION: Synthetic (CDR-L1 of anti-Ang2 antibody)

<400> SEQUENCE: 132

Ser Gly Ser Ser Ser Asn Ile Gly Asn Asn Asp Val Tyr
1 5 10

<210> SEQ ID NO 133
<211> LENGTH: 13
<212> TYPE: PRT

<213> ORGANISM: Artificial Sequence
<220> FEATURE:
<223> OTHER INFORMATION: Synthetic (CDR-L1 of anti-Ang2 antibody)

<400> SEQUENCE: 133

Thr Gly Ser Ser Ser Asn Ile Gly Asn Asn Asp Val Ser
1 5 10

<210> SEQ ID NO 134
<211> LENGTH: 13
<212> TYPE: PRT
<213> ORGANISM: Artificial Sequence
<220> FEATURE:
<223> OTHER INFORMATION: Synthetic (CDR-L1 of anti-Ang2 antibody)

<400> SEQUENCE: 134

Ser Gly Ser Ser Ser Asn Ile Gly Ser Asn Ala Val Asn
1 5 10

<210> SEQ ID NO 135
<211> LENGTH: 13
<212> TYPE: PRT
<213> ORGANISM: Artificial Sequence
<220> FEATURE:
<223> OTHER INFORMATION: Synthetic (CDR-L1 of anti-Ang2 antibody)

<400> SEQUENCE: 135

Thr Gly Ser Ser Ser Asn Ile Gly Asn Asn Ala Val Ser
1 5 10

<210> SEQ ID NO 136
<211> LENGTH: 13
<212> TYPE: PRT
<213> ORGANISM: Artificial Sequence
<220> FEATURE:
<223> OTHER INFORMATION: Synthetic (CDR-L1 of anti-Ang2 antibody)

<400> SEQUENCE: 136

Ser Gly Ser Ser Ser Asn Ile Gly Ser Asn Tyr Val Asn
1 5 10

<210> SEQ ID NO 137
<211> LENGTH: 13
<212> TYPE: PRT
<213> ORGANISM: Artificial Sequence
<220> FEATURE:
<223> OTHER INFORMATION: Synthetic (CDR-L1 of anti-Ang2 antibody)

<400> SEQUENCE: 137

Thr Gly Ser Ser Ser Asn Ile Gly Ser Asn Tyr Val Ser
1 5 10

<210> SEQ ID NO 138
<211> LENGTH: 7
<212> TYPE: PRT
<213> ORGANISM: Artificial Sequence
<220> FEATURE:
<223> OTHER INFORMATION: Synthetic (CDR-L2 of anti-Ang2 antibody)

<400> SEQUENCE: 138

Ala Asp Ser Asn Arg Pro Ser
1 5

<210> SEQ ID NO 139
<211> LENGTH: 7
<212> TYPE: PRT
<213> ORGANISM: Artificial Sequence
<220> FEATURE:
<223> OTHER INFORMATION: Synthetic (CDR-L2 of anti-Ang2 antibody)

<400> SEQUENCE: 139

Ala Asp Ser His Arg Pro Ser
1 5

<210> SEQ ID NO 140
<211> LENGTH: 7
<212> TYPE: PRT
<213> ORGANISM: Artificial Sequence
<220> FEATURE:
<223> OTHER INFORMATION: Synthetic (CDR-L2 of anti-Ang2 antibody)

<400> SEQUENCE: 140

Ala Asn Ser His Arg Pro Ser
1 5

<210> SEQ ID NO 141
<211> LENGTH: 7
<212> TYPE: PRT
<213> ORGANISM: Artificial Sequence
<220> FEATURE:
<223> OTHER INFORMATION: Synthetic (CDR-L2 of anti-Ang2 antibody)

<400> SEQUENCE: 141

Ser Asp Ser Lys Arg Pro Ser
1 5

<210> SEQ ID NO 142
<211> LENGTH: 7
<212> TYPE: PRT
<213> ORGANISM: Artificial Sequence
<220> FEATURE:
<223> OTHER INFORMATION: Synthetic (CDR-L2 of anti-Ang2 antibody)

<400> SEQUENCE: 142

Ser Asp Ser Gln Arg Pro Ser
1 5

<210> SEQ ID NO 143
<211> LENGTH: 7
<212> TYPE: PRT
<213> ORGANISM: Artificial Sequence
<220> FEATURE:
<223> OTHER INFORMATION: Synthetic (CDR-L2 of anti-Ang2 antibody)

<400> SEQUENCE: 143

Ser Asp Ser His Arg Pro Ser
1 5

<210> SEQ ID NO 144
<211> LENGTH: 7
<212> TYPE: PRT
<213> ORGANISM: Artificial Sequence
<220> FEATURE:
<223> OTHER INFORMATION: Synthetic (CDR-L2 of anti-Ang2 antibody)

<400> SEQUENCE: 144

Ser Asp Asn Lys Arg Pro Ser
1 5

<210> SEQ ID NO 145
<211> LENGTH: 9
<212> TYPE: PRT
<213> ORGANISM: Artificial Sequence
<220> FEATURE:

<223> OTHER INFORMATION: Synthetic (CDR-L3 of anti-Ang2 antibody)

<400> SEQUENCE: 145

Gly Ser Trp Asp Tyr Ser Leu Ser Gly
1 5

<210> SEQ ID NO 146
<211> LENGTH: 9
<212> TYPE: PRT
<213> ORGANISM: Artificial Sequence
<220> FEATURE:
<223> OTHER INFORMATION: Synthetic (CDR-L3 of anti-Ang2 antibody)

<400> SEQUENCE: 146

Ala Thr Trp Asp Tyr Ser Leu Ser Gly
1 5

<210> SEQ ID NO 147
<211> LENGTH: 9
<212> TYPE: PRT
<213> ORGANISM: Artificial Sequence
<220> FEATURE:
<223> OTHER INFORMATION: Synthetic (CDR-L3 of anti-Ang2 antibody)

<400> SEQUENCE: 147

Gly Thr Trp Asp Tyr Ser Leu Ser Gly
1 5

<210> SEQ ID NO 148
<211> LENGTH: 9
<212> TYPE: PRT
<213> ORGANISM: Artificial Sequence
<220> FEATURE:
<223> OTHER INFORMATION: Synthetic (CDR-L3 of anti-Ang2 antibody)

<400> SEQUENCE: 148

Ala Thr Trp Asp Tyr Ser Leu Ser Ala
1 5

<210> SEQ ID NO 149
<211> LENGTH: 9
<212> TYPE: PRT
<213> ORGANISM: Artificial Sequence
<220> FEATURE:
<223> OTHER INFORMATION: Synthetic (CDR-L3 of anti-Ang2 antibody)

<400> SEQUENCE: 149

Gly Ala Trp Asp Asp Ser Leu Ser Gly
1 5

<210> SEQ ID NO 150
<211> LENGTH: 9
<212> TYPE: PRT
<213> ORGANISM: Artificial Sequence
<220> FEATURE:
<223> OTHER INFORMATION: Synthetic (CDR-L3 of anti-Ang2 antibody)

<400> SEQUENCE: 150

Gly Thr Trp Asp Asp Ser Leu Asn Gly
1 5

<210> SEQ ID NO 151
<211> LENGTH: 5
<212> TYPE: PRT
<213> ORGANISM: Artificial Sequence
<220> FEATURE:
<223> OTHER INFORMATION: Synthetic (CDR-H1 of anti-Ang2 antibody)

<220> FEATURE:
<221> NAME/KEY: VARIANT
<222> LOCATION: (1)
<223> OTHER INFORMATION: Xaa is Asp (D), Ser(S), or Asn(N), for example, Asp (D) or Asn(N)
<220> FEATURE:
<221> NAME/KEY: VARIANT
<222> LOCATION: (3)
<223> OTHER INFORMATION: Xaa is Ala(A), Asp(D), or Tyr(Y)

<400> SEQUENCE: 151

Xaa Tyr Xaa Met Ser
1               5

<210> SEQ ID NO 152
<211> LENGTH: 17
<212> TYPE: PRT
<213> ORGANISM: Artificial Sequence
<220> FEATURE:
<223> OTHER INFORMATION: Synthetic (CDR-H2 of anti-Ang2 antibody)
<220> FEATURE:
<221> NAME/KEY: VARIANT
<222> LOCATION: (1)
<223> OTHER INFORMATION: Xaa is Ala(A), Gly(G), Leu(L), or Ser(S), for example, Ala(A), Gly(G), or Ser(S)
<220> FEATURE:
<221> NAME/KEY: VARIANT
<222> LOCATION: (3)
<223> OTHER INFORMATION: Xaa is Tyr(Y) or Ser(S)
<220> FEATURE:
<221> NAME/KEY: VARIANT
<222> LOCATION: (4)
<223> OTHER INFORMATION: Xaa is Pro(P), His(H), or Ser(S)
<220> FEATURE:
<221> NAME/KEY: VARIANT
<222> LOCATION: (5)
<223> OTHER INFORMATION: Xaa is Asp (D), Gly(G), or Ser(S)
<220> FEATURE:
<221> NAME/KEY: VARIANT
<222> LOCATION: (6)
<223> OTHER INFORMATION: Xaa is Ser(S), Gly(G), or Asp(D)
<220> FEATURE:
<221> NAME/KEY: VARIANT
<222> LOCATION: (7)
<223> OTHER INFORMATION: Xaa is Gly(G) or Ser(S)
<220> FEATURE:
<221> NAME/KEY: VARIANT
<222> LOCATION: (8)
<223> OTHER INFORMATION: Xaa is Asn(N) or Ser(S)
<220> FEATURE:
<221> NAME/KEY: VARIANT
<222> LOCATION: (9)
<223> OTHER INFORMATION: Xaa is Lys(K), Ile(I), or Thr(T)

<400> SEQUENCE: 152

Xaa Ile Xaa Xaa Xaa Xaa Xaa Xaa Xaa Tyr Tyr Ala Asp Ser Val Lys
1               5                   10                  15

Gly

<210> SEQ ID NO 153
<211> LENGTH: 13
<212> TYPE: PRT
<213> ORGANISM: Artificial Sequence
<220> FEATURE:
<223> OTHER INFORMATION: Synthetic (CDR-L1 of anti-Ang2 antibody)
<220> FEATURE:
<221> NAME/KEY: VARIANT
<222> LOCATION: (1)
<223> OTHER INFORMATION: Xaa is Ser(S) or Thr(T)
<220> FEATURE:
<221> NAME/KEY: VARIANT
<222> LOCATION: (9)
<223> OTHER INFORMATION: Xaa is Asn(N) or Ser(S)
<220> FEATURE:

<221> NAME/KEY: VARIANT
<222> LOCATION: (11)
<223> OTHER INFORMATION: Xaa is Ala(A), Tyr(Y), or Asp(D)
<220> FEATURE:
<221> NAME/KEY: VARIANT
<222> LOCATION: (13)
<223> OTHER INFORMATION: Xaa is Asn(N), Ser(S), Thr(T), or Tyr(Y)

<400> SEQUENCE: 153

```
Xaa Gly Ser Ser Ser Asn Ile Gly Xaa Asn Xaa Val Xaa
1               5                   10
```

<210> SEQ ID NO 154
<211> LENGTH: 7
<212> TYPE: PRT
<213> ORGANISM: Artificial Sequence
<220> FEATURE:
<223> OTHER INFORMATION: Synthetic (CDR-L2 of anti-Ang2 antibody)
<220> FEATURE:
<221> NAME/KEY: VARIANT
<222> LOCATION: (1)
<223> OTHER INFORMATION: Xaa is Ala(A) or Ser(S)
<220> FEATURE:
<221> NAME/KEY: VARIANT
<222> LOCATION: (2)
<223> OTHER INFORMATION: Xaa is Asp(D) or Asn(N)
<220> FEATURE:
<221> NAME/KEY: VARIANT
<222> LOCATION: (3)
<223> OTHER INFORMATION: Xaa is Ser(S) or Asn(N), for example, Ser(S)
<220> FEATURE:
<221> NAME/KEY: VARIANT
<222> LOCATION: (4)
<223> OTHER INFORMATION: Xaa is Asn(N), Lys(K), His(H), or Gln(Q)

<400> SEQUENCE: 154

```
Xaa Xaa Xaa Xaa Arg Pro Ser
1               5
```

<210> SEQ ID NO 155
<211> LENGTH: 9
<212> TYPE: PRT
<213> ORGANISM: Artificial Sequence
<220> FEATURE:
<223> OTHER INFORMATION: Synthetic (CDR-L3 of anti-Ang2 antibody)
<220> FEATURE:
<221> NAME/KEY: VARIANT
<222> LOCATION: (1)
<223> OTHER INFORMATION: Xaa is Gly(G) or Ala(A)
<220> FEATURE:
<221> NAME/KEY: VARIANT
<222> LOCATION: (2)
<223> OTHER INFORMATION: Xaa is Ser(S), Ala(A), or Thr(T), for example
      Ser(S) or Thr(T)
<220> FEATURE:
<221> NAME/KEY: VARIANT
<222> LOCATION: (5)
<223> OTHER INFORMATION: Xaa is Tyr(Y), or Asp(D), for example, Tyr(Y)
<220> FEATURE:
<221> NAME/KEY: VARIANT
<222> LOCATION: (8)
<223> OTHER INFORMATION: Xaa is Ser(S) or Asn(N), for example, Ser(S)
<220> FEATURE:
<221> NAME/KEY: VARIANT
<222> LOCATION: (9)
<223> OTHER INFORMATION: Xaa is Gly(G) or Ala(A)

<400> SEQUENCE: 155

```
Xaa Xaa Trp Asp Xaa Ser Leu Xaa Xaa
1               5
```

<210> SEQ ID NO 156
<211> LENGTH: 127

<212> TYPE: PRT
<213> ORGANISM: Artificial Sequence
<220> FEATURE:
<223> OTHER INFORMATION: Synthetic (Heavy chain variable region of anti-Ang2 antibody 2-E6)

<400> SEQUENCE: 156

```
Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Ala Ile Tyr Pro Asp Ser Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ser Ser Asp Pro Lys Val Lys Ser Gly Tyr Tyr Asp Asp
            100                 105                 110

Gly Met Asp Val Trp Gly Gln Gly Thr Leu Val Ala Val Ser Ser
        115                 120                 125
```

<210> SEQ ID NO 157
<211> LENGTH: 121
<212> TYPE: PRT
<213> ORGANISM: Artificial Sequence
<220> FEATURE:
<223> OTHER INFORMATION: Synthetic (Heavy chain variable region of anti-Ang2 antibody 8-A5)

<400> SEQUENCE: 157

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Pro Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Ser Thr Leu Thr Tyr Ala Gly Phe Asp Tyr Trp Gly
            100                 105                 110

Gln Gly Thr Leu Val Thr Val Ser Ser
        115                 120
```

<210> SEQ ID NO 158
<211> LENGTH: 127
<212> TYPE: PRT
<213> ORGANISM: Artificial Sequence
<220> FEATURE:
<223> OTHER INFORMATION: Synthetic (Heavy chain variable region of anti-Ang2 antibody 7-C9)

<400> SEQUENCE: 158

```
Glu Val Gln Leu Leu Glu Ser Gly Gly Gly Leu Val Gln Pro Gly Gly
```

```
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Ser Gly Gly Gly Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Gly Ile Gln Pro Ser Pro Pro Ser Met Ser Ser Ala Tyr
            100                 105                 110

Ala Met Asp Val Trp Gly Gln Gly Thr Leu Val Thr Val Ser Ser
        115                 120                 125


<210> SEQ ID NO 159
<211> LENGTH: 127
<212> TYPE: PRT
<213> ORGANISM: Artificial Sequence
<220> FEATURE:
<223> OTHER INFORMATION: Synthetic (Heavy chain variable region of
      anti-Ang2 antibody 4-C11)

<400> SEQUENCE: 159

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Ser Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Thr Ser His His Thr Ser Ile Asp Gly Tyr Tyr Tyr Tyr
            100                 105                 110

Gly Met Asp Gly Trp Gly Gln Gly Thr Leu Val Thr Val Ser Ser
        115                 120                 125


<210> SEQ ID NO 160
<211> LENGTH: 127
<212> TYPE: PRT
<213> ORGANISM: Artificial Sequence
<220> FEATURE:
<223> OTHER INFORMATION: Synthetic (Heavy chain variable region of
      anti-Ang2 antibody 4-F5)

<400> SEQUENCE: 160

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Ser Ser Ile Ser His Gly Asp Ser Asn Lys Tyr Tyr Ala Asp Ser Val
```

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Gly Ile Gln Glu Ser Pro Pro Thr Tyr Tyr Tyr Tyr
            100                 105                 110

Gly Met Asp Val Trp Gly Gln Gly Thr Leu Val Thr Val Ser Ser
        115                 120                 125


<210> SEQ ID NO 161
<211> LENGTH: 127
<212> TYPE: PRT
<213> ORGANISM: Artificial Sequence
<220> FEATURE:
<223> OTHER INFORMATION: Synthetic (Heavy chain variable region of
      anti-Ang2 antibody 4-F11)

<400> SEQUENCE: 161

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Ser Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Pro Val Arg Leu Asn Leu His Pro Met Tyr Tyr Tyr Tyr
            100                 105                 110

Gly Met Asp Val Trp Gly Gln Gly Thr Leu Val Thr Val Ser Ser
        115                 120                 125


<210> SEQ ID NO 162
<211> LENGTH: 121
<212> TYPE: PRT
<213> ORGANISM: Artificial Sequence
<220> FEATURE:
<223> OTHER INFORMATION: Synthetic (Heavy chain variable region of
      anti-Ang2 antibody 4-H10)

<400> SEQUENCE: 162

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Leu Ile Ser Pro Asp Ser Ser Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Ile Ser Phe Trp Arg Gly Gly Phe Asp Tyr Trp Gly
```

```
            100                 105                 110

Gln Gly Thr Leu Val Thr Val Ser Ser
        115                 120


<210> SEQ ID NO 163
<211> LENGTH: 127
<212> TYPE: PRT
<213> ORGANISM: Artificial Sequence
<220> FEATURE:
<223> OTHER INFORMATION: Synthetic (Heavy chain variable region of
      anti-Ang2 antibody 3-D3)

<400> SEQUENCE: 163

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Ser Trp Val Arg Gln Ala Pro Gly Lys Gly Leu Glu Trp Val
        35                  40                  45

Ser Gly Ile Ser Ser Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Thr Ile Asp Lys Tyr Thr Leu Arg Gly Tyr Tyr Ser Tyr
            100                 105                 110

Gly Met Asp Val Trp Gly Gln Gly Thr Leu Val Thr Val Ser Ser
        115                 120                 125


<210> SEQ ID NO 164
<211> LENGTH: 111
<212> TYPE: PRT
<213> ORGANISM: Artificial Sequence
<220> FEATURE:
<223> OTHER INFORMATION: Synthetic (Light chain variable region of
      anti-Ang2 antibody 2-E6)

<400> SEQUENCE: 164

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Ala Asp Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Gly Tyr Val Phe Gly Gly Gly Thr Lys Leu Thr Val Leu Gly
            100                 105                 110


<210> SEQ ID NO 165
<211> LENGTH: 111
<212> TYPE: PRT
<213> ORGANISM: Artificial Sequence
<220> FEATURE:
<223> OTHER INFORMATION: Synthetic (Light chain variable region of
```

anti-Ang2 antibody 8-A5)

<400> SEQUENCE: 165

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Asn Asn
20 25 30

Tyr Val Thr Trp Tyr Gln Gln Leu Pro Gly Thr Ala Pro Lys Leu Leu
35 40 45

Ile Tyr Ala Asp Ser His Arg Pro Ser Gly Val Pro Asp Arg Phe Ser
50 55 60

Gly Ser Lys Ser Gly Thr Ser Ala Ser Leu Ala Ile Ser Gly Leu Arg
65 70 75 80

Ser Glu Asp Glu Ala Asp Tyr Tyr Cys Ala Thr Trp Asp Tyr Ser Leu
85 90 95

Ser Gly Tyr Val Phe Gly Gly Gly Thr Lys Leu Thr Val Leu Gly
100 105 110

<210> SEQ ID NO 166
<211> LENGTH: 111
<212> TYPE: PRT
<213> ORGANISM: Artificial Sequence
<220> FEATURE:
<223> OTHER INFORMATION: Synthetic (Light chain variable region of anti-Ang2 antibody 7-C9)

<400> SEQUENCE: 166

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Asn Asn
20 25 30

Asp Val Tyr Trp Tyr Gln Gln Leu Pro Gly Thr Ala Pro Lys Leu Leu
35 40 45

Ile Tyr Ala Asn Ser His Arg Pro Ser Gly Val Pro Asp Arg Phe Ser
50 55 60

Gly Ser Lys Ser Gly Thr Ser Ala Ser Leu Ala Ile Ser Gly Leu Arg
65 70 75 80

Ser Glu Asp Glu Ala Asp Tyr Tyr Cys Gly Thr Trp Asp Tyr Ser Leu
85 90 95

Ser Gly Tyr Val Phe Gly Gly Gly Thr Lys Leu Thr Val Leu Gly
100 105 110

<210> SEQ ID NO 167
<211> LENGTH: 111
<212> TYPE: PRT
<213> ORGANISM: Artificial Sequence
<220> FEATURE:
<223> OTHER INFORMATION: Synthetic (Light chain variable region of anti-Ang2 antibody 4-C11)

<400> SEQUENCE: 167

Gln Ser Val Leu Thr Gln Pro Pro Ser Ala Ser Gly Thr Pro Gly Gln
1 5 10 15

Arg Val Thr Ile Ser Cys Thr Gly Ser Ser Ser Asn Ile Gly Asn Asn
20 25 30

Asp Val Ser Trp Tyr Gln Gln Leu Pro Gly Thr Ala Pro Lys Leu Leu
35 40 45

Ile Tyr Ser Asp Ser Lys Arg Pro Ser Gly Val Pro Asp Arg Phe Ser
50 55 60

```
Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Gly Tyr Val Phe Gly Gly Gly Thr Lys Leu Thr Val Leu Gly
            100                 105                 110


<210> SEQ ID NO 168
<211> LENGTH: 111
<212> TYPE: PRT
<213> ORGANISM: Artificial Sequence
<220> FEATURE:
<223> OTHER INFORMATION: Synthetic (Light chain variable region of
      anti-Ang2 antibody 4-F5)

<400> SEQUENCE: 168

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ala Val Asn Trp Tyr Gln Gln Leu Pro Gly Thr Ala Pro Lys Leu Leu
        35                  40                  45

Ile Tyr Ala Asp Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Gly Tyr Val Phe Gly Gly Gly Thr Lys Leu Thr Val Leu Gly
            100                 105                 110


<210> SEQ ID NO 169
<211> LENGTH: 111
<212> TYPE: PRT
<213> ORGANISM: Artificial Sequence
<220> FEATURE:
<223> OTHER INFORMATION: Synthetic (Light chain variable region of
      anti-Ang2 antibody 4-F11)

<400> SEQUENCE: 169

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Ala Val Ser Trp Tyr Gln Gln Leu Pro Gly Thr Ala Pro Lys Leu Leu
        35                  40                  45

Ile Tyr Ser Asp Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Ala Tyr Val Phe Gly Gly Gly Thr Lys Leu Thr Val Leu Gly
            100                 105                 110


<210> SEQ ID NO 170
<211> LENGTH: 111
<212> TYPE: PRT
<213> ORGANISM: Artificial Sequence
```

<220> FEATURE:
<223> OTHER INFORMATION: Synthetic (Light chain variable region of anti-Ang2 antibody 4-H10)

<400> SEQUENCE: 170

Gln Ser Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Tyr Val Asn Trp Tyr Gln Gln Leu Pro Gly Thr Ala Pro Lys Leu Leu
35 40 45

Ile Tyr Ser Asp Ser His Arg Pro Ser Gly Val Pro Asp Arg Phe Ser
50 55 60

Gly Ser Lys Ser Gly Thr Ser Ala Ser Leu Ala Ile Ser Gly Leu Arg
65 70 75 80

Ser Glu Asp Glu Ala Asp Tyr Tyr Cys Gly Ala Trp Asp Asp Ser Leu
85 90 95

Ser Gly Tyr Val Phe Gly Gly Gly Thr Lys Leu Thr Val Leu Gly
100 105 110

<210> SEQ ID NO 171
<211> LENGTH: 111
<212> TYPE: PRT
<213> ORGANISM: Artificial Sequence
<220> FEATURE:
<223> OTHER INFORMATION: Synthetic (Light chain variable region of anti-Ang2 antibody 3-D3)

<400> SEQUENCE: 171

Gln Ser Val Leu Thr Gln Pro Pro Ser Ala Ser Gly Thr Pro Gly Gln
1 5 10 15

Arg Val Thr Ile Ser Cys Thr Gly Ser Ser Ser Asn Ile Gly Ser Asn
20 25 30

Tyr Val Ser Trp Tyr Gln Gln Leu Pro Gly Thr Ala Pro Lys Leu Leu
35 40 45

Ile Tyr Ser Asp Asn Lys Arg Pro Ser Gly Val Pro Asp Arg Phe Ser
50 55 60

Gly Ser Lys Ser Gly Thr Ser Ala Ser Leu Ala Ile Ser Gly Leu Arg
65 70 75 80

Ser Glu Asp Glu Ala Asp Tyr Tyr Cys Gly Thr Trp Asp Asp Ser Leu
85 90 95

Asn Gly Tyr Val Phe Gly Gly Gly Thr Lys Leu Thr Val Leu Gly
100 105 110

<210> SEQ ID NO 172
<211> LENGTH: 496
<212> TYPE: PRT
<213> ORGANISM: Artificial Sequence
<220> FEATURE:
<223> OTHER INFORMATION: Synthetic (human Ang2)
<220> FEATURE:
<221> NAME/KEY: MOD_RES
<222> LOCATION: (417)..(434)
<223> OTHER INFORMATION: Loop 1
<220> FEATURE:
<221> NAME/KEY: MOD_RES
<222> LOCATION: (447)..(454)
<223> OTHER INFORMATION: Loop 2
<220> FEATURE:
<221> NAME/KEY: MOD_RES
<222> LOCATION: (460)..(468)
<223> OTHER INFORMATION: Loop 3

<400> SEQUENCE: 172

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Ser Pro Tyr Val Ser Asn Ala
    50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
        115                 120                 125

Thr Asn Leu Leu Asn Gln Thr Ala Glu Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
    210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
        275                 280                 285

Lys Ser Gly His Thr Thr Asn Gly Ile Tyr Thr Leu Thr Phe Pro Asn
    290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
        355                 360                 365

Tyr Val Leu Lys Ile His Leu Lys Asp Trp Glu Gly Asn Glu Ala Tyr
    370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

```
Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
        435                 440                 445

Ala Cys Gly Pro Ser Asn Leu Asn Gly Met Tyr Tyr Pro Gln Arg Gln
    450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495
```

```
<210> SEQ ID NO 173
<211> LENGTH: 381
<212> TYPE: DNA
<213> ORGANISM: Artificial Sequence
<220> FEATURE:
<223> OTHER INFORMATION: Synthetic (Polyucleotide encoding heavy chain
      variable region of anti-Ang2 antibody 2-E6)

<400> SEQUENCE: 173

gaagtgcagc ttctggaatc aggcggtgga ctggtgcagc caggaggcag cctcaggctg     60

tcttgcgcag ccagcggatt taccttctcc gattacgcca tgagctgggt tagacaggcc    120

cctggcaagg ggctggagtg ggtcagtgcc atttaccccg actccgggaa taagtattac    180

gctgactctg tgaaaggtag attcactatc tcaagagaca actccaaaaa tacattgtac    240

ttacagatga actcactgcg cgctgaggat acagcagtgt attattgtgc gcggcactcg    300

agtgatccta aggtcaaaag cggatactat gacgacggca tggatgtttg gggccaaggg    360

actctcgtaa ccgtgtcttc t                                              381


<210> SEQ ID NO 174
<211> LENGTH: 333
<212> TYPE: DNA
<213> ORGANISM: Artificial Sequence
<220> FEATURE:
<223> OTHER INFORMATION: Synthetic (Polyucleotide encoding light chain
      variable region of anti-Ang2 antibody 2-E6)

<400> SEQUENCE: 174

cagtcagtcc tgacacagcc ccctagtgct tccggaaccc ctgggcagag ggtgaccatc     60

tcatgctcag gtagctccag caacattgga aacaatgcag ttaattggta tcagcaactg    120

cccgggaccg ccccaaagct tctgatctac gctgatagta atagaccatc tggagtgcct    180

gacagattca gtggttcgaa aagcggcact tctgcatcct tggccatttc tggcttaaga    240

tctgaagatg aggccgacta ttactgtggc tcttgggact actccctgag cggatatgtg    300

tttgggggcg gaactaagct cacagtccta ggc                                 333


<210> SEQ ID NO 175
<211> LENGTH: 363
<212> TYPE: DNA
<213> ORGANISM: Artificial Sequence
<220> FEATURE:
<223> OTHER INFORMATION: Synthetic (Polyucleotide encoding heavy chain
      variable region of anti-Ang2 antibody 8-A5)

<400> SEQUENCE: 175

gaggtccagc tgctcgaatc aggcggtggg ctggtgcagc caggcggctc cctgaggtta     60

agttgcgccg cttctggctt tacatttagc gattattaca tgtcctgggt ccgccaggcc    120
```

cccgggaaag gtctggagtg ggtgagcgga atttaccctt ccgggggaag cacctattac 180
gcggattctg taaagggtag attcactatc tcaagagaca attctaagaa taccctgtat 240
ttgcagatga acagtcttag agccgaagac acagcagttt attattgtgc aagagacccc 300
agtactctaa cctacgctgg cttcgattac tggggacaag gaacgctcgt gacagtgtca 360
agc 363

<210> SEQ ID NO 176
<211> LENGTH: 333
<212> TYPE: DNA
<213> ORGANISM: Artificial Sequence
<220> FEATURE:
<223> OTHER INFORMATION: Synthetic (Polyucleotide encoding light chain variable region of anti-Ang2 antibody 8-A5)

<400> SEQUENCE: 176
caaagtgttc tcacacagcc gccatccgct tccgggaccc ctggacagag agtgaccatc 60
agttgtagtg gctcttcgag caatattggc aataactatg tgacatggta tcagcagctt 120
cctggaacag cccccaaact gctcatctat gccgacagcc acagaccatc aggtgtcccc 180
gatagatttt ctgggtcaaa gtcaggaact agcgcaagcc tggccatttc tggattaagg 240
tccgaggacg aagctgatta ctattgcgca acttgggact actctctgtc tggttacgtg 300
ttcggcggcg gaaccaagtt gacggtccta ggc 333

<210> SEQ ID NO 177
<211> LENGTH: 381
<212> TYPE: DNA
<213> ORGANISM: Artificial Sequence
<220> FEATURE:
<223> OTHER INFORMATION: Synthetic (Polyucleotide encoding heavy chain variable region of anti-Ang2 antibody 7-C9)

<400> SEQUENCE: 177
gaggtgcaac tcctggagtc aggaggcggc ctggtccagc ccggcgggag tcttagactc 60
tcgtgtgccg caagcgggtt tacattcagt aactacgcca tgtcctgggt cagacaggct 120
cctggaaagg gactggaatg ggtttctgcc attagctccg gcggaggtaa tatctattac 180
gctgattccg ttaaagggag gtttacaatc tctcgggata acagcaaaaa tactttgtat 240
ctgcagatga atagcttaag agccgaagac actgcagtgt actactgcgc gaagagcggt 300
attcaaccct ctccaccatc catgtcatca gcttatgcaa tggacgtatg gggcagggc 360 accctggtga ccgtgagttc t 381

<210> SEQ ID NO 178
<211> LENGTH: 333
<212> TYPE: DNA
<213> ORGANISM: Artificial Sequence
<220> FEATURE:
<223> OTHER INFORMATION: Synthetic (Polyucleotide encoding light chain variable region of anti-Ang2 antibody 7-C9)

<400> SEQUENCE: 178
cagagcgtcc tgacacaacc tccatccgct tctgggacgc ctggacagag agtgacaatt 60
tcttgcagcg gctcatcttc aaatattgga aacaatgacg tttattggta ccagcagctc 120
ccagggaccg ccccaaagct gctgatctat gcaaactcac acagacccag cggagtgccc 180
gatagattca gtggatccaa atccggcact agtgccagct tggcaatctc ggggctgaga 240
tctgaagacg aggctgatta ctattgtggt acctgggatt actccttaag tggttacgtg 300
tttggcgggg gcactaagct taccgtccta ggc 333

<210> SEQ ID NO 179
<211> LENGTH: 381
<212> TYPE: DNA
<213> ORGANISM: Artificial Sequence
<220> FEATURE:
<223> OTHER INFORMATION: Synthetic (Polyucleotide encoding heavy chain
variable region of anti-Ang2 antibody 4-C11)

<400> SEQUENCE: 179
gaagtacagc tgctggagtc gggtggtgga ctggttcagc caggaggctc attaaggctg 60
agctgcgccg caagcggttt cactttttct gattatgcta tgtcctgggt cagacaggcc 120
cctgggaagg gactcgagtg ggtctcaagt atttaccccg acgatggaaa tacctactat 180
gccgatagcg tgaaggggcg ctttacaatc tctagagata attctaaaaa caccctgtac 240
cttcaaatga actcattgcg ggcagaagac acagcggtgt actattgtgc tagacacacg 300
tcccaccata ccagcatcga cggctactat tattacggga tggacggctg gggccagggc 360
actctcgtga cagtgtccag t 381

<210> SEQ ID NO 180
<211> LENGTH: 333
<212> TYPE: DNA
<213> ORGANISM: Artificial Sequence
<220> FEATURE:
<223> OTHER INFORMATION: Synthetic (Polyucleotide encoding light chain
variable region of anti-Ang2 antibody 4-C11)

<400> SEQUENCE: 180
cagtcagtcc tgactcagcc accctccgca agcgggacac ctggacaaag agttactatc 60
tcttgcaccg ggtcaagctc caatatcggt aacaatgatg tgagttggta ccagcagtta 120
ccaggcaccg ccccgaaact gcttatttac tcagacagca aaagaccctc tggcgtgcct 180
gacagattct caggaagcaa gagtggcacg tctgcttcct tggccatttc gggtctgaga 240
tccgaggacg aagctgatta ttattgtgga agctgggatt atagtctgtc tggctacgtg 300
tttgggggcg gaaccaagct cacagtccta ggc 333

<210> SEQ ID NO 181
<211> LENGTH: 387
<212> TYPE: DNA
<213> ORGANISM: Artificial Sequence
<220> FEATURE:
<223> OTHER INFORMATION: Synthetic (Polyucleotide encoding heavy chain
variable region of anti-Ang2 antibody 4-F5)

<400> SEQUENCE: 181
gaggtgcagt tgctcgagtc cgggggtggc ctggtgcagc caggaggaag cctgagactg 60
agctgcgcag cctcaggttt cacattctcc gattacgaca tgtcctgggt taggcaagcc 120
cccggcaagg ggctggaatg ggtaagctct atcagccacg gcgacagtaa caaatattat 180
gcagactctg ttaagggacg gtttaccatt tcacgcgata actcaaagaa tacactgtac 240
cttcaaatga atagtctcag agctgaagat accgccgtgt attactgtgc taaatcgtcc 300
ggaatccagg agagtccccc tacttattac tactatggga tggatgtgtg gggccagggc 360
accctggtca ctgtctcttc tgctagc 387

<210> SEQ ID NO 182
<211> LENGTH: 333
<212> TYPE: DNA

<213> ORGANISM: Artificial Sequence
<220> FEATURE:
<223> OTHER INFORMATION: Synthetic (Polyucleotide encoding light chain
      variable region of anti-Ang2 antibody 4-F5)

<400> SEQUENCE: 182

```
cagtctgtgt tgacccagcc cccttctgca tctggcaccc ccggacagag agtcactata     60

agttgttctg gtagctcctc aaatatcggc tcaaacgccg tgaattggta ccagcaatta    120

ccaggaacag ctcctaagct gcttatctat gcagacagta acagaccaag cggcgttcct    180

gatagattct caggctccaa gtccgggact agtgcctcgc tggctattag cggtctcaga    240

agtgaagatg aggccgatta ctattgcgga agctgggact actccctgag cggctatgtg    300

tttggaggag ggacaaaact caccgtccta ggc                                 333
```

<210> SEQ ID NO 183
<211> LENGTH: 381
<212> TYPE: DNA
<213> ORGANISM: Artificial Sequence
<220> FEATURE:
<223> OTHER INFORMATION: Synthetic (Polyucleotide encoding heavy chain
      variable region of anti-Ang2 antibody 4-F11)

<400> SEQUENCE: 183

```
gaggtgcaac tgctggagag tggtgggggc cttgttcagc ccggcggatc cttgaggctg     60

tcatgcgctg cgtctggctt tactttcagc gattacgcaa tgagttgggt gagacaggct    120

ccaggaaaag gcctggaatg ggtcagctcc atttatcctg acgatggtaa cacatattac    180

gccgacagcg taaaaggacg gttcaccatc tctcgcgata attctaagaa caccctgtat    240

ctccagatga atagcctgag agcagaagac accgccgtgt actactgtgc caagcatcct    300

gtgagattaa acctgcaccc aatgtactat tattacggca tggacgtttg ggggcagggg    360

acactcgtga ctgtctcctc a                                              381
```

<210> SEQ ID NO 184
<211> LENGTH: 333
<212> TYPE: DNA
<213> ORGANISM: Artificial Sequence
<220> FEATURE:
<223> OTHER INFORMATION: Synthetic (Polyucleotide encoding light chain
      variable region of anti-Ang2 antibody 4-F11)

<400> SEQUENCE: 184

```
cagtctgtgt taacacaacc tccaagtgca tccggaacgc cgggccagag agtgactatc     60

agctgcaccg gcagctcgtc caatatcggt aacaacgcag ttagttggta ccagcagctt    120

cccggcacag ctccaaagct cttgatttac agcgattcac aaagacctag tggtgtcccc    180

gatagatttt ctgggagtaa gagcgggacc agtgcctccc tggctatatc aggactgaga    240

tctgaagatg aggctgacta ttactgtgcc acttgggact attcactctc tgcctatgtg    300

ttcgggggcg gaaccaaact gacagtccta ggc                                 333
```

<210> SEQ ID NO 185
<211> LENGTH: 363
<212> TYPE: DNA
<213> ORGANISM: Artificial Sequence
<220> FEATURE:
<223> OTHER INFORMATION: Synthetic (Polyucleotide encoding heavy chain
      variable region of anti-Ang2 antibody 4-H10)

<400> SEQUENCE: 185

```
gaggttcagt tgctggagag tggcggcggc ttagtgcagc caggtggcag cctgcgcctt     60
```

tcttgtgccg ccagtgggtt taccttctcc tcctacgaca tgagctgggt gcggcaggct 120
cccggcaaag gtcttgaatg ggtgtcactg atcagccctg acagttcctc aatctattat 180
gcagattcag tcaagggaag atttaccata agcagagata attccaagaa tactctgtac 240
ctacagatga actcgctcag agccgaagat accgcagtct actactgcgc taaagacctg 300
atttctttct ggaggggggg attcgactat tgggggcaag gaacactcgt aacagtgtct 360
agc 363

<210> SEQ ID NO 186
<211> LENGTH: 333
<212> TYPE: DNA
<213> ORGANISM: Artificial Sequence
<220> FEATURE:
<223> OTHER INFORMATION: Synthetic (Polyucleotide encoding light chain variable region of anti-Ang2 antibody 4-H10)

<400> SEQUENCE: 186
cagagcgtgc tcacccaacc tcccagtgca tccggaacgc ctggtcagag agtgacaatt 60
agctgctcag ggtcttcctc taacatcggg tccaattatg tcaattggta tcagcagttg 120
ccaggtacag ctcccaaact gctgatctac agtgattccc acagacctag cggcgttcca 180
gacagattta gcggatccaa gtcgggaact tctgcaagcc tcgctatttc tggcctgaga 240
agtgaggacg aagccgatta ttactgtggg gcctgggacg attcattatc aggatacgtg 300
ttcggaggcg gcaccaagct tactgtccta ggc 333

<210> SEQ ID NO 187
<211> LENGTH: 381
<212> TYPE: DNA
<213> ORGANISM: Artificial Sequence
<220> FEATURE:
<223> OTHER INFORMATION: Synthetic (Polyucleotide encoding heavy chain variable region of anti-Ang2 antibody 3-D3)

<400> SEQUENCE: 187
gaggtacagc tgctggaaag tgggggcggt ctggtgcagc caggggggaag cctccggctt 60 tcatgcgccg caagcggctt tacattcagt gactatgaca tgagttgggt ccgacaagcc 120
cccggaaagg gcctggagtg ggtgtctgga atctcctccg atgacggcaa tacttattac 180
gctgactccg ttaaaggtag gttcaccatc tctcgcgata actctaaaaa caccctctac 240
ctgcagatga atagcttgag ggcagaagat acggctgtct actattgtgc cagacctaca 300
attgacaagt acacattaag agggtattat tcatacggca tggatgtttg ggacaggga 360 actctagtga ccgtgtccag c 381

<210> SEQ ID NO 188
<211> LENGTH: 333
<212> TYPE: DNA
<213> ORGANISM: Artificial Sequence
<220> FEATURE:
<223> OTHER INFORMATION: Synthetic (Polyucleotide encoding light chain variable region of anti-Ang2 antibody 3-D3)

<400> SEQUENCE: 188
cagtcagtgc tgacacagcc tccaagcgct tccgggacac ctggacaaag agttaccatt 60
tcgtgcaccg gatcctcctc aaacatcggt agcaattatg tgtcttggta ccagcagctc 120
cccgggactg cccccaaact cttgatctac agcgacaaca agagaccatc tggtgtgcct 180
gatagattca gtgggagtaa gtcaggaacg agtgcctctc tggctatttc tggcctgaga 240
agcgaagatg aggcagacta ttattgtggc acctgggatg actccctgaa tggctacgtc 300
tttggcggcg gaacaaaact tactgtccta ggc 333

<210> SEQ ID NO 189
<211> LENGTH: 738
<212> TYPE: PRT
<213> ORGANISM: Artificial Sequence
<220> FEATURE:
<223> OTHER INFORMATION: Synthetic (heavy chain of anti-c-Met antibody and anti-Ang2 scFv linked to c-terminus of the heavy chain, in bispecific anti-c-Met/anti-Ang2 antibody)

<400> SEQUENCE: 189

Met Glu Trp Ser Trp Val Phe Leu Val Thr Leu Leu Asn Gly Ile Gln
1 5 10 15

Cys Glu Val Gln Leu Val Glu Ser Gly Gly Gly Leu Val Gln Pro Gly
20 25 30

Gly Ser Leu Arg Leu Ser Cys Ala Ala Ser Gly Phe Thr Phe Thr Asp
35 40 45

Tyr Tyr Met Ser Trp Val Arg Gln Ala Pro Gly Lys Gly Leu Glu Trp
50 55 60

Leu Gly Phe Ile Arg Asn Lys Ala Asn Gly Tyr Thr Thr Glu Tyr Ser
65 70 75 80

Ala Ser Val Lys Gly Arg Phe Thr Ile Ser Arg Asp Asn Ser Lys Asn
85 90 95

Thr Leu Tyr Leu Gln Met Asn Ser Leu Arg Ala Glu Asp Thr Ala Val
100 105 110

Tyr Tyr Cys Ala Arg Asp Asn Trp Phe Ala Tyr Trp Gly Gln Gly Thr
115 120 125

Leu Val Thr Val Ser Ser Ala Ser Thr Lys Gly Pro Ser Val Phe Pro
130 135 140

Leu Ala Pro Cys Ser Arg Ser Thr Ser Glu Ser Thr Ala Ala Leu Gly
145 150 155 160

Cys Leu Val Lys Asp Tyr Phe Pro Glu Pro Val Thr Val Ser Trp Asn
165 170 175

Ser Gly Ala Leu Thr Ser Gly Val His Thr Phe Pro Ala Val Leu Gln
180 185 190

Ser Ser Gly Leu Tyr Ser Leu Ser Ser Val Val Thr Val Pro Ser Ser
195 200 205

Asn Phe Gly Thr Gln Thr Tyr Thr Cys Asn Val Asp His Lys Pro Ser
210 215 220

Asn Thr Lys Val Asp Lys Thr Val Glu Arg Lys Cys Cys Val Glu Cys
225 230 235 240

Pro Pro Cys Pro Ala Pro Pro Val Ala Gly Pro Ser Val Phe Leu Phe
245 250 255

Pro Pro Lys Pro Lys Asp Thr Leu Met Ile Ser Arg Thr Pro Glu Val
260 265 270

Thr Cys Val Val Val Asp Val Ser His Glu Asp Pro Glu Val Gln Phe
275 280 285

Asn Trp Tyr Val Asp Gly Val Glu Val His Asn Ala Lys Thr Lys Pro
290 295 300

Arg Glu Glu Gln Phe Asn Ser Thr Phe Arg Val Val Ser Val Leu Thr
305 310 315 320

Val Val His Gln Asp Trp Leu Asn Gly Lys Glu Tyr Lys Cys Lys Val
325 330 335

-continued

```
Ser Asn Lys Gly Leu Pro Ala Pro Ile Glu Lys Thr Ile Ser Lys Thr
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Gly Gly Gly Gly Ser
    450                 455                 460

Gly Gly Gly Gly Ser Glu Val Gln Leu Leu Glu Ser Gly Gly Gly Leu
465                 470                 475                 480

Val Gln Pro Gly Gly Ser Leu Arg Leu Ser Cys Ala Ala Ser Gly Phe
                485                 490                 495

Thr Phe Ser Ser Tyr Asp Met Ser Trp Val Arg Leu Ala Pro Gly Lys
            500                 505                 510

Gly Leu Glu Trp Val Ser Leu Ile Ser Pro Asp Ser Ser Ser Ile Tyr
        515                 520                 525

Tyr Ala Asp Ser Val Lys Gly Arg Phe Thr Ile Ser Arg Asp Asn Ser
    530                 535                 540

Lys Asn Thr Leu Tyr Leu Gln Met Asn Ser Leu Arg Ala Glu Asp Thr
545                 550                 555                 560

Ala Val Tyr Tyr Cys Ala Lys Asp Leu Ile Ser Phe Trp Arg Gly Gly
                565                 570                 575

Phe Asp Tyr Trp Gly Gln Gly Thr Leu Val Thr Val Ser Ser Gly Gly
            580                 585                 590

Gly Gly Ser Gly Gly Gly Gly Ser Gly Ser Gly Gly Ser Gln Ser Val
        595                 600                 605

Leu Thr Gln Pro Pro Ser Ala Ser Gly Thr Pro Gly Gln Arg Val Thr
    610                 615                 620

Ile Ser Cys Ser Gly Ser Ser Ser Asn Ile Gly Ser Asn Tyr Val Asn
625                 630                 635                 640

Trp Tyr Gln Gln Leu Pro Gly Thr Ala Pro Lys Leu Leu Ile Tyr Ser
                645                 650                 655

Asp Ser His Arg Pro Ser Gly Val Pro Asp Arg Phe Ser Gly Ser Lys
            660                 665                 670

Ser Gly Thr Ser Ala Ser Leu Ala Ile Ser Gly Leu Arg Ser Glu Asp
        675                 680                 685

Glu Ala Asp Tyr Tyr Cys Gly Ala Trp Asp Asp Ser Leu Ser Gly Tyr
    690                 695                 700

Val Phe Gly Gly Gly Thr Lys Leu Thr Val Leu Gly Gln Ala Gly Gln
705                 710                 715                 720

His His His His His His Gly Ala Tyr Pro Tyr Asp Val Pro Asp Tyr
                725                 730                 735

Ala Ser
```

<210> SEQ ID NO 190
<211> LENGTH: 19
<212> TYPE: DNA
<213> ORGANISM: Artificial Sequence
<220> FEATURE:
<223> OTHER INFORMATION: Synthetic (pC3X-f primer)

<400> SEQUENCE: 190
gcacgacagg tttcccgac 19

<210> SEQ ID NO 191
<211> LENGTH: 20
<212> TYPE: DNA
<213> ORGANISM: Artificial Sequence
<220> FEATURE:
<223> OTHER INFORMATION: Synthetic (pC3X-b primer)

<400> SEQUENCE: 191
aaccatcgat agcagcaccg 20

<210> SEQ ID NO 192
<211> LENGTH: 17
<212> TYPE: PRT
<213> ORGANISM: Artificial Sequence
<220> FEATURE:
<223> OTHER INFORMATION: Synthetic Signal peptide

<400> SEQUENCE: 192

Met Glu Trp Ser Trp Val Phe Leu Val Thr Leu Leu Asn Gly Ile Gln
1 5 10 15

Cys

<210> SEQ ID NO 193
<211> LENGTH: 117
<212> TYPE: PRT
<213> ORGANISM: Artificial Sequence
<220> FEATURE:
<223> OTHER INFORMATION: Synthetic Heavy chain variable region of anti-c-Met antibody

<400> SEQUENCE: 193

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Thr Asp Tyr
20 25 30

Tyr Met Ser Trp Val Arg Gln Ala Pro Gly Lys Gly Leu Glu Trp Leu
35 40 45

Gly Phe Ile Arg Asn Lys Ala Asn Gly Tyr Thr Thr Glu Tyr Ser Ala
50 55 60

Ser Val Lys Gly Arg Phe Thr Ile Ser Arg Asp Asn Ser Lys Asn Thr
65 70 75 80

Leu Tyr Leu Gln Met Asn Ser Leu Arg Ala Glu Asp Thr Ala Val Tyr
85 90 95

Tyr Cys Ala Arg Asp Asn Trp Phe Ala Tyr Trp Gly Gln Gly Thr Leu
100 105 110

Val Thr Val Ser Ser
115

<210> SEQ ID NO 194
<211> LENGTH: 325
<212> TYPE: PRT
<213> ORGANISM: Artificial Sequence
<220> FEATURE:

<223> OTHER INFORMATION: Synthetic Fc (IgG2)

<400> SEQUENCE: 194

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Asn Phe Gly Thr Gln Thr
65 70 75 80

Tyr Thr Cys Asn Val Asp His Lys Pro Ser Asn Thr Lys Val Asp Lys
85 90 95

Thr Val Glu Arg Lys Cys Cys Val Glu Cys Pro Pro Cys Pro Ala Pro
100 105 110

Pro Val Ala Gly Pro Ser Val Phe Leu Phe Pro Pro Lys Pro Lys Asp
115 120 125

Thr Leu Met Ile Ser Arg Thr Pro Glu Val Thr Cys Val Val Val Asp
130 135 140

Val Ser His Glu Asp Pro Glu Val Gln Phe Asn Trp Tyr Val Asp Gly
145 150 155 160

Val Glu Val His Asn Ala Lys Thr Lys Pro Arg Glu Glu Gln Phe Asn
165 170 175

Ser Thr Phe Arg Val Val Ser Val Leu Thr Val Val His Gln Asp Trp
180 185 190

Leu Asn Gly Lys Glu Tyr Lys Cys Lys Val Ser Asn Lys Gly Leu Pro
195 200 205

Ala Pro Ile Glu Lys Thr Ile Ser Lys Thr Lys Gly Gln Pro Arg Glu
210 215 220

Pro Gln Val Tyr Thr Leu Pro Pro Ser Arg Glu Glu Met Thr Lys Asn
225 230 235 240

Gln Val Ser Leu Thr Cys Leu Val Lys Gly Phe Tyr Pro Ser Asp Ile
245 250 255

Ala Val Glu Trp Glu Ser Asn Gly Gln Pro Glu Asn Asn Tyr Lys Thr
260 265 270

Thr Pro Pro Met Leu Asp Ser Asp Gly Ser Phe Phe Leu Tyr Ser Lys
275 280 285

Leu Thr Val Asp Lys Ser Arg Trp Gln Gln Gly Asn Val Phe Ser Cys
290 295 300

Ser Val Met His Glu Ala Leu His Asn His Tyr Thr Gln Lys Ser Leu
305 310 315 320

Ser Leu Ser Pro Gly
325

<210> SEQ ID NO 195
<211> LENGTH: 10
<212> TYPE: PRT
<213> ORGANISM: Artificial Sequence
<220> FEATURE:
<223> OTHER INFORMATION: Synthetic Peptide linker (linking the
C-terminus of Fcand the anti-Ang2 scFv)

<400> SEQUENCE: 195

Gly Gly Gly Gly Ser Gly Gly Gly Gly Ser

```
1               5                   10


<210> SEQ ID NO 196
<211> LENGTH: 121
<212> TYPE: PRT
<213> ORGANISM: Artificial Sequence
<220> FEATURE:
<223> OTHER INFORMATION: Synthetic Heavy chain variable region of the
      anti-Ang2 scFv

<400> SEQUENCE: 196

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Leu Ala Pro Gly Lys Gly Leu Glu Trp Val
        35                  40                  45

Ser Leu Ile Ser Pro Asp Ser Ser Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Ile Ser Phe Trp Arg Gly Gly Phe Asp Tyr Trp Gly
            100                 105                 110

Gln Gly Thr Leu Val Thr Val Ser Ser
        115                 120


<210> SEQ ID NO 197
<211> LENGTH: 10
<212> TYPE: PRT
<213> ORGANISM: Artificial Sequence
<220> FEATURE:
<223> OTHER INFORMATION: Synthetic Peptide linker (linking the heavy
      chain variable region and the light chain variable region of the
      anti-Ang2 scFv)

<400> SEQUENCE: 197

Gly Gly Gly Gly Ser Gly Gly Gly Gly Ser
1               5                   10


<210> SEQ ID NO 198
<211> LENGTH: 133
<212> TYPE: PRT
<213> ORGANISM: Artificial Sequence
<220> FEATURE:
<223> OTHER INFORMATION: Synthetic

<400> SEQUENCE: 198

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Asn Trp Tyr Gln Gln Leu Pro Gly Thr Ala Pro Lys Leu Leu
        35                  40                  45

Ile Tyr Ser Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95
```

```
Ser Gly Tyr Val Phe Gly Gly Gly Thr Lys Leu Thr Val Leu Gly Gln
            100                 105                 110

Ala Gly Gln His His His His His His Gly Ala Tyr Pro Tyr Asp Val
        115                 120                 125

Pro Asp Tyr Ala Ser
    130


<210> SEQ ID NO 199
<211> LENGTH: 20
<212> TYPE: PRT
<213> ORGANISM: Artificial Sequence
<220> FEATURE:
<223> OTHER INFORMATION: Synthetic Signal peptide

<400> SEQUENCE: 199

Met Asp Ser Gln Ala Gln Val Leu Met Leu Leu Leu Leu Ser Val Ser
1               5                   10                  15

Gly Thr Cys Gly
            20


<210> SEQ ID NO 200
<211> LENGTH: 220
<212> TYPE: PRT
<213> ORGANISM: Artificial Sequence
<220> FEATURE:
<223> OTHER INFORMATION: Synthetic Light chain variable region of the
      anti-c-Met antibody

<400> SEQUENCE: 200

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp Tyr Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

-continued

```
<210> SEQ ID NO 201
<211> LENGTH: 8
<212> TYPE: PRT
<213> ORGANISM: Artificial Sequence
<220> FEATURE:
<223> OTHER INFORMATION: Synthetic

<400> SEQUENCE: 201

Asp Tyr Lys Asp Asp Asp Asp Lys
1               5


<210> SEQ ID NO 202
<211> LENGTH: 30
<212> TYPE: DNA
<213> ORGANISM: Artificial Sequence
<220> FEATURE:
<223> OTHER INFORMATION: Synthetic

<400> SEQUENCE: 202

ggcggtggtg gttccggagg cggcggatcc                                    30
```